(12) United States Patent
Wang et al.

(10) Patent No.: US 12,193,317 B2
(45) Date of Patent: Jan. 7, 2025

(54) ORGANIC SEMICONDUCTING COMPOUNDS

(71) Applicant: FLEXENABLE TECHNOLOGY LTD., Cambridge (GB)

(72) Inventors: Changsheng Wang, Eastleigh (GB); William Mitchell, Chandler's Ford (GB); Thomas Hodsden, London (GB); Martin Heeney, Woking (GB); Julianna Panidi, London (GB)

(73) Assignee: FLEXENABLE TECHNOLOGY LIMITED, Cambridge (GB)

(*) Notice: Subject to any disclaimer, the term of this patent is extended or adjusted under 35 U.S.C. 154(b) by 874 days.

(21) Appl. No.: 17/260,147

(22) PCT Filed: Jul. 10, 2019

(86) PCT No.: PCT/EP2019/068496
§ 371 (c)(1),
(2) Date: Jan. 13, 2021

(87) PCT Pub. No.: WO2020/011831
PCT Pub. Date: Jan. 16, 2020

(65) Prior Publication Data
US 2022/0131078 A1    Apr. 28, 2022

(30) Foreign Application Priority Data

Jul. 13, 2018 (ER) .................................. 18183372

(51) Int. Cl.
| | | |
|---|---|---|
| *H10K 85/10* | (2023.01) | |
| *C07D 495/04* | (2006.01) | |
| *C08G 61/12* | (2006.01) | |
| *H10K 85/60* | (2023.01) | |
| *H10K 30/30* | (2023.01) | |

(52) U.S. Cl.
CPC ......... *H10K 85/113* (2023.02); *C07D 495/04* (2013.01); *C08G 61/126* (2013.01); *H10K 85/151* (2023.02); *H10K 85/6576* (2023.02); *C08G 2261/124* (2013.01); *C08G 2261/142* (2013.01); *C08G 2261/146* (2013.01); *C08G 2261/18* (2013.01); *C08G 2261/228* (2013.01); *C08G 2261/3243* (2013.01); *C08G 2261/91* (2013.01); *C08G 2261/92* (2013.01); *C08G 2261/94* (2013.01); *C08G 2261/95* (2013.01); *H10K 30/30* (2023.02)

(58) Field of Classification Search
CPC .... C08G 2261/3245; C08G 2261/3243; H10K 85/113; H10K 85/151; H10K 85/6576
See application file for complete search history.

(56) References Cited

U.S. PATENT DOCUMENTS

| | | |
|---|---|---|
| 5,198,153 A | 3/1993 | Angelopoulos et al. |
| 5,355,235 A | 10/1994 | Nishizawa et al. |
| 5,892,244 A | 4/1999 | Tanaka et al. |
| 5,998,804 A | 12/1999 | Suh et al. |
| 6,353,072 B1 | 3/2002 | Towns et al. |
| 6,723,394 B1 | 4/2004 | Sirringhaus et al. |
| 6,891,583 B1 | 5/2005 | Smith et al. |
| 7,095,044 B2 | 8/2006 | Brown et al. |
| 7,247,761 B2 | 7/2007 | Falcou et al. |
| 8,299,247 B2 | 10/2012 | Morishita |
| 10,038,150 B2 | 7/2018 | Burschka et al. |
| 10,069,025 B2 | 9/2018 | Snaith et al. |
| 10,340,457 B2 | 7/2019 | Mansoor |
| 11,258,024 B2 | 2/2022 | Snaith et al. |
| 11,276,734 B2 | 3/2022 | Snaith et al. |
| 11,302,833 B2 | 4/2022 | Snaith et al. |
| 2003/0021913 A1 | 1/2003 | O |
| 2007/0102696 A1 | 5/2007 | Brown et al. |
| 2015/0200377 A1 | 7/2015 | Etgar et al. |
| 2015/0302995 A1 | 10/2015 | Ignatyev et al. |
| 2015/0310998 A1 | 10/2015 | Ignatyev et al. |
| 2018/0309081 A1 | 10/2018 | Ikeda |

FOREIGN PATENT DOCUMENTS

| | | |
|---|---|---|
| EP | 2045848 B1 | 9/2017 |
| WO | 2017069208 A1 | 4/2017 |

OTHER PUBLICATIONS

Jean-David Peltier et al: "Electron-Deficient Dihydroindaceno-Dithiophene Regioisomers for n-Type Organic Field-Effect Transistors", ACS Applied Materials & Interfaces, vol. 9, No. 9, Mar. 8, 2017 (Mar. 8, 2017), US, pp. 8219-8232, XP055419462, ISSN: 1944-8244, DOI: 10.1021/acsami.6b16333.

Hongkun Tian et al: "A feasibly synthesized ladder-type conjugated molecule as the novel high mobility n-type organic semiconductor", Journal of Materials Chemistry, Royal Society of Chemistry, GB, vol. 20, No. 37, Oct. 7, 2010 (Oct. 7, 2010), pp. 7998-8004, XP002685982, ISSN: 0959-9428, [retrieved on Aug. 16, 2010], DOI: 10.1039/COJM01173H.

International Search report PCT/EP2019/068496 dated Jan. 19, 2021 (pp. 1-13).

*Primary Examiner* — Khanh T Nguyen
(74) *Attorney, Agent, or Firm* — Tarolli, Sundheim, Covell & Tummino LLP

(57) ABSTRACT

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

23 Claims, No Drawings

ORGANIC SEMICONDUCTING COMPOUNDS

TECHNICAL FIELD

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, perovskite-based solar cell (PSC) devices, sensors, memory elements and logic circuits to name just a few. The organic semiconducting materials are typically present in the electronic device in the form of a thin layer, for example of between 50 and 300 nm thickness.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 10%.

Another particular area of importance is OFETs. The performance of OFET devices is principally based upon the charge carrier mobility of the semiconducting material and the on/off current ratio, so the ideal semiconductor should have a low conductivity in the off state, combined with high charge carrier mobility ($>1\times10^{-3}$ cm$^2$ V$^{-1}$ s$^{-1}$). In addition, it is important that the semiconducting material is stable to oxidation i.e. it has a high ionisation potential, as oxidation leads to reduced device performance. Further requirements for the semiconducting material are good processability, especially for large-scale production of thin layers and desired patterns, and high stability, film uniformity and integrity of the organic semiconductor layer.

Organic photodetectors (OPDs) are a further particular area of importance, for which conjugated light-absorbing polymers offer the hope of allowing efficient devices to be produced by solution-processing technologies, such as spin casting, dip coating or ink jet printing, to name a few only.

The photosensitive layer in an OPV or OPD device is usually composed of at least two materials, a p-type semiconductor, which is typically a conjugated polymer, an oligomer or a defined molecular unit, and an n-type semiconductor, which is typically a fullerene or substituted fullerene, graphene, a metal oxide, or quantum dots. Very recently, non-fullerene acceptors (NFAs) have also shown remarkable potential in OPV and OPD applications with superior performances compared with their fullerene counterparts (for reviews, see: J. Hou, et al., *Nature Mater.*, 2017, 17, 119; C. Yan, et al., *Nature Rev. Mater.*, 2018, 3, 18003).

However, the OSC materials disclosed in prior art for use in OE devices have several drawbacks. For example, the fullerenes or fullerene derivatives which have hitherto been used as electron acceptors in OPV or OPD devices are often difficult to synthesize or purify, and/or do not absorb light strongly in the near IR spectrum >700 nm, or do often not form a favourable morphology and/or miscibility with the donor material.

Therefore, there is still a need for OSC materials for use in OE devices like OPVs, PSCs, OPDs and OFETs, which have advantageous properties, in particular good processability, a high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide new OSC compounds, especially n-type OSCs, which can overcome the drawbacks of the OSCs from prior art, and which provide one or more of the above-mentioned advantageous properties, especially easy synthesis by methods suitable for mass production, good processability, high stability, long lifetime in OE devices, good solubility in organic solvents, high charge carrier mobility, and a low bandgap. Another aim of the invention was to extend the pool of OSC materials and n-type OSCs available to the expert. Other aims of the present invention are immediately evident to the expert from the following detailed description.

Moreover, many organic electronic compounds reported for use as n-type semiconductors often show drawbacks such as a lack of stability in air/ambient conditions, or a large contact resistance at common electrodes. These issues result in the need for compounds with very deep LUMO energies (i.e. high electron affinities), with a benchmark usually quoted at around −4 eV for ambient stability.

Therefore another aim of the present invention was to provide n-type OSCs which have deep LUMO energy level.

The inventors of the present invention have found that one or more of the above aims can be achieved by providing compounds as disclosed and claimed hereinafter.

These compounds represent an alternative type of n-type organic semiconductors which do not include a fullerene moiety, and which are hereinafter also referred to as "non-fullerene acceptor(s)" or "NFA(s)".

The compounds according to the present invention are further characterized in that they comprise an indacenodithiophene (IDT) polycyclic core with sp$^2$ hybridised C atoms in the bridge positions between the central benzene rings and the outer aryl or heteroaryl groups. It was found that the combination of the IDT core, which is inherently electron-rich and therefore often used in electron donor materials, and the highly electronegative fluorine substituents at the IDT core enables lowering the LUMO energy and facilitates the use of the compound as electron acceptor, especially as NFA. The compounds according to the present invention are further characterized in that they comprise conjugated acyclic or cyclic electron-withdrawing groups (EWGs), such as ketone or dicyanomethylene groups, at the bridge positions. These EWGs enable effective stabilisation of the LUMO energy along with easy tuning of the energy levels. Moreover, compounds according to the present invention comprise an extended central polycyclic core, which leads to extension of the conjugation length, further delocalising the molecular orbitals as well as improving intermolecular interactions between molecules/chains via improved pi-pi stacking. All these factors can lead to more efficient charge transfer.

IDT small molecules (1) and (2) with a ketone or dicyanomethylene group as shown below were reported in *ACS Appl. Mater. Interfaces* 2017, 9, 8219-8232 and *J. Mater. Chem.*, 2010, 20, 7998-8004. However, these small molecules of the IDT-dione (1) were shown to only moderately lower the LUMO energies.

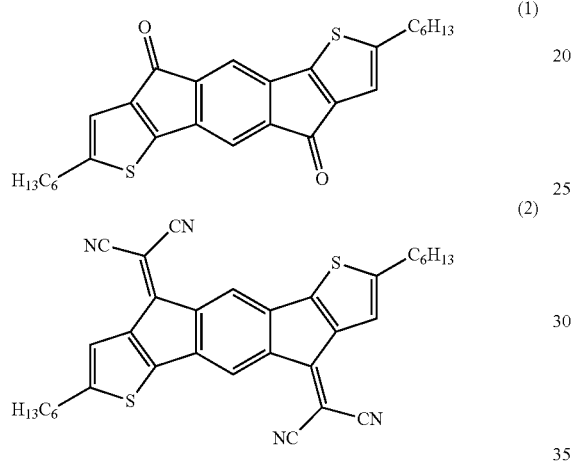
(1)
(2)

The compounds as disclosed and claimed hereinafter have not been disclosed or suggested in prior art.

SUMMARY

The invention relates to a compound comprising a divalent unit of formula I

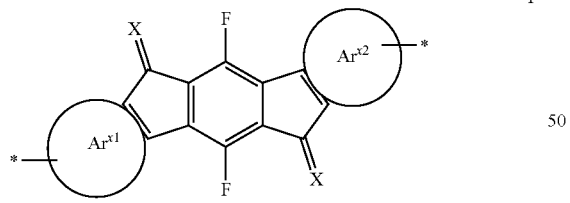
I wherein the individual radicals, independently of each other and on each occurrence identically or differently, have the following meanings X is selected from the group consisting of the following formulae, wherein Q denotes an sp$^2$ C atom that is attached to the indacene core in formula I via the C=C double bond

Xa

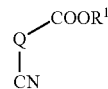
Xb

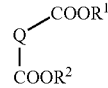
Xc

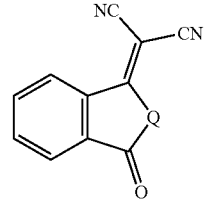
Xd

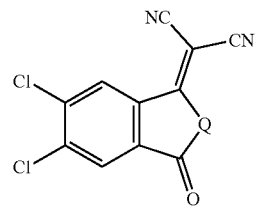
Xe

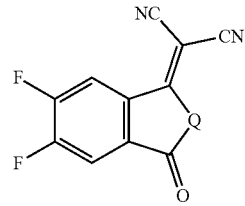
Xf

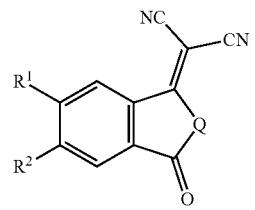
Xg

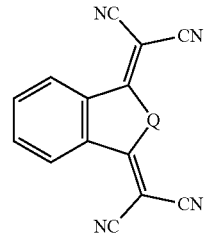
Xh

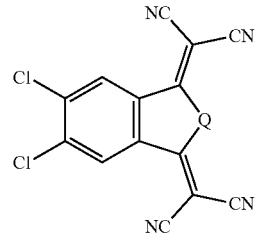
Xi

-continued

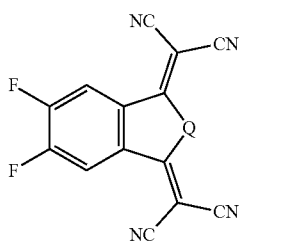

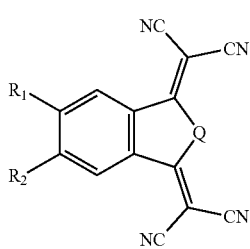

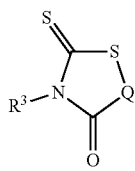

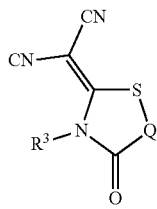

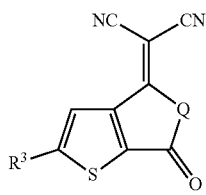

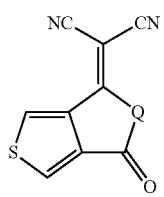

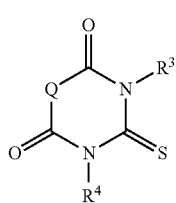

Ar$^{x1}$ is selected from the group consisting of the following formulae

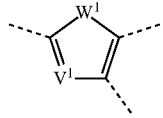
A1a

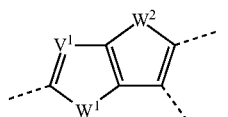
A1b

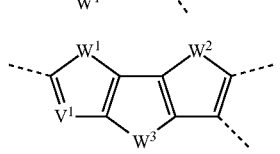
A1c

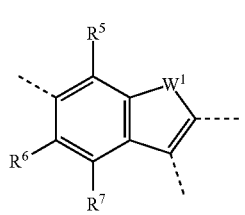
A1d

Ar$^{x2}$ is selected from the group consisting of the following formulae

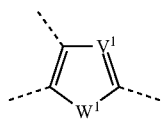
A2a

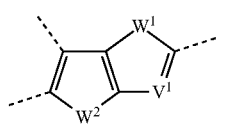
A2b

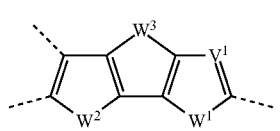
A2c

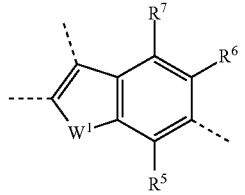
A2d

V$^1$ CR$^5$ or N,
W$^1$, W$^2$ S, O, Se or C=O,
W$^3$ S, O or NR$^0$,
R$^{1-7}$ H, F, Cl, CN, or straight-chain, branched or cyclic alkyl with 1 to 30, preferably 1 to 20, C atoms, in which one or more CH2 groups are optionally replaced by —O—, —S—, —C(=O)—, —C(=S)—, —C(=O)—O—, —O—C(=O)—, —NR$^0$—, —SiR$^0$R$^{00}$—, —CF$_2$—, —CR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, $Y^1$, $Y^2$ H, F, Cl or CN, L F, Cl, $-NO_2$, $-CN$, $-NC$, $-NCO$, $-NCS$, $-OCN$, $-SCN$, $R^0$, $OR^0$, $SR^0$, $-C(=O)X^0$, $-C(=O)R^0$, $-C(=O)-OR^0$, $-O-C(=O)-R^0$, $-NH_2$, $-NHR^0$, $-NR^0R^{00}$, $-C(=O)NHR^0$, $-C(=O)NR^0R^{00}$, $-SO_3R^0$, $-SO_2R^0$, $-OH$, $-NO_2$, $-CF_3$, $-SF_5$, or optionally substituted silyl, or carbyl or hydrocarbyl with 1 to 30, preferably 1 to 20 C atoms that is optionally substituted and optionally comprises one or more hetero atoms, preferably F, $-CN$, $R^0$, $-OR^0$, $-SR^0$, $-C(=O)-R^0$, $-C(=O)-OR^0$, $-O-C(=O)-R^0$, $-O-C(=O)-OR^0$, $-C(=O)-NHR^0$, or $-C(=O)-NR^0R^{00}$, $R^0$, $R^{00}$ H or straight-chain or branched alkyl with 1 to 20, preferably 1 to 12, C atoms that is optionally fluorinated, $X^0$ halogen, preferably F or Cl.

The invention further relates to the use of the units of formula I in or as repeating units in conjugated polymers.

The invention further relates to a compound according to the present invention which is a conjugated polymer comprising one or more repeating units of formula I.

The invention further relates to a compound according to the present invention which is a small molecule or oligomer comprising one or more units of formula I.

A compound comprising one or more units of formula I is hereinafter also referred to as "compound according to the (present) invention".

The invention further relates to a compound according to the present invention which is a monomer comprising a unit of formula I, optionally further comprising one or more additional arylene or heteroarylene units, and further comprising one or more, preferably two reactive groups on the benzene ring in ortho-position to the groups $X^1$ and $X^2$, wherein these reactive groups can be reacted to form a small molecule, oligomer or conjugated polymer as described above and below, preferably in an aryl-aryl coupling reaction.

The invention further relates to a compound according to the present invention which is a small molecule or oligomer comprising one or more units of formula I and further comprising one or more electron-withdrawing groups.

The invention further relates to novel synthesis methods for preparing compounds according to the present invention, and novel intermediates used therein.

The invention further relates to the use of compounds according to the present invention as semiconductor, either as electron acceptor or n-type semiconductor, or as electron donor or n-type semiconductor, preferably in a semiconducting material, an electronic or optoelectronic device, or a component of an electronic or optoelectronic device.

The invention further relates to the use of compounds according to the present invention as dyes or pigments.

The invention further relates to a composition comprising one or more compounds according to the present invention, and further comprising one or more compounds having one or more of a semiconducting, hole or electron transport, hole or electron blocking, insulating, binding, electrically conducting, photoconducting, photoactive or light emitting property.

The invention further relates to a composition comprising one or more compounds according to the present invention, and further comprising a binder, preferably an electrically inert binder, very preferably an electrically inert polymeric binder.

The invention further relates to a composition comprising a compound according to the present invention which is an electron donor or p-type semiconductor, and further comprising one or more electron acceptors or n-type semiconductors, preferably selected from fullerenes or substituted fullerenes, or from non-fullerene acceptors.

The invention further relates to a composition comprising a compound according to the present invention which is an electron acceptor or n-type semiconductor, and further comprising one or more electron donors or p-type semiconductors, preferably selected from conjugated polymers.

The invention further relates to a composition comprising one or more n-type semiconductors, at least one of which is a compound according to the present invention, and further comprising one or more p-type semiconductors.

The invention further relates to a composition comprising one or more n-type semiconductors, at least one of which is a compound according to the present invention, and at least one other of which is a fullerene or substituted fullerene, and further comprising one or more p-type semiconductors, preferably selected from conjugated polymers.

The invention further relates to a bulk heterojunction (BHJ) formed from a composition comprising a compound according to the present invention as electron acceptor or n-type semiconductor, and one or more compounds which are electron donor or p-type semiconductors, and are preferably selected from conjugated polymers.

The invention further relates to a bulk heterojunction (BHJ) formed from a composition comprising a compound according to the present invention as electron donor or p-type semiconductor, and one or more compounds which are electron acceptors or n-type semiconductors, and are preferably selected from fullerenes, substituted fullerenes or non-fullerene acceptors.

The invention further relates to the use of a compound according to the present invention or a composition as described above and below, as semiconducting, charge transporting, electrically conducting, photoconducting, photoactive or light emitting material.

The invention further relates to the use of a compound according to the present invention or a composition as described above and below, in an electronic or optoelectronic device, or in a component of such a device or in an assembly comprising such a device.

The invention further relates to a semiconducting, charge transporting, electrically conducting, photoconducting, photoactive or light emitting material, comprising a compound according to the present invention or a composition as described above and below.

The invention further relates to an electronic or optoelectronic device, or a component thereof, or an assembly comprising it, which comprises a compound according to the present invention or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising one or more compounds according to the present invention, or comprising a composition or semiconducting material as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells (PSC), laser diodes, Schottky diodes, photoconductors, photodetectors and thermoelectric devices.

Preferred devices are OFETs, OTFTs, OPVs, PSCs, OPDs and OLEDs, in particular OPDs and BHJ OPVs or inverted BHJ OPVs.

Further preferred is the use of a compound or composition according to the present invention as dye in a DSSC or a PSC. Further preferred is a DSSC or PSC comprising a compound or composition according to the present invention.

The component of the electronic or optoelectronic device includes, without limitation, charge injection layers, charge transport layers, interlayers, planarising layers, antistatic films, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

In addition the compounds according to the present invention and compositions as described above and below can be used as electrode materials in batteries, or in components or devices for detecting and discriminating DNA sequences.

Terms and Definitions

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5, very preferably ≥10, repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, like for example a unit of formula I or a polymer of formula III or IV or their subformulae, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^{31}$ or $R^{32}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$, or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/Mu$, wherein $M_n$ is the number average molecular weight and Mu is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, Sn, As, Te or Ge.

A carbyl or hydrocarbyl group comprising a chain of 3 or more C atoms may be linear, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be linear or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, P, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from F, Cl, —CN, —NC, —NCO, —NCS, —OCN, —SCN, —R$^0$, —OR$^0$, —SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O)NR$^0$R$^{00}$, —SO$_3$R$^0$, —SO$_2$R$^0$, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, wherein X$^0$ is halogen, preferably F or C, and R$^0$, R$^{00}$ denote H or linear or branched alkyl with 1 to 20, preferably 1 to 12 C atoms that is optionally fluorinated.

Preferably L is selected from F, —CN, R$^0$, —OR$^0$, —SR$^0$, —C(=O)—R$^0$, —C(=O)—OR$^0$, —O—C(=O)—R$^0$, —O—C(=O)—OR$^0$, —C(=O)—NHR$^0$ and —C(=O)—NR$^0$R$^{00}$.

Further preferably L is selected from F or alkyl, alkoxy, oxaalkyl, thioalkyl, fluoroalkyl, fluoroalkoxy, alkylcarbonyl, alkoxycarbonyl, with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

An arylalkyl or heteroarylalkyl group as referred to above and below preferably denotes —$(CH_2)_a$-aryl or —$(CH_2)_a$-heteroaryl, wherein a is an integer from 1 to 6, preferably 1, and "aryl" and "heteroaryl" have the meanings given above and below. A preferred arylalkyl group is benzyl which is optionally substituted by L.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred aryl and heteroaryl groups are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, 2,5-dithiophene-2',5'-diyl, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal $CH_2$ group is replaced by —O—, can be linear or branched. Particularly preferred linears have 2, 3, 4, 5, 6, 7, 8, 12 or 16 carbon atoms and accordingly denote preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are replaced by —CH=CH— can be linear or branched. It is preferably linear, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, can be linear. Particularly preferred linear groups are 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is linear and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxy-ethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be linear or branched. It is preferably linear and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably linear thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group can either be perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably C₆F₁₃, or partially fluorinated alkyl, preferably with 1 to 15 C atoms, in particular 1,1-difluoroalkyl, all of the aforementioned being linear or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 3,7-dimethyloctyl, 3,7,11-trimethyldodecyl, 2-propylpentyl, in particular 2-methylbutyl, 2-methylbutoxy, 2-methylpentoxy, 3-methyl-pentoxy, 2-ethyl-hexoxy, 2-butyloctoxyo, 2-hexyldecoxy, 2-octyldodecoxy, 3,7-dimethyloctoxy, 3,7,11-trimethyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloro-propionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoromethyloctyloxy for example. Very preferred are 2-methylbutyl, 2-ethylhexyl, 2-butyloctyl, 2-hexyldecyl, 2-octyldodecyl, 3,7-dimethyloctyl, 3,7,11-trimethyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the substituents on an aryl or heteroaryl ring are independently of each other selected from primary, secondary or tertiary alkyl, alkoxy, oxaalkyl, thioalkyl, alkylcarbonyl or alkoxycarbonyl with 1 to 30 C atoms, wherein one or more H atoms are each optionally replaced by F, or aryl, aryloxy, heteroaryl or heteroaryloxy that is optionally alkylated, alkoxylated, alkylthiolated or esterified and has 4 to 30, preferably 5 to 20, ring atoms. Further preferred substituents are selected from the group consisting of the following formulae

SUB1

RSub₁

SUB2

RSub₁  RSub₂

SUB3

RSub₂
RSub₁

SUB4

RSub₁  RSub₂

SUB5

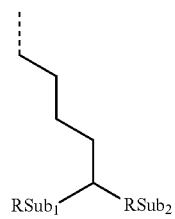

SUB6

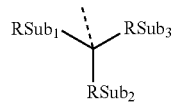

SUB7

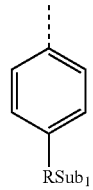

SUB8

RSub₁

SUB9

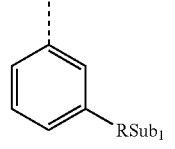

SUB10

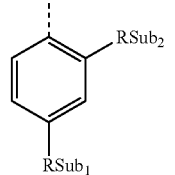

SUB11

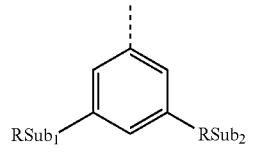

SUB12

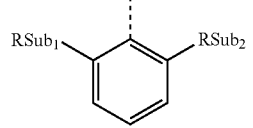

SUB13

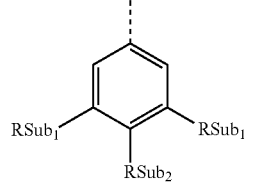

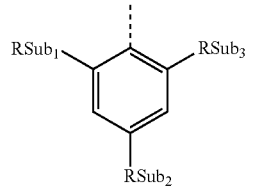

-continued

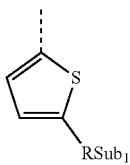
SUB14

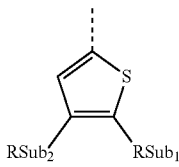
SUB15

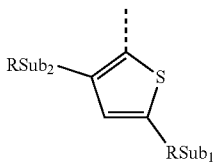
SUB16

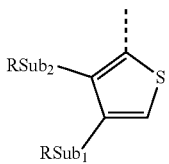
SUB17

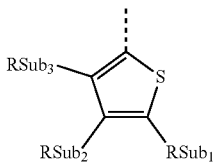
SUB18 wherein $RSub_{1-3}$ each denote L as defined above and below and where at least, preferably all, of $RSub_{1-3}$ is alkyl, alkoxy, oxaalkyl, thioalkyl, alkylcarbonyl or alkoxycarbonyl with up to 24 C atoms, preferably up to 20 C atoms, that is optionally fluorinated, and wherein the dashed line denotes the link to the ring to which these groups are attached. Very preferred among these substituents are those wherein all $RSub_{1-3}$ subgroups are identical.

As used herein, if an aryl(oxy) or heteroaryl(oxy) group is "alkylated or alkoxylated", this means that it is substituted with one or more alkyl or alkoxy groups having from 1 to 24 C-atoms and being straight-chain or branched and wherein one or more H atoms are each optionally substituted by an F atom.

Above and below, $Y^1$ and $Y^2$ are independently of each other H, F, Cl or CN.

As used herein, —CO—, —C(=O)— and —C(O)— will be understood to mean a carbonyl group, i.e. a group having the structure

As used herein, $C=CR^1R^2$ will be understood to mean a group having the structure

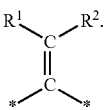

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer or an intermediate is preferably Br or I.

Above and below, the term "mirror image" means a moiety that can be obtained from another moiety by flipping it vertically or horizontally across an external symmetry plane or a symmetry plane extending through the moiety. For example the moiety

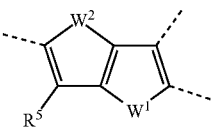

also includes the mirror images

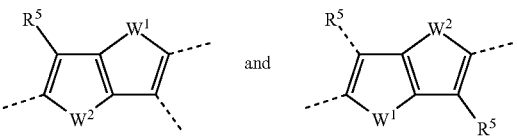

DETAILED DESCRIPTION

The compounds of the present invention are easy to synthesize and exhibit advantageous properties. They show good processability for the device manufacture process, high solubility in organic solvents, and are especially suitable for large scale production using solution processing methods.

Co-polymers derived from monomers of the present invention and electron donor/acceptor monomers show low bandgaps, high charge carrier mobilities, high external quantum efficiencies in BHJ solar cells, good morphology when used in p/n-type blends e.g. with poly(3-hexylthiophene), high oxidative stability, a long lifetime in electronic devices, and are promising materials for organic electronic OE devices, especially for OPV devices with high power conversion efficiency.

The compounds of the present invention are especially suitable as both p-type and n-type semiconductors, depending on the nature of the co-monomer or π-units cross-coupled to extend the conjugation, for the preparation of blends of p-type and n-type semiconductors which are suitable for use in BHJ photovoltaic devices.

The compounds according to the present invention are further suitable to replace the fullerene compounds that have hitherto been used as n-type semiconductor in OPV or OPD devices.

Besides, the compounds according to the present invention show the following advantageous properties:
  i) Combination of the IDT core with the highly electronegative fluoro substituents enables lowering the LUMO energy and facilitates the use of the compound as electron acceptor.

ii) The conjugated acyclic or cyclic electron-withdrawing groups (EWGs), X in formula I enable effective stabilisation of the LUMO energy along with easy tuning of the energy.

iii) The aryl or heteroaryl groups $Ar^1$ and $Ar^2$ fused to the IDT core lead to an extension of the conjugation length, further delocalising the molecular orbitals as well as improving intermolecular interactions between molecules/chains via improved pi-pi stacking.

iv) Combination of the factors i-iii leads to more efficient charge transfer.

The synthesis of the compounds according to the present invention can be achieved based on methods that are known to the skilled person and described in the literature, as will be further illustrated herein.

In a preferred embodiment of the present invention, in the units of formula I and its subformulae and the compounds comprising them $R^1$ and $R^2$ are selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the units of formula I and its subformulae and the compounds comprising them $R^1$ and $R^2$ are selected from mono- or polycyclic aryl or heteroaryl, each of which is optionally substituted with one or more groups L as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, most preferably from formulae SUB7-SUB18 above.

In the units of formula I and its subformulae and the compounds comprising them $R^3$ and $R^4$ are preferably H.

In another preferred embodiment of the present invention, in the units of formula I and its subformulae and the compounds comprising them $R^3$ and $R^4$ are different from H.

In another preferred embodiment of the present invention, in the units of formula I and its subformulae and the compounds comprising them $R^3$ and $R^4$ are selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the units of formula I and its subformulae and the compounds comprising them $R^3$ and $R^4$ are selected from mono- or polycyclic aryl or heteroaryl, each of which is optionally substituted with one or more groups L as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from formulae SUB14-SUB18 above.

In a preferred embodiment of the present invention, in the units of formula I and its subformulae and the compounds comprising them $R^{5-8}$ are H.

In another preferred embodiment of the present invention, in the units of formula I and its subformulae and the compounds comprising them at least one of $R^{5-8}$ is different from H.

In a preferred embodiment of the present invention, in the units of formula I and its subformulae and the compounds comprising them $R^{5-8}$, when being different from H, are each independently selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the units of formula I and its subformulae and the compounds comprising them $R^{5-8}$, when being different from H, are each independently selected are selected from mono- or polycyclic aryl or heteroaryl, each of which is optionally substituted with one or more groups L as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from formulae SUB14-SUB18 above.

Preferred aryl and heteroaryl groups $R^{1-8}$, when being different from H, are each independently selected from the group consisting of the following formulae

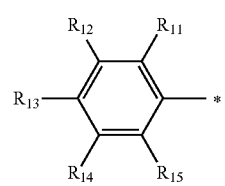

C1

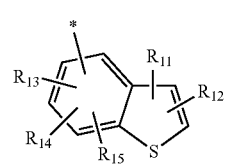

C2

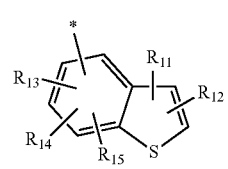

C3

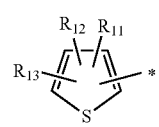

C4

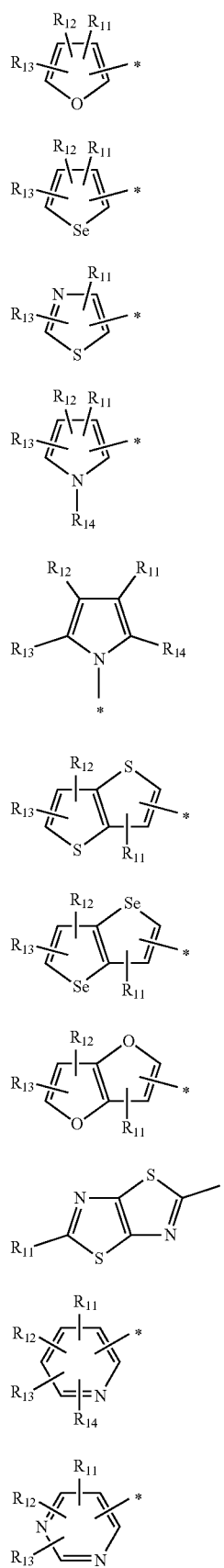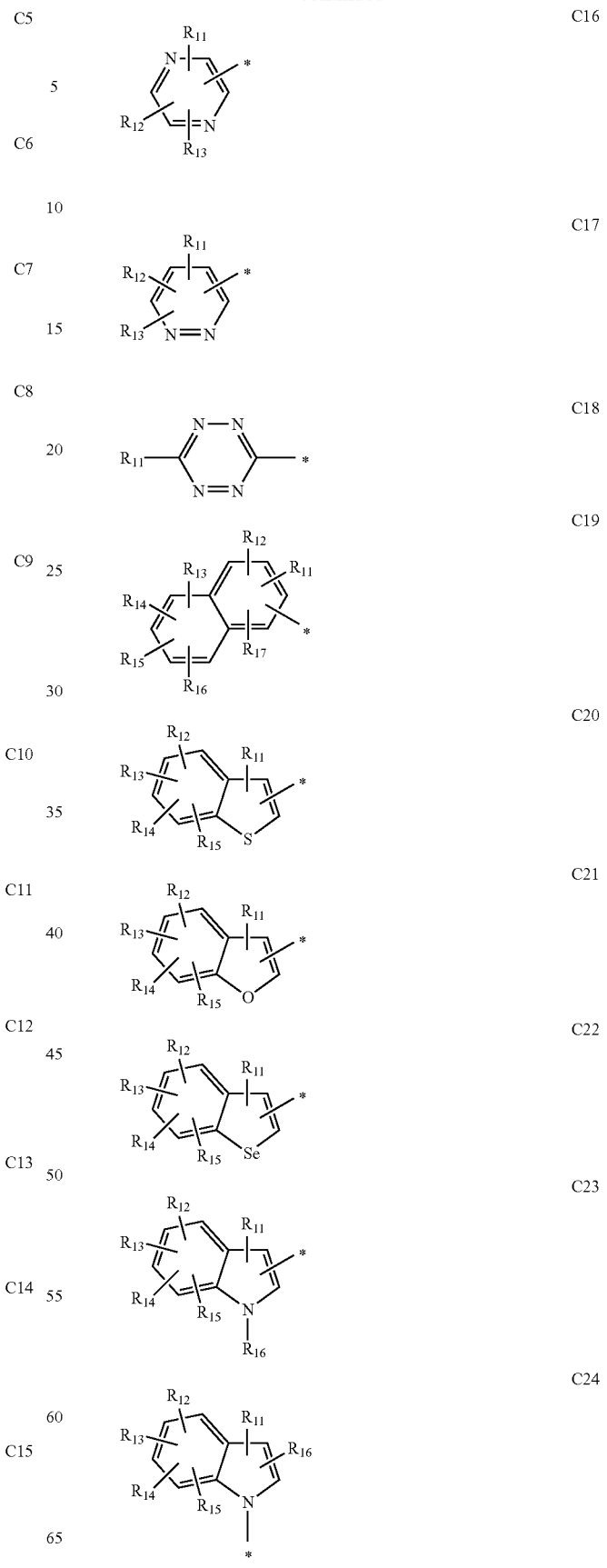

-continued

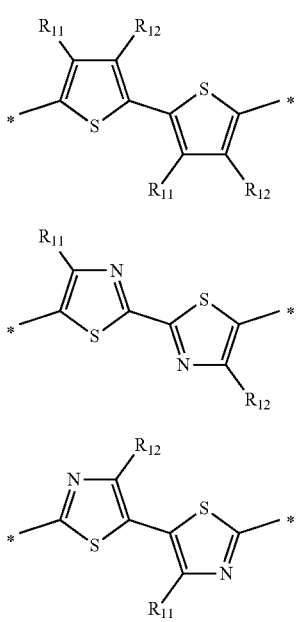

C25

C26

C27 wherein $R^{11-17}$, independently of each other, and on each occurrence identically or differently, denote H or have one of the meanings given for L, preferably for $R^7$, as in formula I or one of their preferred meanings as given above and below.

Very preferred aryl and heteroaryl groups $R^{1-8}$, when being different from H, are each independently selected from the group consisting of the following formulae

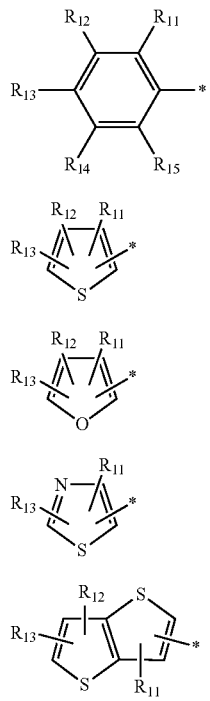

C1-1

C4-1

C5-1

C7-1

C10-1 wherein $R^{11-5}$ are as defined above. Most preferred aryl and heteroaryl groups $R^{1-9}$ are each independently selected from formulae SUB7-SUB16 as defined above.

In another preferred embodiment one or more of $R^{1-8}$ denote a straight-chain, branched or cyclic alkyl group with 1 to 50, preferably 2 to 50, very preferably 2 to 30, more preferably 2 to 24, most preferably 2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms and very preferably is selected from formulae SUB1-6.

Further preferred cationic groups are selected from the group consisting of the following formulae

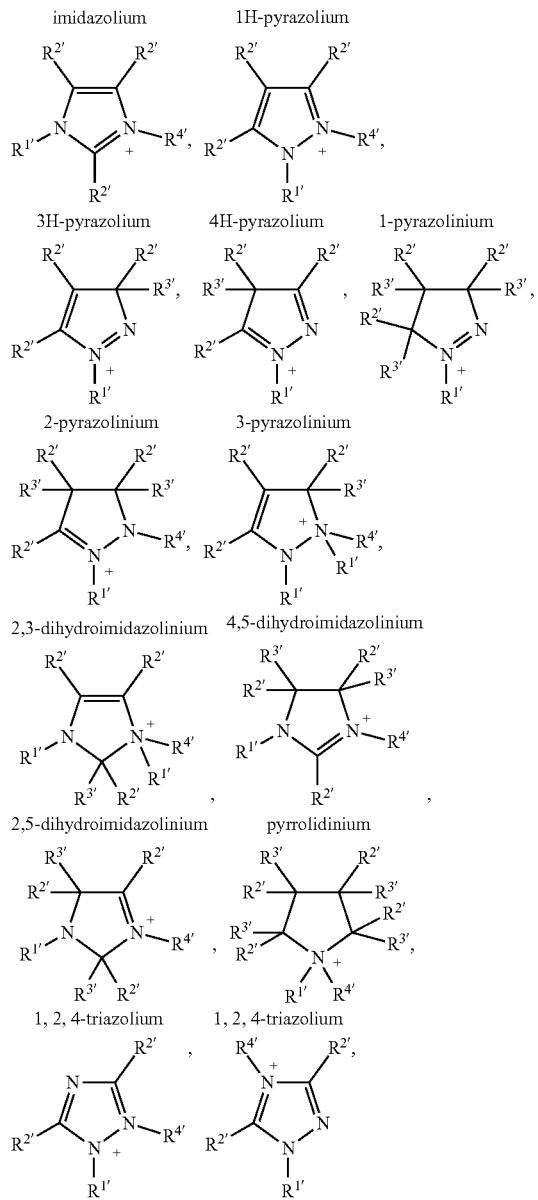

1, 2, 3-triazolium   1, 2, 3-triazolium

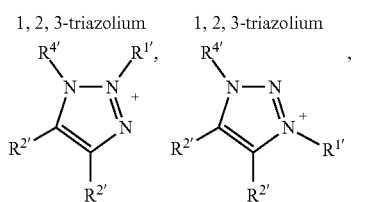

pyridinium   pyridazinium

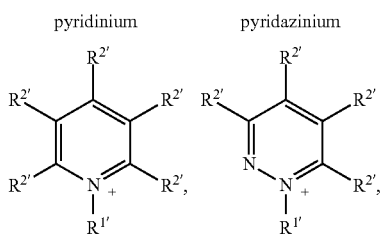

pyrimidinium   piperidinium

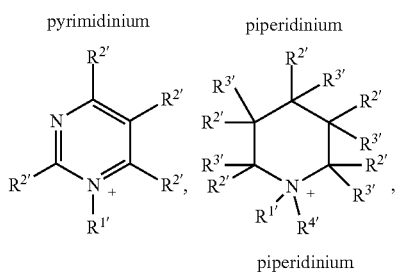

morpholinium   piperidinium

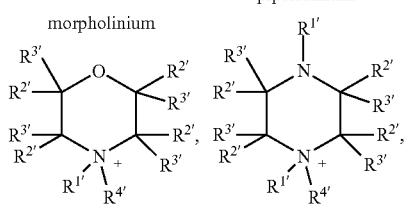

piperazinium   pyrazinium

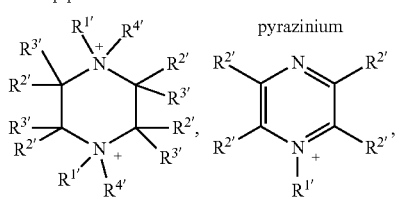

thiazolium   oxazolium

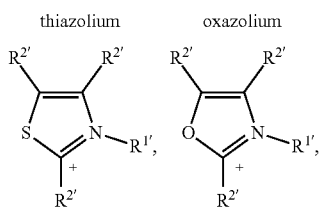

indolium   quinolinium

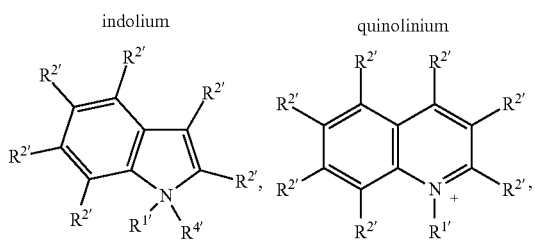

isoquinolinium

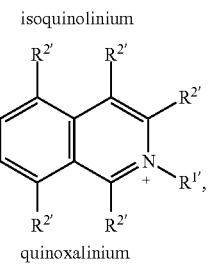

quinoxalinium

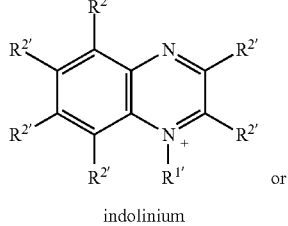 or indolinium

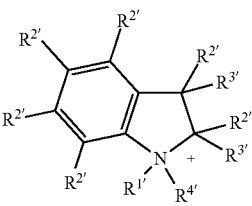

wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents L as defined above, or denote a link to the respective group $R^{1-9}$.

In the above cationic groups of the above-mentioned formulae any one of the groups $R^{1'}$, $R^{2'}$, $R^{3'}$ and $R^{4'}$ (if they replace a $CH_3$ group) can denote a link to the respective group $R^{1-10}$, or two neighbored groups $R^{1'}$, $R^{2'}$, $R^{3'}$ or $R^{4'}$ (if they replace a $CH_2$ group) can denote a link to the respective group $R^1$.

The anionic group is preferably selected from the group consisting of borate, imide, phosphate, sulfonate, sulfate, succinate, naphthenate or carboxylate, very preferably from phosphate, sulfonate or carboxylate.

In the units of formula I X is preferably selected from the group consisting of formulae Xa, Xb, Xf, Xg, Xm and Xq.

In the units of formula I $Ar^{x1}$ is preferably selected from formulae A1a and A1c, more preferably from formula A1a, and $Ar^{x2}$ is preferably selected from formulae A2a and A2c, more preferably from formula A2a.

Preferred groups $Ar^{x1}$ in the units of formula I are selected from the following formulae and their mirror images A1a1

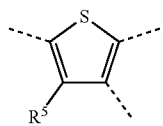

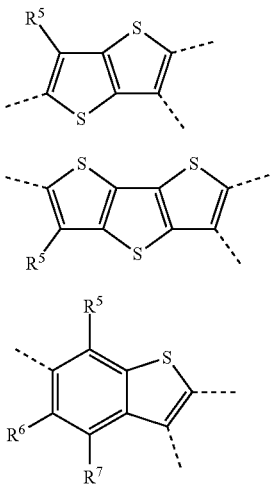

wherein R$^{5-7}$ have the meanings given above and below.

Preferred groups Ar$^{x2}$ in the units of formula I are selected from the following formulae and their mirror images

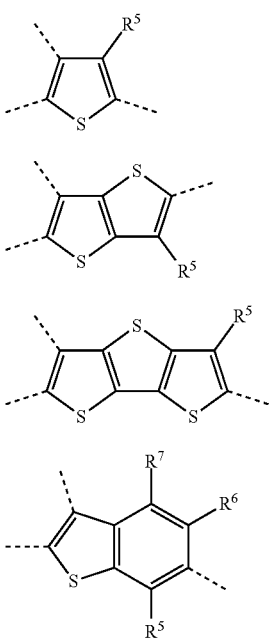

wherein R$^{5-7}$ have the meanings given above and below.

In the units of formula I Ar$^{x1}$ is preferably selected from formulae A1a1 and A1c1, more preferably from formula A1a1, and Ar$^{x2}$ is preferably selected from formulae A2a1 and A2c1, more preferably from formula A2a1.

The compounds according to the present invention include small molecules, monomers, oligomers and polymers.

A first preferred embodiment of the present invention relates to a small molecule comprising one or more units of formula I, which is preferably selected from formulae S1

$$T^1\text{-}(Ar^{13})_{c1}\text{—}[(Ar^{11})_{a1}\text{—}U\text{—}(Ar^{12})_{b1}\text{-}]_{e1}(Ar^{14})_{d1}\text{-}T^2 \qquad S1$$

wherein the individual radicals, independently of each other and on each occurrence identically or differently, have the following meanings U a unit of formula I or its preferred embodiments as defined above and below, Ar$^{11-14}$ arylene or heteroarylene that has 5 to 20 ring atoms, is mono- or polycyclic, does optionally contain fused rings, is unsubstituted or substituted by one or more identical or different groups R$^S$, and is different from formula I, or CY$^1$=CY$^2$— or —C≡C—, T$^1$, T$^2$ one of the meanings given for R$^1$ in formula I, R$^S$ F, Cl, CN, or linear, branched or cyclic alkyl with 1 to 30, preferably 1 to 20, C atoms, in which one or more CH$_2$ groups are optionally replaced by —O—, —S—, —C(=O)—, —C(=S)—, —C(=O)—O—, —O—C(=O)—, —NR$^0$—, —SiR$^0$R$^{00}$—, —CF$_2$—, —CR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or R$^S$ is aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L as defined above, X$^0$ halogen, preferably F or Cl, Y$^1$, Y$^2$ H, F, Cl or CN, R$^0$, R$^{00}$ H or linear or branched alkyl with 1 to 20, preferably 1 to 12, C atoms that is optionally fluorinated, a1-d1 0, 1, 2 or 3, e1 1, 2 or 3.

In a preferred embodiment of the present invention the groups T$^1$ and T$^2$ in formula S1 and its subformulae are each independently selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention the groups T$^1$ and T$^2$ in formula S1 and its subformulae are each independently selected from mono- or polycyclic aryl or heteroaryl, each of which is optionally substituted with one or more groups L as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from formulae SUB14-SUB18 above.

Further preferred aryl and heteroaryl groups T$^1$ and T$^2$ are each independently selected from the group consisting of formulae C1 to C27 as defined above, very preferably from the group consisting of formulae C1-1, C1-4, C1-5, C1-7 and C1-10 as defined above.

Preferred groups Ar$^{11}$, Ar$^{12}$, Ar$^{13}$ and Ar$^{14}$ in formula S1 are each independently and on each occurrence identically or differently selected from arylene or heteroarylene which has from 5 to 20 ring atoms, which is mono- or polycyclic, which optionally contains fused rings, and which is unsubstituted or substituted by one or more identical or different groups L, or from —CY$^1$=CY$^2$—.

Very preferred groups $Ar^{11}$, $Ar^{12}$, $Ar^{13}$ and $Ar^{14}$ in formula S1 are each independently and on each occurrence identically or differently selected from the following formulae and their mirror images:

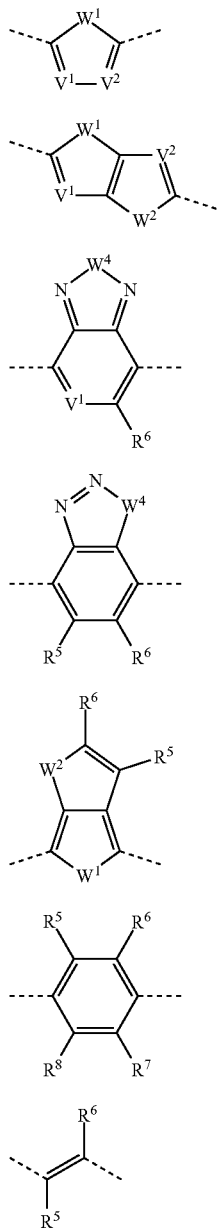

AR1
AR2
AR3
AR4
AR5
AR6
AR7

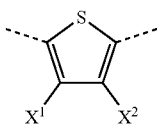 AR1-1

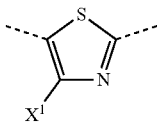 AR1-2

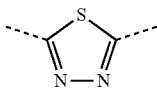 AR1-3

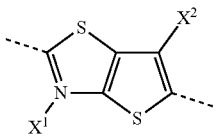 AR2-1

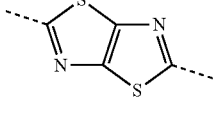 AR2-2

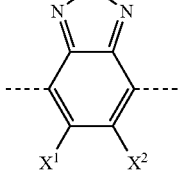 AR3-1

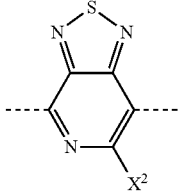 AR3-2

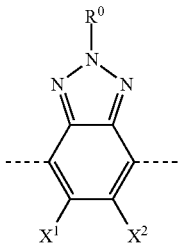 AR3-3

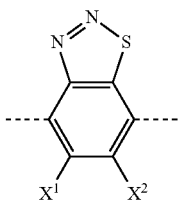 AR4-1 wherein the individual radicals, independently of each other and on each occurrence identically or differently, have the following meanings $V^2$ $CR^6$ or N,
$W^4$ S, O, Se, $NR^0$ or C=O,
$R^8$ one of the meanings of $R^5$,
and $V^1$, $W^1$, $W^2$, $R^0$, $R^{5-7}$ are as defined above and below.

More preferred groups $Ar^{11}$, $Ar^{12}$, $Ar^{13}$ and $Ar^{14}$ in formula S1 are each independently, and on each occurrence identically or differently, selected from the following formulae and their mirror images AR5-1
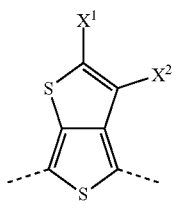

AR6-1
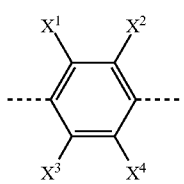

AR7-1
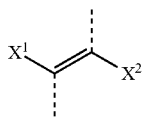

wherein $X^1$, $X^2$, $X^3$ and $X^4$ have one of the meanings given for $R^1$ above and below, and preferably denote H, F, Cl, —CN, $R^0$, $OR^0$ or $C(=O)OR^0$, and $R^0$ is as defined above and below.

Preferred formulae AR1-1 to AR7-1 are those containing at least one, preferably one, two or four substituents $X^{1-4}$ selected from F and Cl, very preferably F.

In formula AR6-1 preferably one or two, very preferably all of $X^1$-4 are F.

Preferred groups $Ar^{11}$, $Ar^{12}$, $Ar^{13}$ and $Ar^{14}$ are selected from formulae AR1, AR2, AR3, AR5 and AR7. Very preferred groups $Ar^{11}$, $Ar^{12}$, $Ar^{13}$ and $Ar^{14}$ are selected from formulae AR1-1, AR1-2, AR2-1, AR3-1, AR3-2, AR5-1 and AR7-1, most preferably from formulae AR1-1, AR2-1, AR3-1 and AR7-1.

Very preferred compounds of formula S1 are selected from the group consisting of the following subformulae S1-1
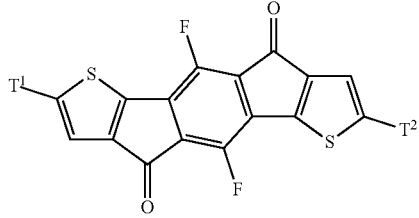

S1-2
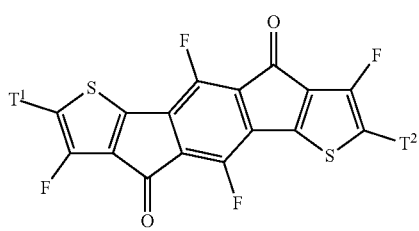

S1-3
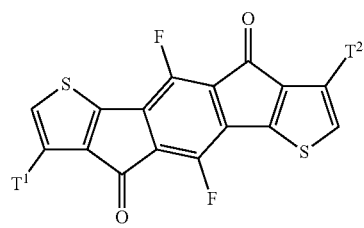

S1-4
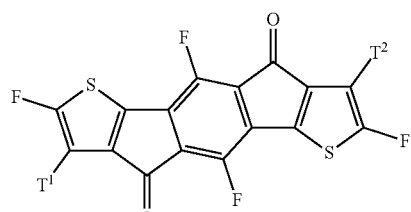

S1-5
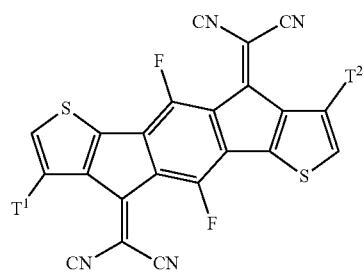

S1-6
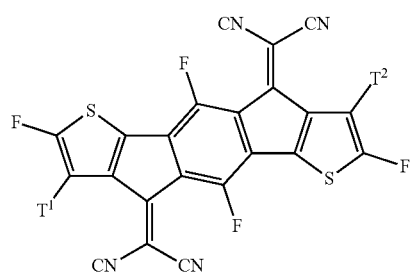

S1-7
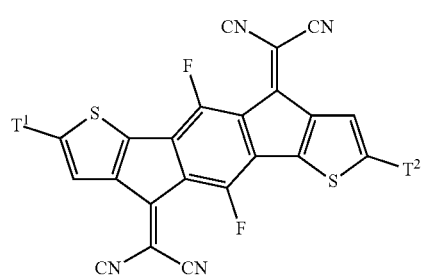

S1-8
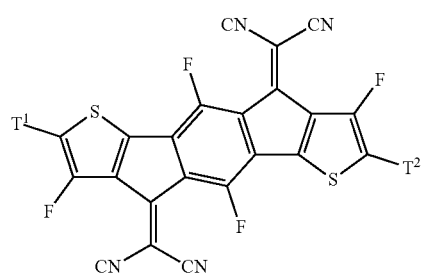

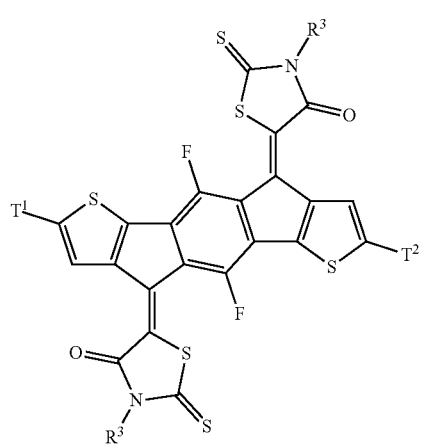
S1-9
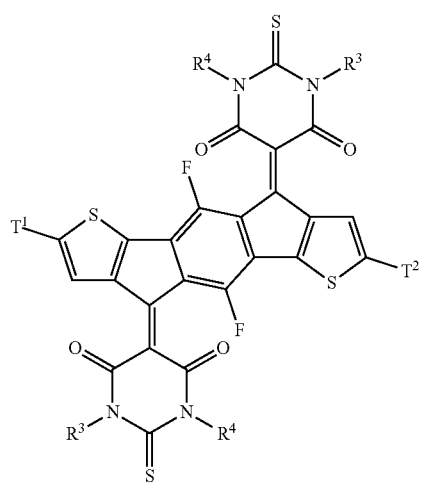
S1-10
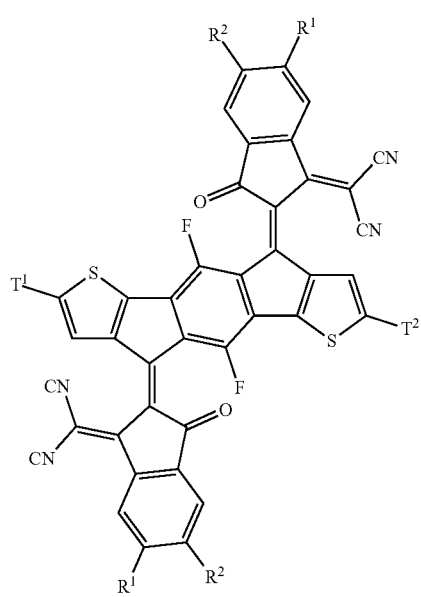
S1-11
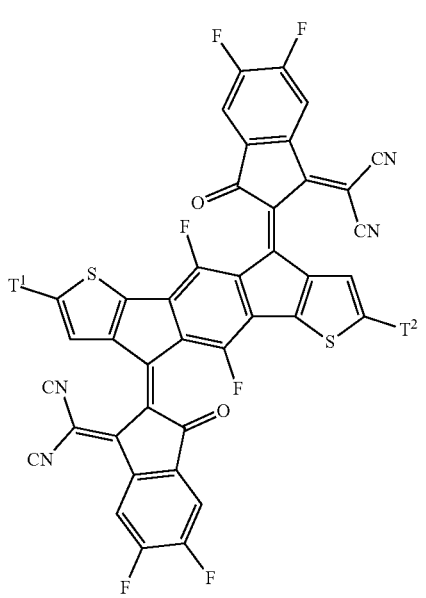
S1-12
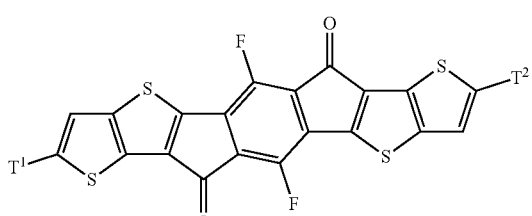
S1-13
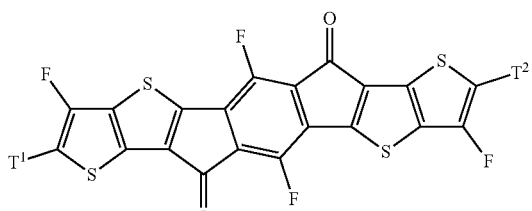
S1-14
S1-15

S1-16
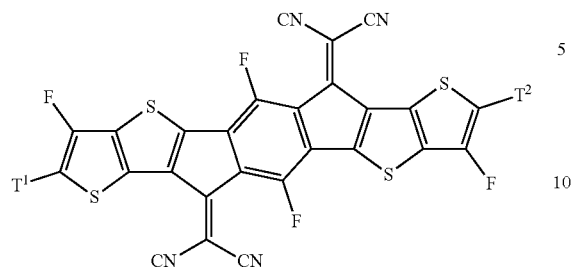
S1-17
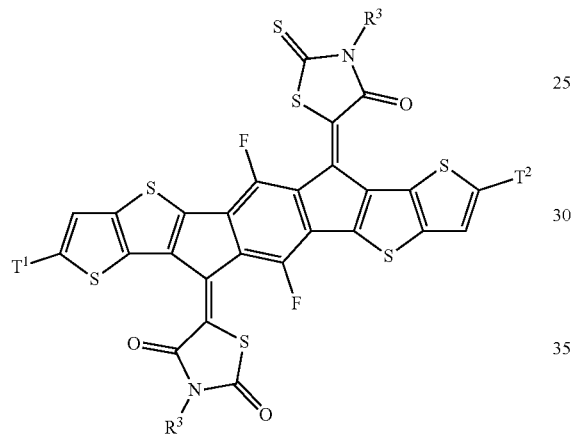
S1-18
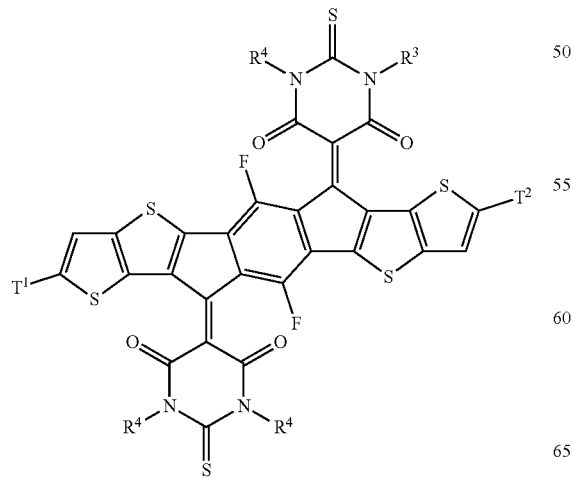
S1-19
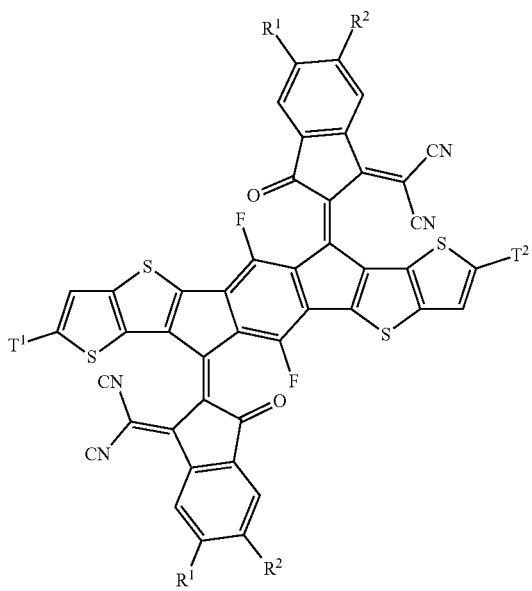
S1-20
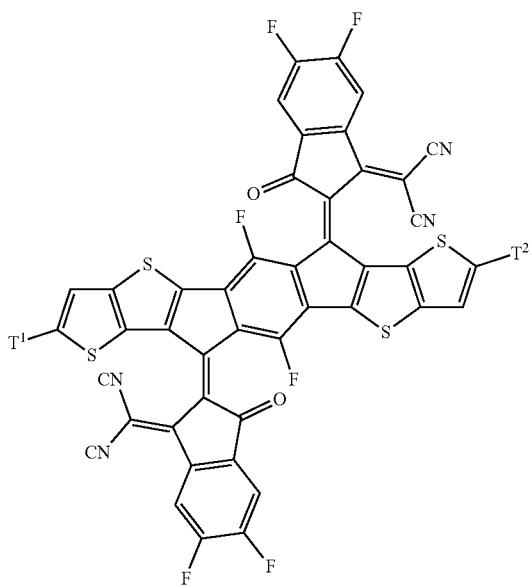
S1-21
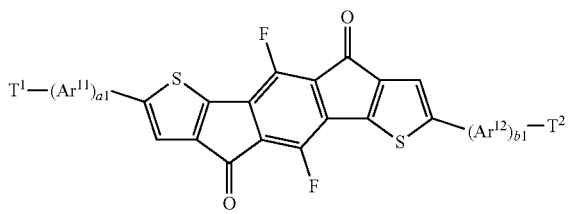

-continued
S1-22
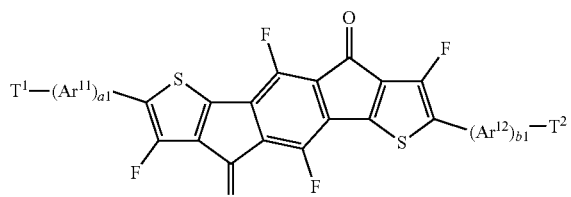
S1-23
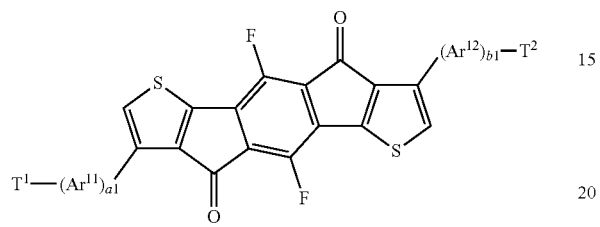
S1-24
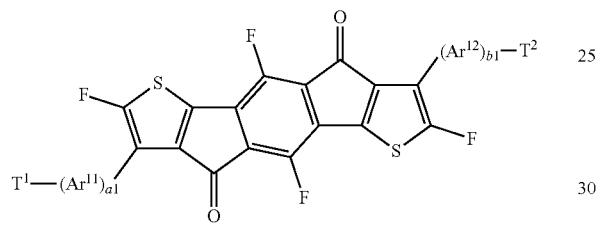
S1-25
S1-26
S1-27
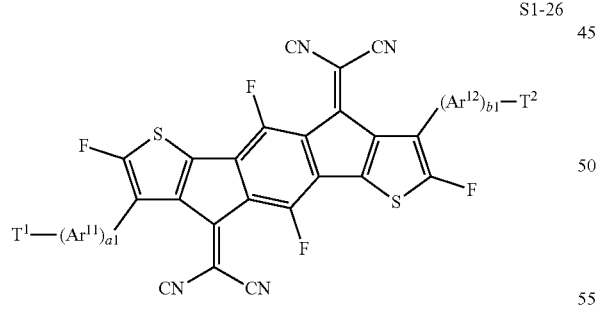
S1-28
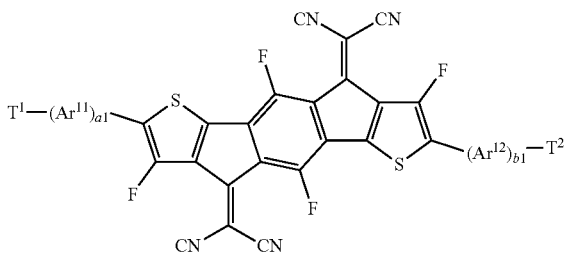
S1-29
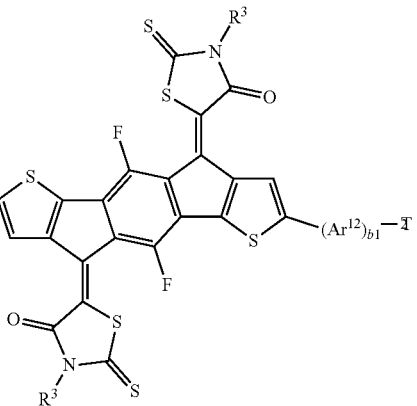
S1-30
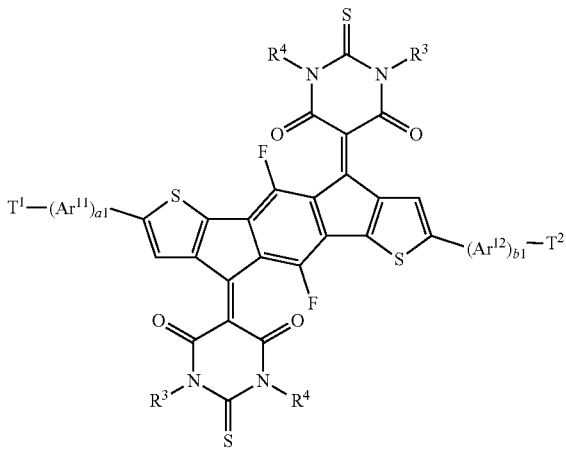

S1-31
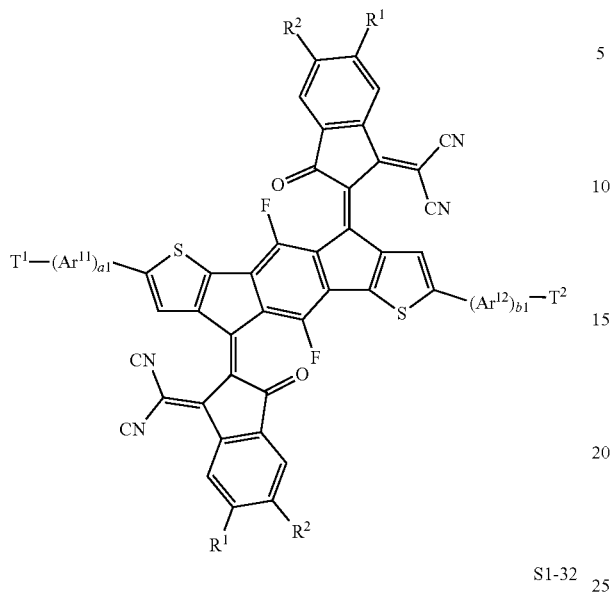
S1-32
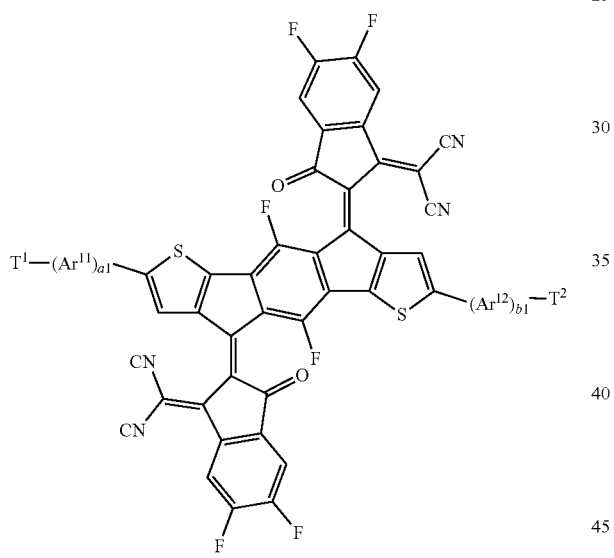
S1-33
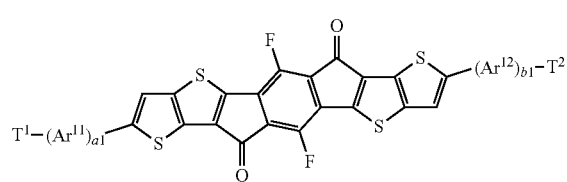
S1-34
S1-35
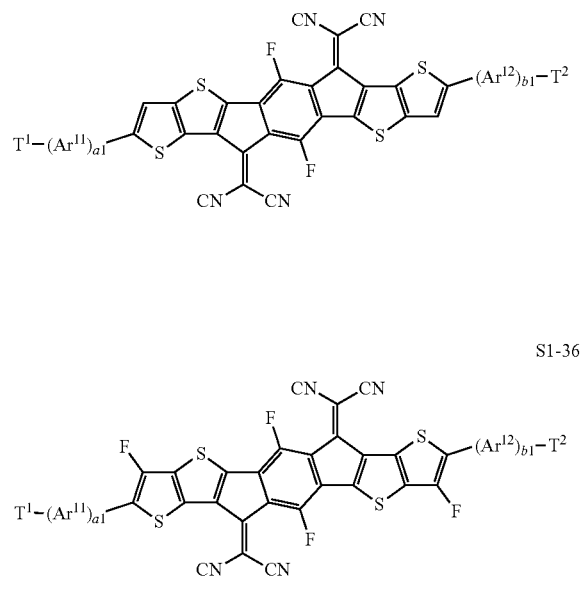
S1-36
S1-37
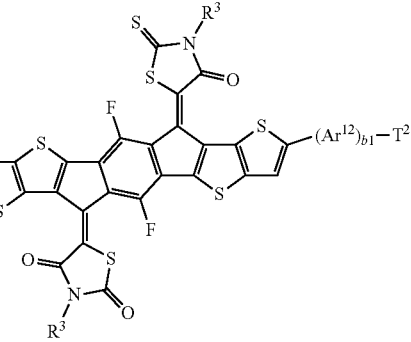
S1-38
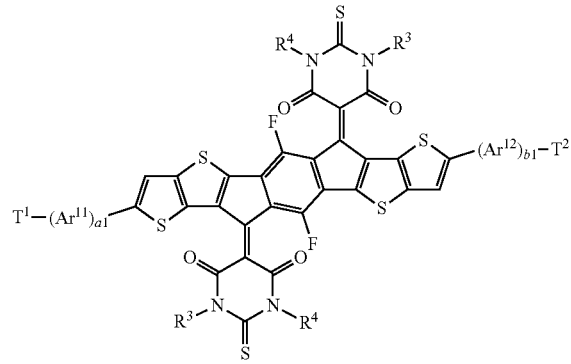

-continued

S1-39

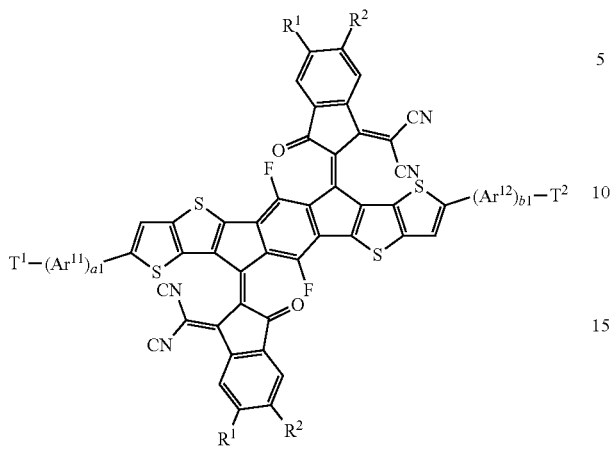

S1-40

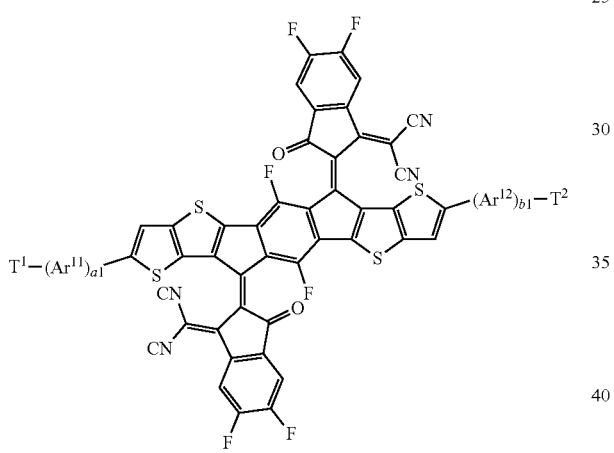

wherein $Ar^{11}$, $Ar^{12}$, $R^1$, $R^2$, $R^3$, $R^4$, $T^1$ and $T^2$ have independently of each other one of the meanings given in formula I and S1 or one of their preferred meanings as given above and below, a1 is 1 or 2 and b1 is 0, 1 or 2.

Further preferred compounds of formula S1 and S1-1 to S1-40 are selected from the following preferred embodiments, including any combination thereof:
  e1 is 1,
  a1 and b1 are 0, 1 or 2, and c1, d1 are 0,
  a1 is 1 or 2 and b1 is 0,
  a1 is 1 or 2 and b1 is 1 or 2,
  a1=b1=c1=d1=0,
  X is selected from the group consisting of formulae Xa, Xb, Xf, Xg, Xm and Xq,
  $Ar^{11-14}$ are selected from formulae AR1-1, AR1-2, AR2-1, AR3-1, AR3-2, AR5-1 and AR7-1,
  one or more of $R^{1-8}$ are different from H,
  $R^{1-8}$, when being different from H, are each independently selected from H, F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated, or alkyl or alkoxy having 1 to 12 C atoms that is optionally fluorinated,
  $R^{1-8}$, when being different from H, are each independently selected from aryl or heteroaryl, each of which is optionally substituted with one or more groups L as defined in formula I and has 4 to 30 ring atoms, preferably from phenyl that is optionally substituted, preferably in 4-position, or in 2,4-positions, or in 2,4,6-positions or in 3,5-positions, with alkyl or alkoxy having 1 to 20 C atoms, preferably 1 to 16 C atoms, very preferably from 4-alkylphenyl wherein alkyl is C1-16 alkyl, most preferably 4-methylphenyl, 4-hexylphenyl, 4-octylphenyl or 4-dodecylphenyl, or from 4-alkoxyphenyl wherein alkoxy is C1-16 alkoxy, most preferably 4-hexyloxyphenyl, 4-octyloxyphenyl or 4-dodecyloxyphenyl, or from 2,4-dialkylphenyl wherein alkyl is C1-16 alkyl, most preferably 2,4-dihexylphenyl or 2,4-dioctylphenyl, or from 2,4-dialkoxyphenyl wherein alkoxy is C1-16 alkoxy, most preferably 2,4-dihexyloxyphenyl or 2,4-dioctyloxyphenyl, or from 3,5-dialkylphenyl wherein alkyl is C1-16 alkyl, most preferably 3,5-dihexylphenyl or 3,5-dioctylphenyl, or from 3,5-dialkoxyphenyl wherein alkoxy is C1-16 alkoxy, most preferably 3,5-dihexyloxyphenyl or 3,5-dioctyloxyphenyl, or from 2,4,6-trialkylphenyl wherein alkyl is C1-16 alkyl, most preferably 2,4,6-trihexylphenyl or 2,4,6-trioctylphenyl, or from 2,4,6-trialkoxyphenyl wherein alkoxy is C1-16 alkoxy, most preferably 2,4,6-trihexyloxyphenyl or 2,4,6-trioctyloxyphenyl, or from 4-thioalkylphenyl wherein thioalkyl is C1-16 thioalkyl, most preferably 4-thiohexylphenyl, 4-thiooctylphenyl or 4-thiododecylphenyl, or from 2,4-dithioalkylphenyl wherein thioalkyl is C1-16 thioalkyl, most preferably 2,4-dithiohexylphenyl or 2,4-dithiooctylphenyl, or from 3,5-dithioalkylphenyl wherein thioalkyl is C1-16 thioalkyl, most preferably 3,5-dithiohexylphenyl or 3,5-dithiooctylphenyl, or from 2,4,6-trithioalkylphenyl wherein thioalkyl is C1-16 thioalkyl, most preferably 2,4,6-trithiohexylphenyl or 2,4,6-trithiooctylphenyl,
  $T^1$ and $T^2$ are each independently selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 30, preferably 1 to 20 C atoms and is unsubstituted or substituted by one or more F atoms, most preferably from F, Cl or formulae SUB1-SUB6 above,
  $T^1$ and $T^2$ are each independently selected from straight-chain or branched alkyl or alkoxy having 1 to 12 C atoms that is unsubstituted or substituted by one or more F atoms,
  $T^1$ and $T^2$ are each independently selected from mono- or polycyclic aryl or heteroaryl, each of which is optionally substituted with one or more groups L as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16

C atoms, more preferably from formulae SUB7-SUB18 above, most preferably from formulae SUB14-SUB18 above.

A second preferred embodiment of the present invention relates to a conjugated polymer comprising one or more repeating units of formula I. Preferably the conjugated polymer according to this preferred embodiment further comprises one or more arylene or heteroarylene units that have from 5 to 20 ring atoms, are mono- or polycyclic, optionally contains fused rings, and are unsubstituted or substituted by one or more identical or different groups L, preferably by one or more identical or different groups $R^S$, as defined above and below.

Preferably the conjugated polymer according to this preferred embodiment comprises, preferably consists of, one or more repeating units of formula II1 or II2, and optionally one or more repeating units of formula II3:

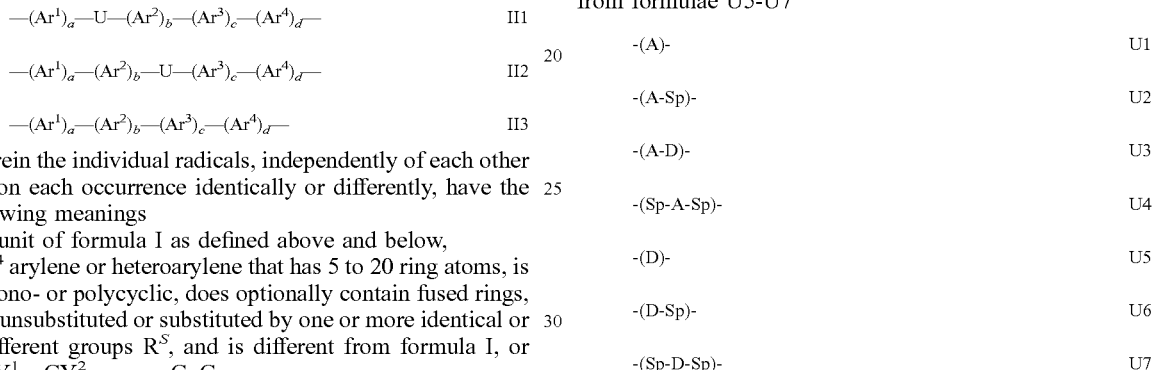

wherein the individual radicals, independently of each other and on each occurrence identically or differently, have the following meanings U a unit of formula I as defined above and below, $Ar^{1-4}$ arylene or heteroarylene that has 5 to 20 ring atoms, is mono- or polycyclic, does optionally contain fused rings, is unsubstituted or substituted by one or more identical or different groups $R^S$, and is different from formula I, or $CY^1=CY^2$— or —C≡C—, $R^S$ F, Cl, CN, or linear, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —NR°—, —SiR°R°°—, —CF₂—, —CR°=CR°°—, —CY¹=CY²— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or $R^S$ is aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L as defined above, $X^0$ halogen, preferably F or Cl, $Y^1$, $Y^2$ H, F, Cl or CN, $R^°$, $R^{°°}$ H or linear or branched alkyl with 1 to 20, preferably 1 to 12, C atoms that is optionally fluorinated, a, b, c, d 0 or 1, wherein in formula II3 a+b+c+d≥1.

Preferably the conjugated polymer comprises one or more repeating units of formula II1 or II2 wherein a+b+c+d≥1.

Further preferably the conjugated polymer comprises one or more repeating units of formula II1 wherein b=1 and a=c=d=0 and one or more repeating units of formula II3 wherein a=b=1 and c=d=0.

Further preferably the conjugated polymer comprises two or more distinct repeating units of formula II1 wherein b=1 and a=c=d=0.

Further preferably at least one of $Ar^1$, $Ar^2$, $Ar^3$ and $Ar^4$ is an arylene or heteroarylene group as being defined in formula II1 and having electron donor property.

Very preferably the conjugated polymer comprises at least one electron donating unit ("donor unit") and at least one electron accepting unit ("acceptor unit"), and optionally at least one spacer unit separating a donor unit from an acceptor unit, wherein each donor and acceptor units is directly connected to another donor or acceptor unit or to a spacer unit, and wherein all of the donor, acceptor and spacer units are selected from arylene or heteroarylene that has from 5 to 20 ring atoms, is mono- or polycyclic, optionally contains fused rings, are is unsubstituted or substituted by one or more identical or different groups $R^S$ as defined above, and wherein at least one of the acceptor units is a unit of formula I.

Preferably the spacer units, if present, are located between the donor and acceptor units such that a donor unit and an acceptor unit are not directly connected to each other.

Preferably the conjugated polymer comprises, very preferably consists of, one or more repeating units selected from formula U1-U4, and/or one or more repeating units selected from formulae U5-U7

| | |
|---|---|
| -(A)- | U1 |
| -(A-Sp)- | U2 |
| -(A-D)- | U3 |
| -(Sp-A-Sp)- | U4 |
| -(D)- | U5 |
| -(D-Sp)- | U6 |
| -(Sp-D-Sp)- | U7 | wherein D denotes a donor unit, A denotes an acceptor unit and Sp denotes a spacer unit, all of which are selected, independently of each other and on each occurrence identically or differently, from arylene or heteroarylene that has from 5 to 20 ring atoms, is mono- or polycyclic, optionally contains fused rings, are is unsubstituted or substituted by one or more identical or different groups $R^S$ as defined above, and the polymer contains at least one repeating unit of formulae U1-U4 wherein A is a unit of formula I.

Very preferred are conjugated polymers selected from the group consisting of formula Pi-Pviii

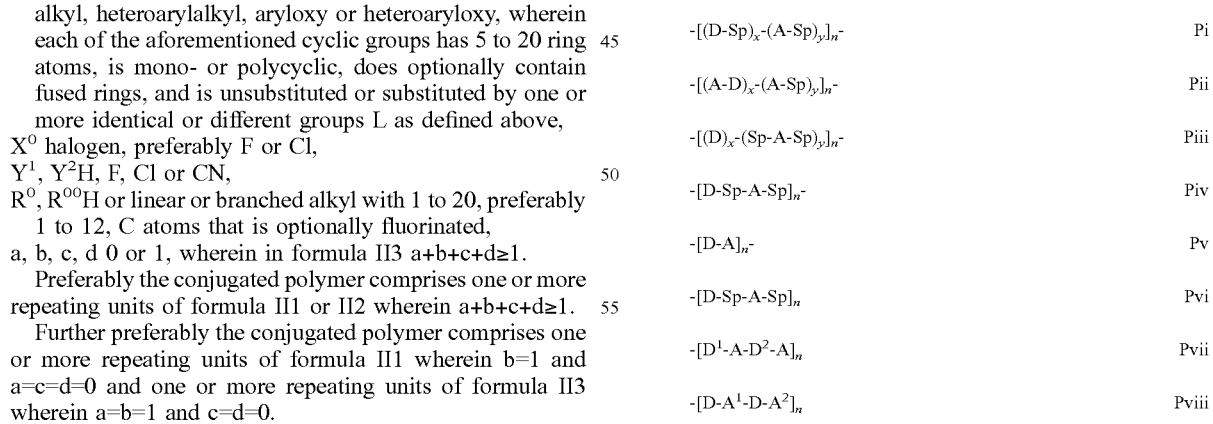

wherein A, D and Sp are as defined in formula U1-U7, A and D can each, in case of multiple occurrence, also have different meanings, $D^1$ and $D^2$ have one of the meanings given for D and are different from each other, $A^1$ and $A^2$ have one of the meanings given for A and are different from each other, x and y denote the molar fractions of the corresponding units, x and y are each, independently of one another, a non-integer >0 and <1, with x+y=1, and n is an integer >1.

Further preferred conjugated polymers are selected from the group consisting of the following formulae
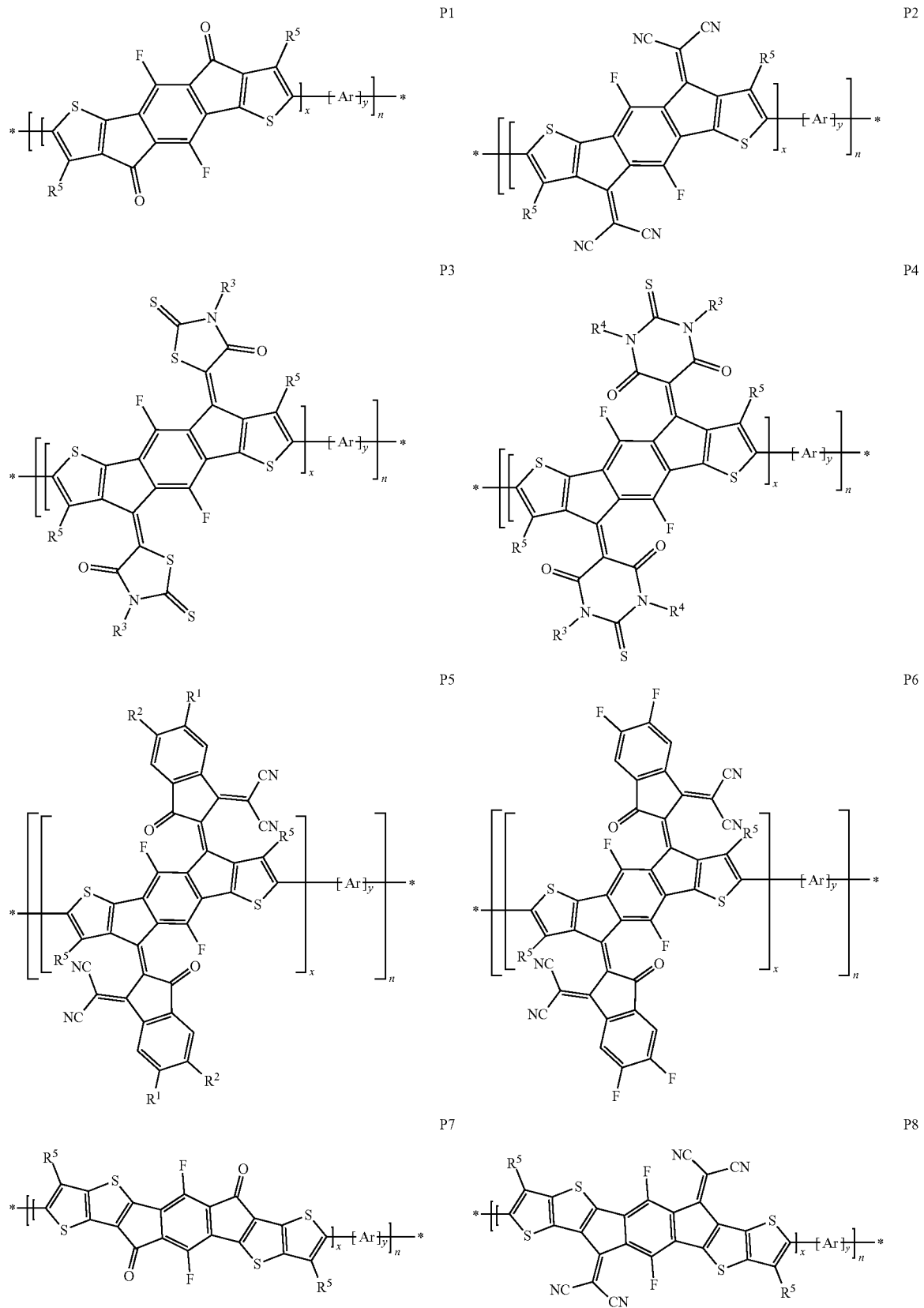

-continued
P9
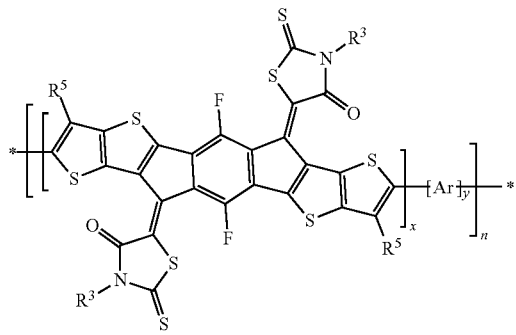
P10
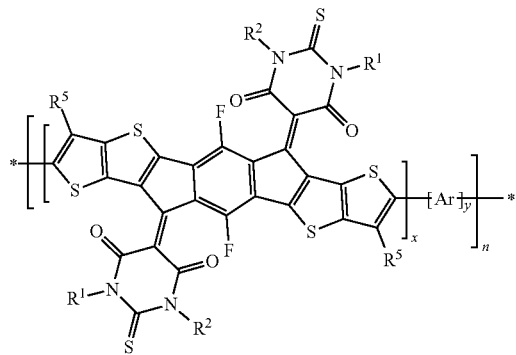
P11
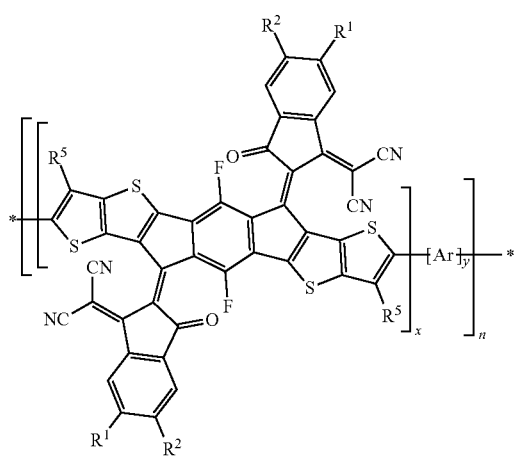
P12
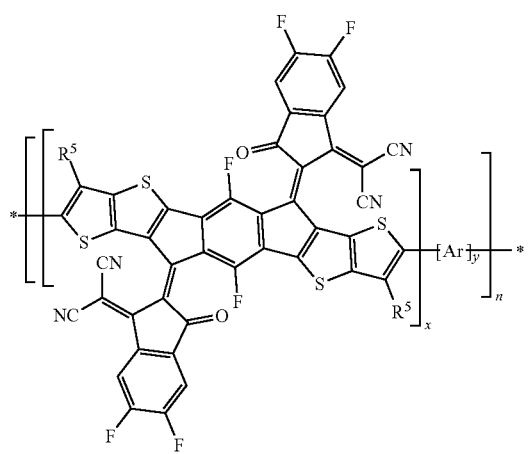
P13
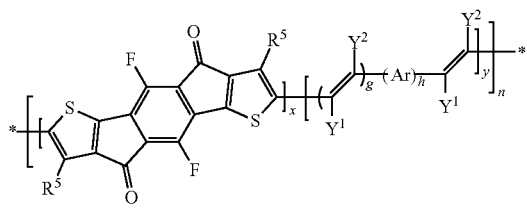
P14
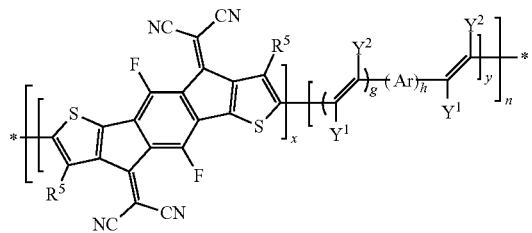
P15
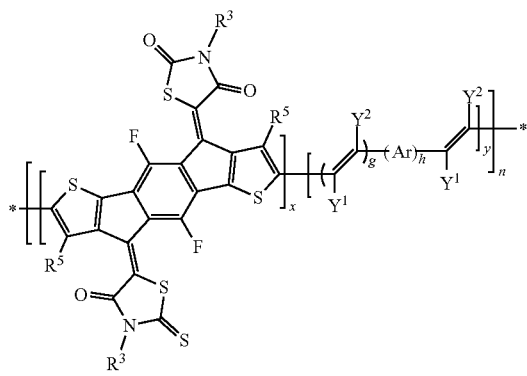
P16
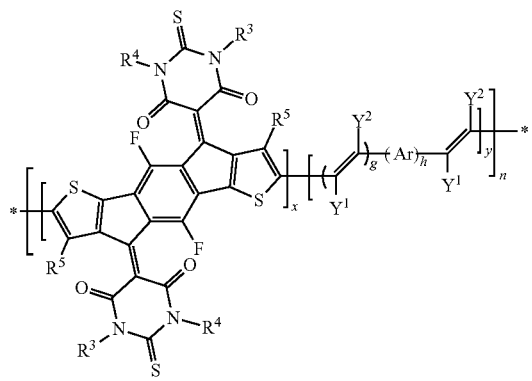

-continued
P17
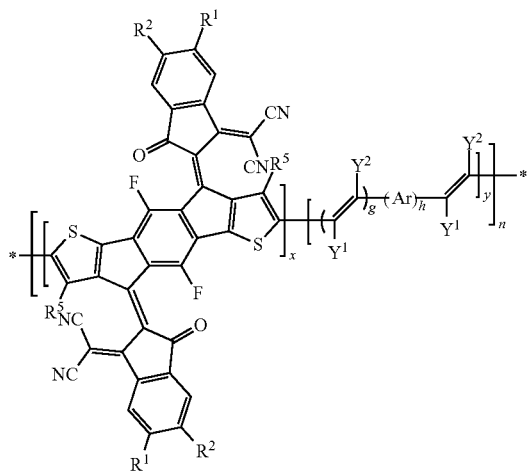
P18
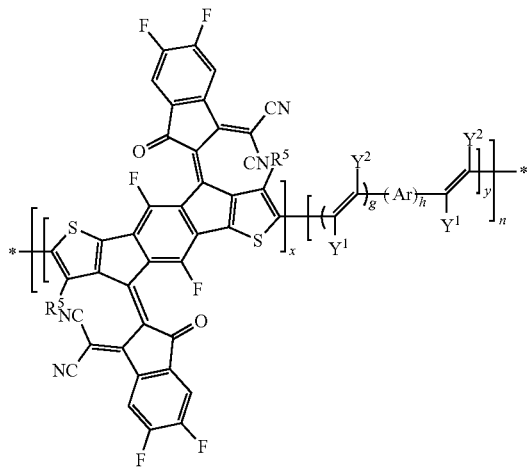
P19
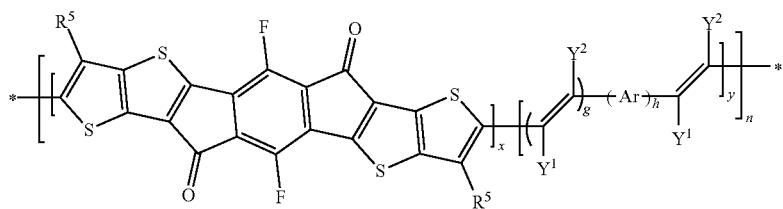
P20
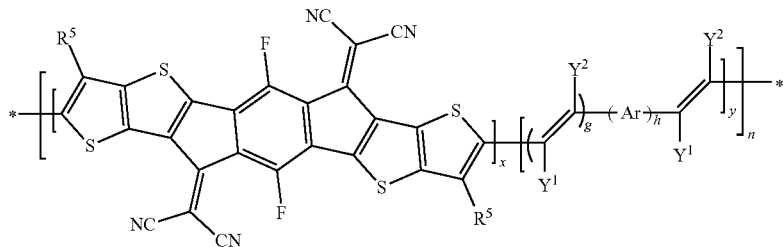
P21
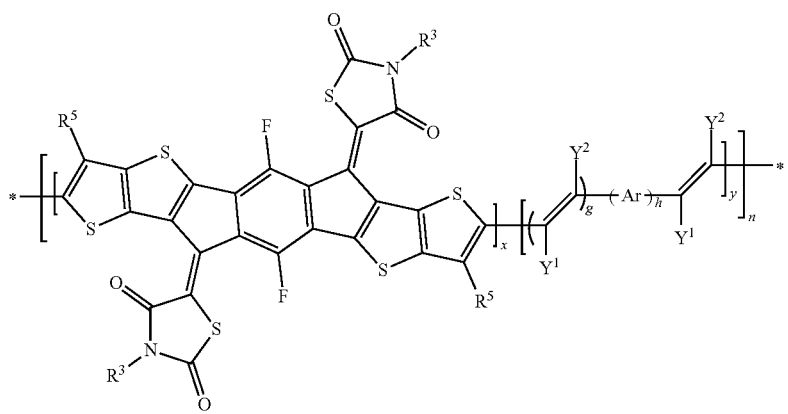

-continued
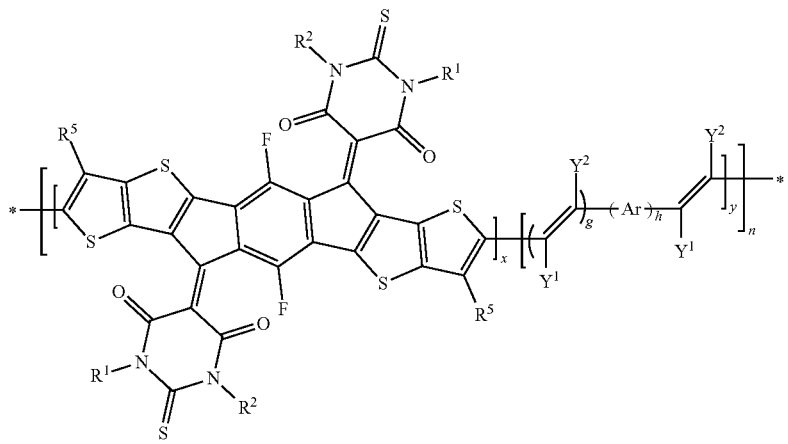
P22
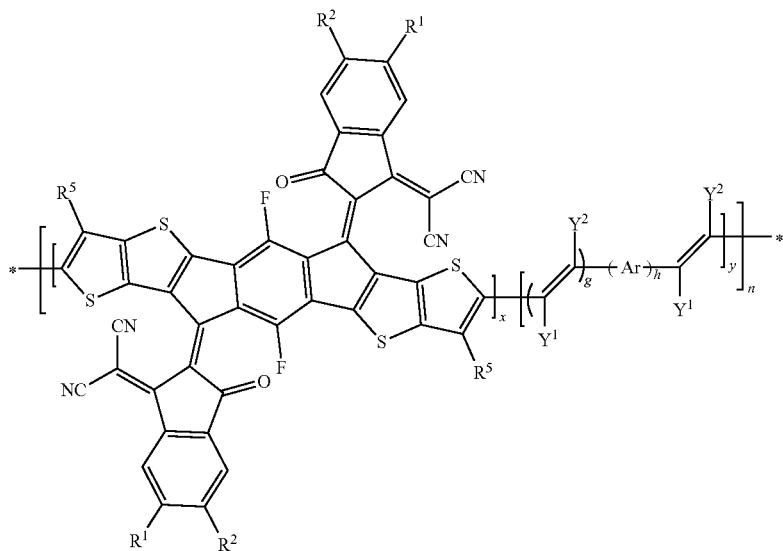
P23
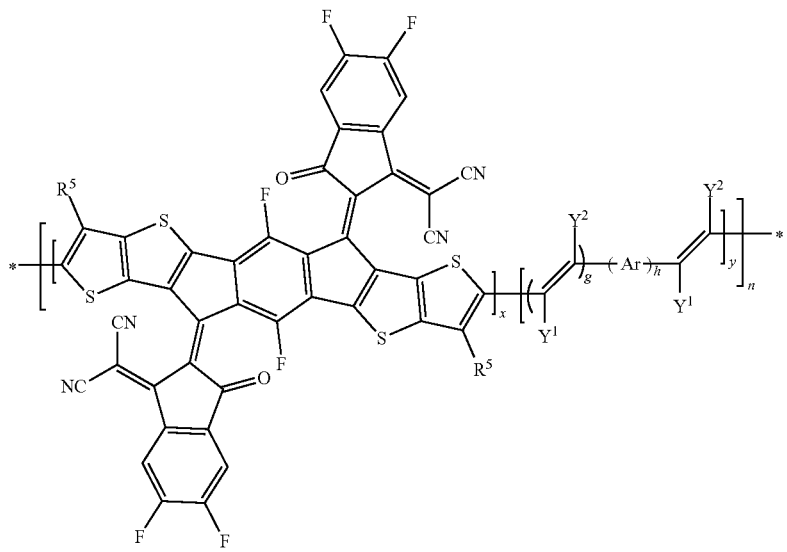
P24
wherein $Y^1$, $Y^2$, $R^1$, $R^2$, $R^3$, $R^4$ and $R^5$ have independently of each other one of the meanings given in formula I or one of their preferred meanings as given above and below, Ar has one of the meanings of $Ar^1$ as given in formula II1, x, y and n have one of the meanings given in formula Pi-Pviii, g is 0 or 1 and h is 0, 1 or 2.

Further preferred are polymers comprising one or more repeating units selected from formulae P1-P24 wherein n is 1.

Further preferred are polymers selected from formulae P13-P24 wherein g is 1 and h is 1 or 2.

Further preferred are polymers selected from formulae P13-P24 wherein g is 0 and h is 0.

Further preferred are polymers selected from formulae P13-P24 wherein $Y^1$ and $Y^2$ are H.

In the polymers of formula Pi-viii and P1-P24 which are composed of two building blocks [ ]$_x$ and [ ]$_y$, x and y are preferably a non-integer from 0.1 to 0.9, very preferably from 0.25 to 0.75, most preferably from 0.4 to 0.6.

In a preferred embodiment of the present invention $R^S$, on each occurrence identically or differently, denotes F, Cl or linear, branched or cyclic alkyl with 1 to 30, preferably 1 to 20, C atoms, in which one or more CH$_2$ groups are optionally replaced by —O—, —S—, —C(=O)—, C(=O)—O—, —O—C(=O)—, —CF$_2$— or —CH=CH—, and very preferably linear or branched alkyl, alkoxy, oxaalkyl, thioalkyl, alkylcarbonyl or alkylcarbonyloxy with 1 to 30, preferably 1 to 20 C atoms that is optionally fluorinated.

In another preferred embodiment of the present invention $R^S$, on each occurrence identically or differently, denotes aryl, aryloxy, heteroaryl or heteroaryloxy, each of which has 5 to 20 ring atoms and optionally contains fused rings and is unsubstituted or substituted by one or more groups L as defined above. Very preferably $R^S$ according to this preferred embodiment is selected from phenyl, pyrrole, furan, pyridine, thiazole, thiophene, thiadiazole, triazole, pyrazine, thieno[3,2-b]thiophene or thieno[2,3-b]thiophene, each of which is unsubstituted or substituted with F or alkyl, alkoxy or thioalkyl having 1 to 20 C atoms and being optionally fluorinated.

Preferably $R^S$ in the formulae above and below is selected, on each occurrence identically or differently, from the following groups:
a) the group consisting of linear or branched alkyl, alkoxy, oxaalkyl, thioalkyl, alkylcarbonyl or alkoxycarbonyl with 1 to 24 C atoms, preferably 1 to 20 C atoms, that is optionally fluorinated, preferably selected from formulae SUB1-SUB6 above,
b) the group consisting of aryl and heteroaryl that has 5 to 20 ring atoms, is mono- or polycyclic, does optionally contain fused rings, and is unsubstituted or substituted by one or more identical or different groups, L as defined in formula I1, very preferably phenyl or thiophene that is optionally substituted with alkyl or alkoxy having 1 to 20 C atoms that is optionally fluorinated, preferably selected from formulae SUB7-SUB18 above,
c) the group consisting of F, Cl and CN.

In another preferred embodiment of the present invention, $R^S$ denotes, on each occurrence identically or differently, straight-chain, branched or cyclic alkyl with 1 to 20 C-atoms wherein one or more CH$_2$ or CH$_3$ groups are substituted by a cationic or anionic group.

The cationic and anionic groups are preferably selected from the preferred embodiments as defined above for $R^{1-8}$.

In the conjugated polymers according to the present invention, the total number of repeating units n is preferably from 2 to 10,000. The total number of repeating units n is preferably ≥5, very preferably ≥10, most preferably 50, and preferably ≤500, very preferably ≤1,000, most preferably ≤2,000, including any combination of the aforementioned lower and upper limits of n.

The conjugated polymers of the present invention include homopolymers and copolymers, like statistical or random copolymers, alternating copolymers and block copolymers, as well as combinations thereof.

The conjugated polymers are preferably statistical copolymers.

Especially preferred are repeating units and polymers of formulae II1-II3, U1-U7, Pi-Pviii and P1-P24, wherein $Ar^1$-4, Ar, D, $D^1$ and $D^2$ are selected from the group consisting of the following formulae

(D1)

(D2)

(D3)

(D4)

(D5)

(D6)

(D7)

(D8)

(D9)

-continued
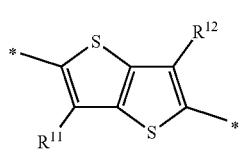
(D10)
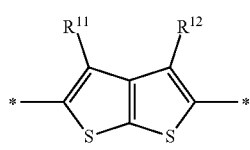
(D11)
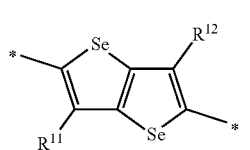
(D12)
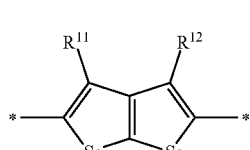
(D13)
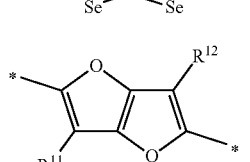
(D14)
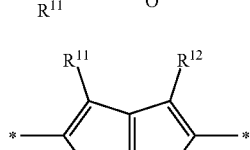
(D15)
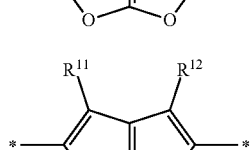
(D16)
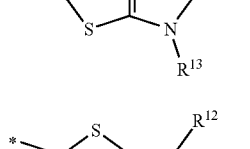
(D17)
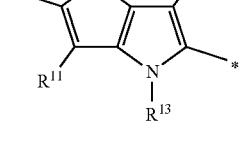
(D18)
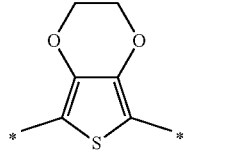
(D19)
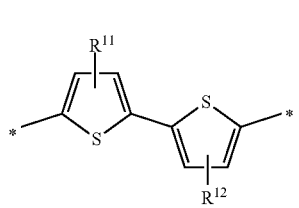
-continued
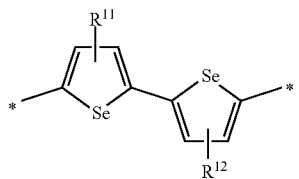
(D20)
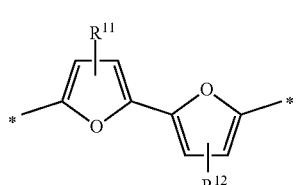
(D21)
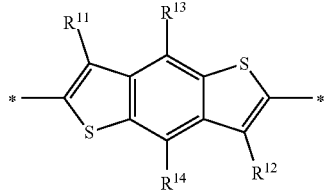
(D22)
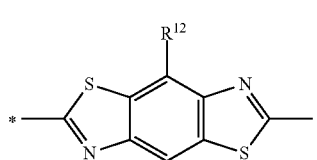
(D23)
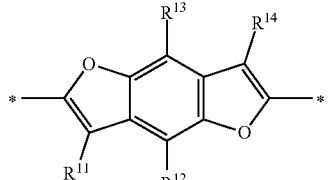
(D24)
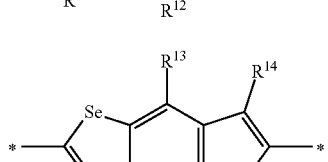
(D25)
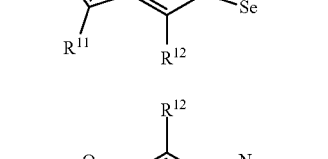
(D26)
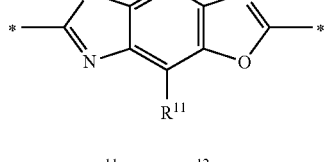
(D27)
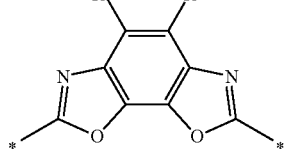

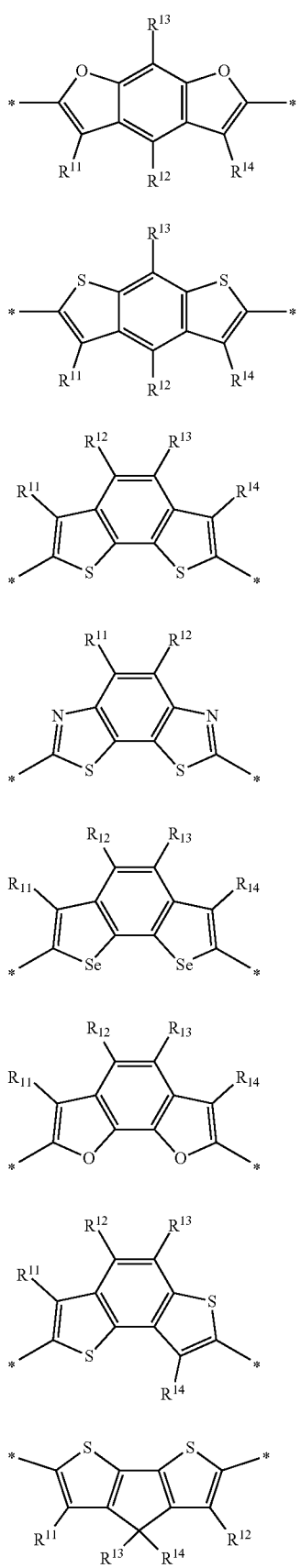
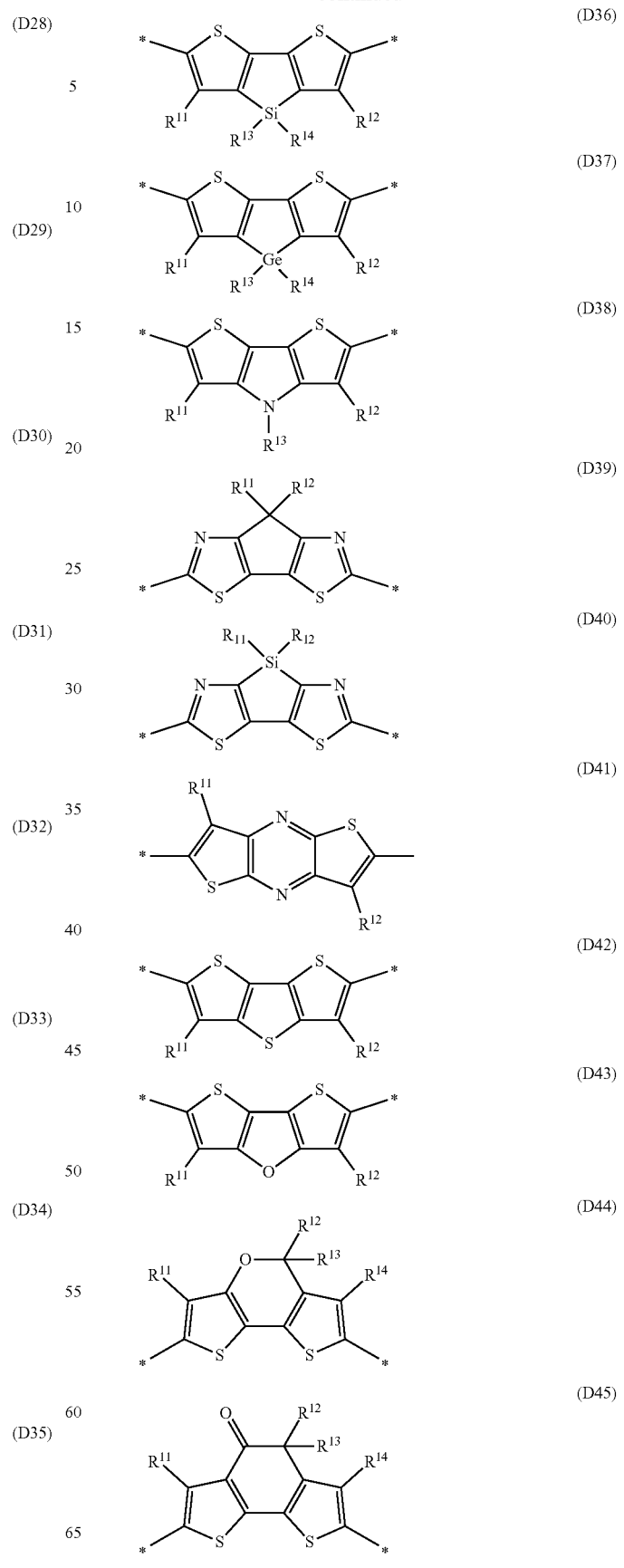

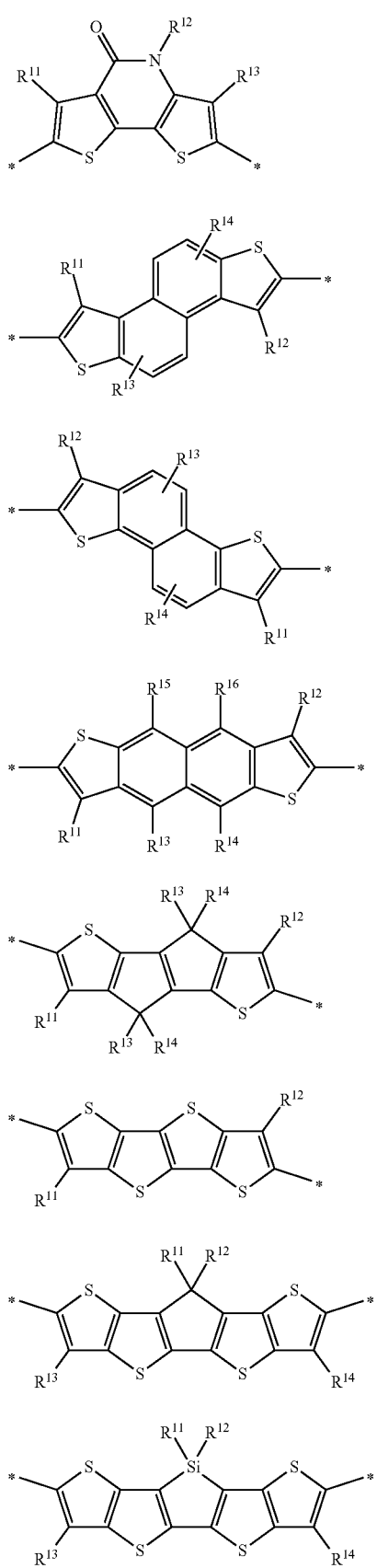
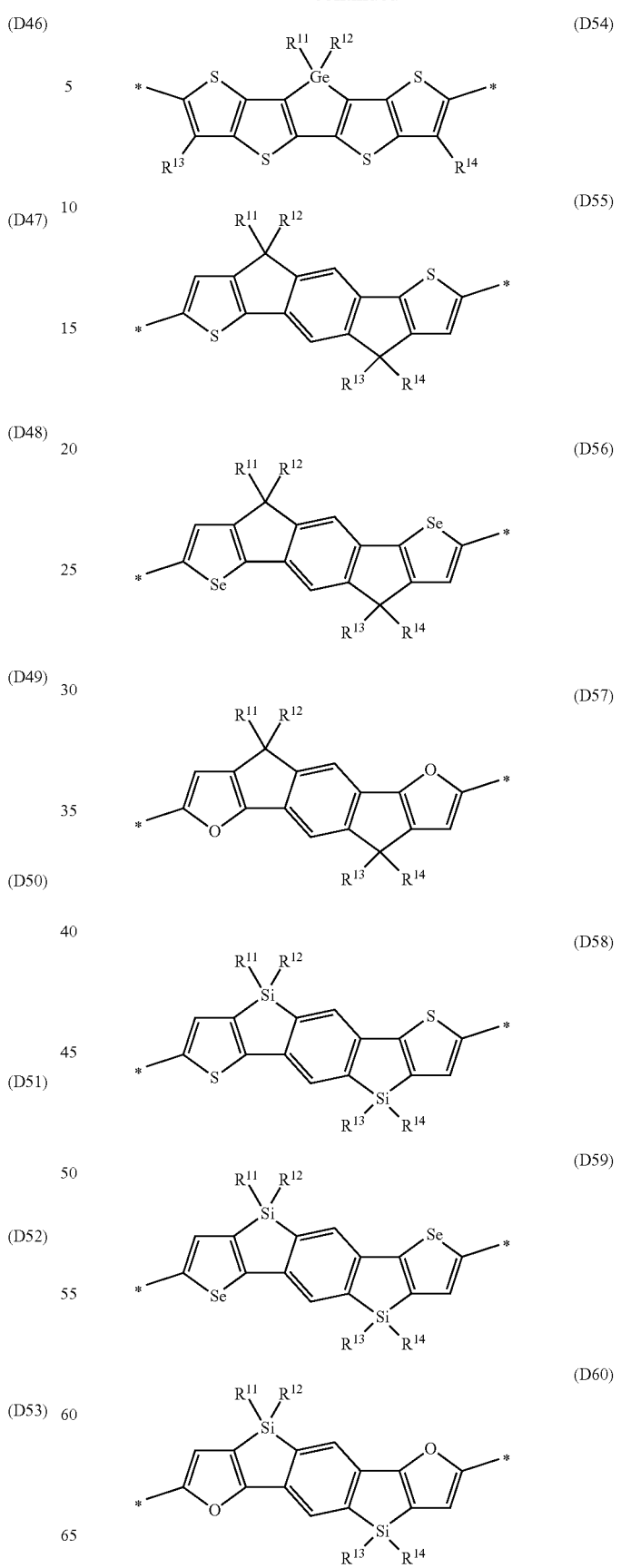

-continued
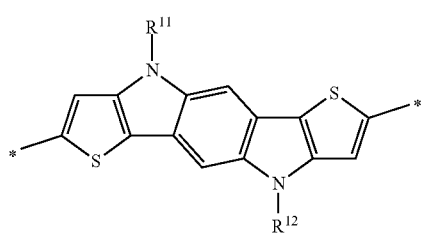
(D61)
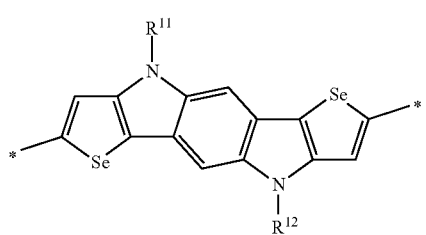
(D62)
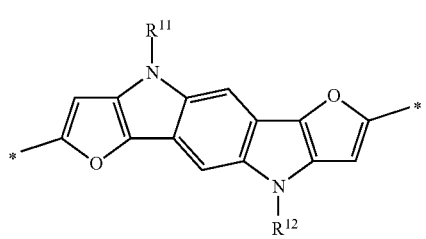
(D63)
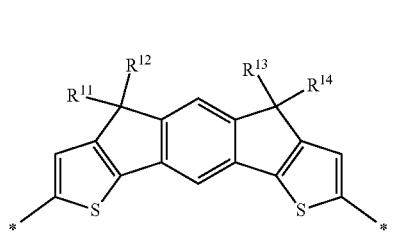
(D64)
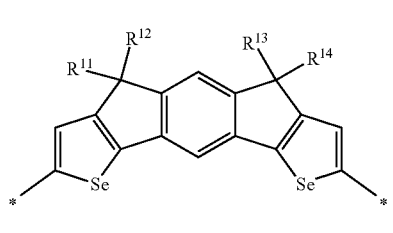
(D65)
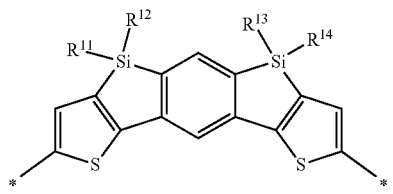
(D66)
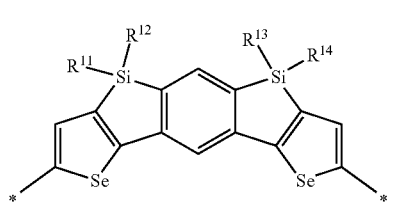
(D67)
-continued
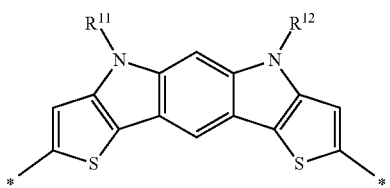
(D68)
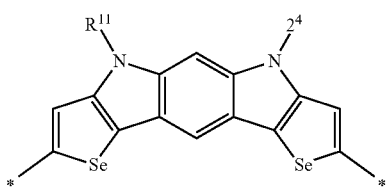
(D69)
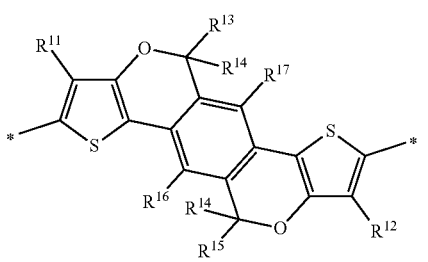
(D70)
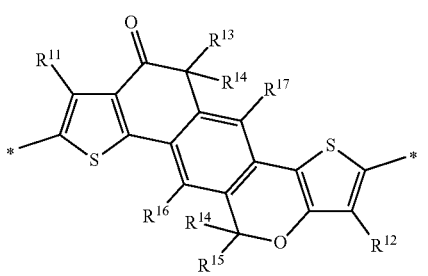
(D71)
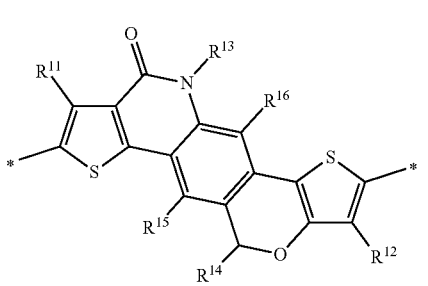
(D72)
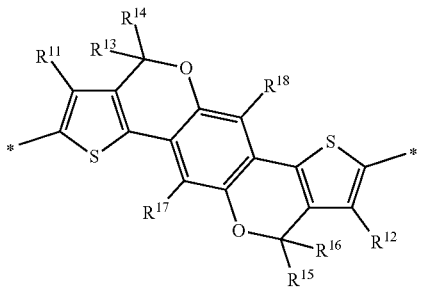
(D73)

(D74)
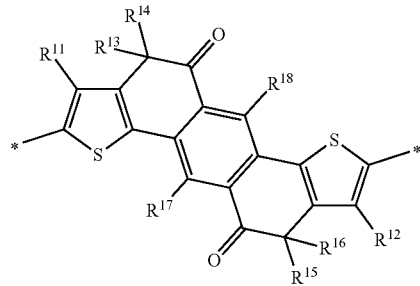
(D75)
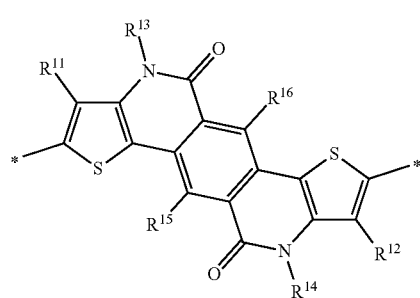
(D76)
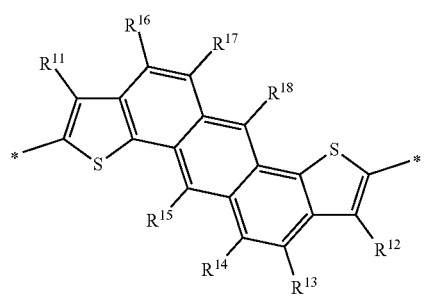
(D77)
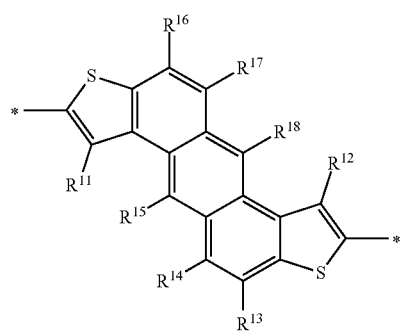
(D78)
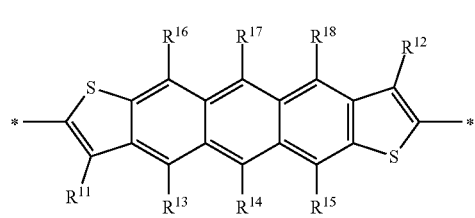
(D79)
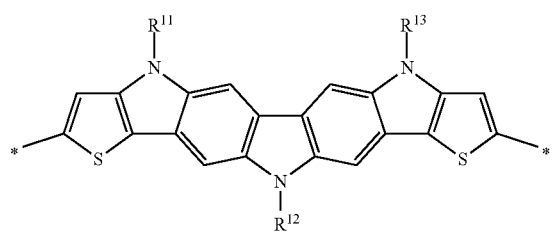
(D80)
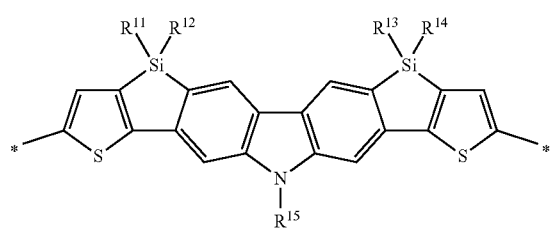
(D81)
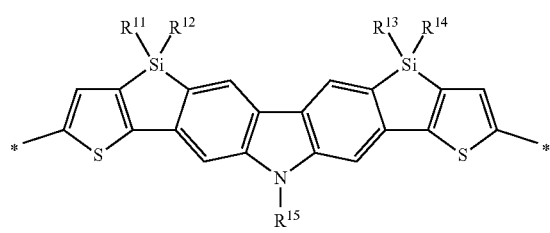
(D82)
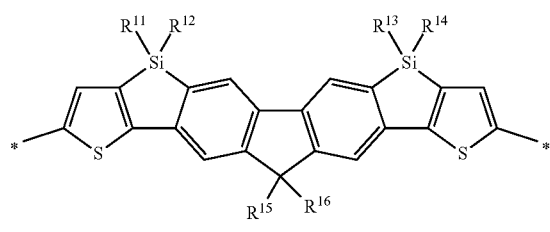
(D83)
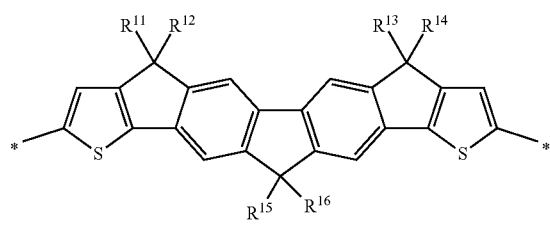
(D84)
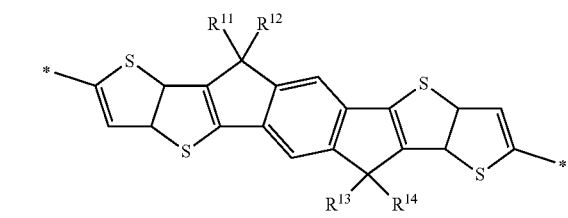

-continued
(D85)
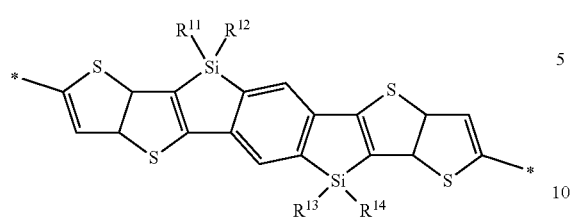
(D86)
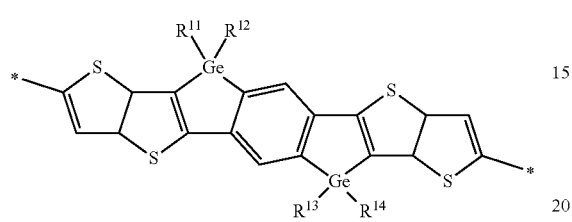
(D87)
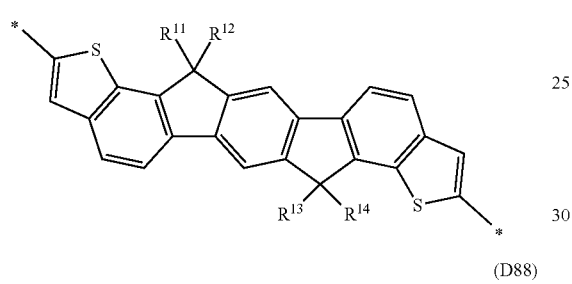
(D88)
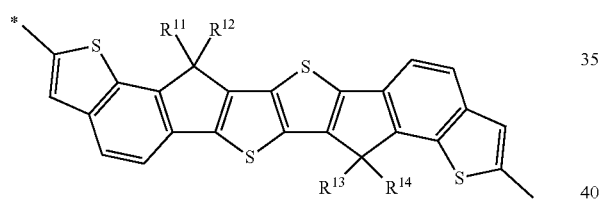
(D89)
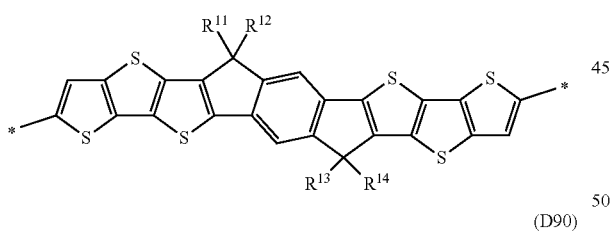
(D90)
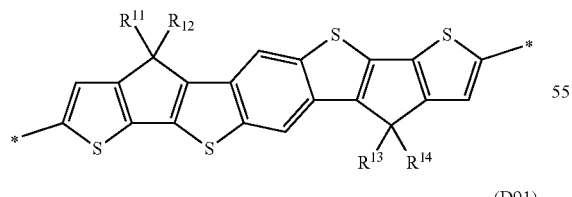
(D91)
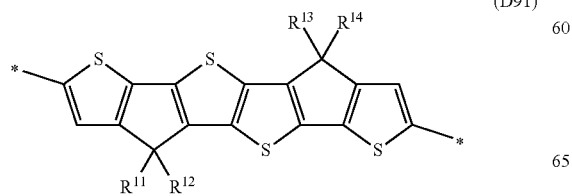
-continued
(D92)
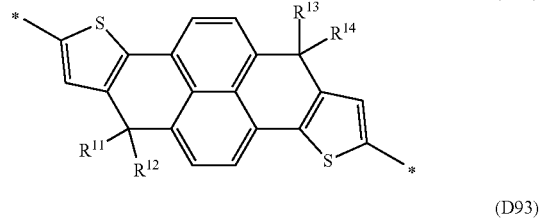
(D93)
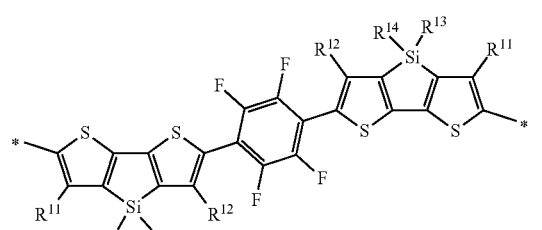
(D94)
(D95)
(D96)
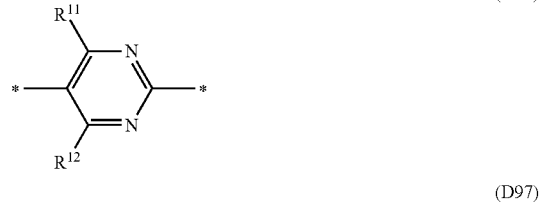
(D97)
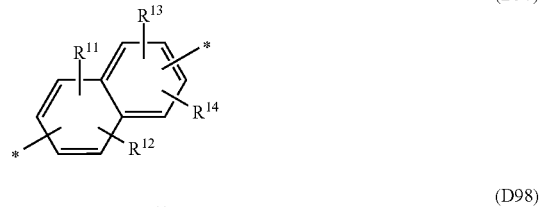
(D98)
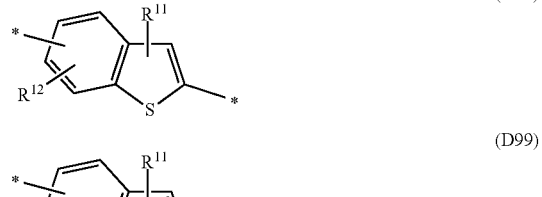
(D99)
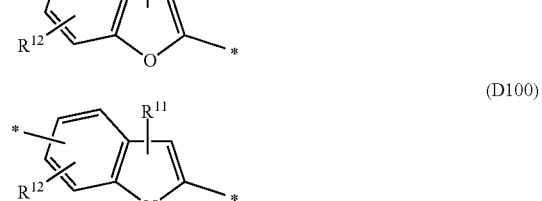
(D100)

-continued
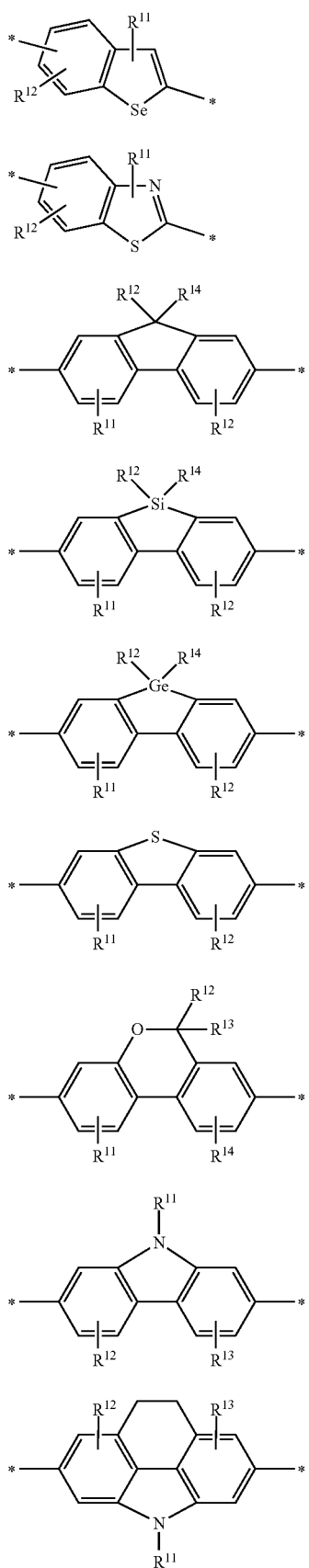
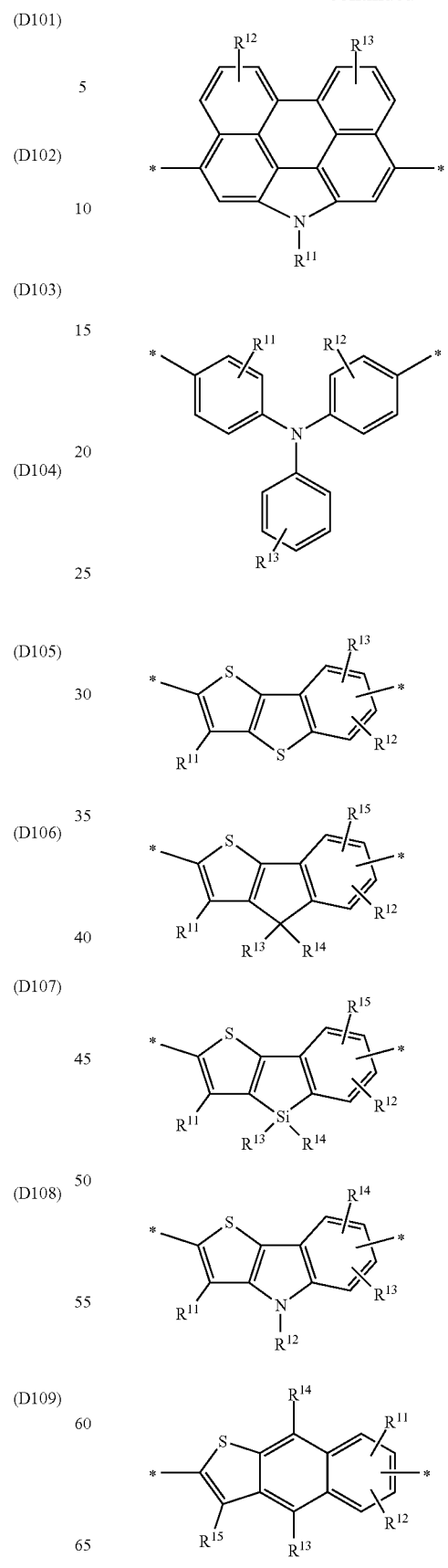

-continued
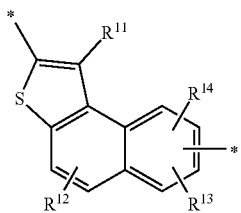
(D117)
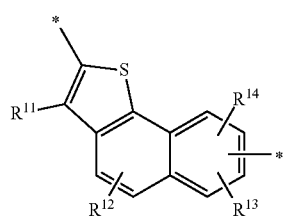
(D118)
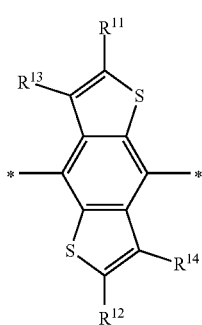
(D119)
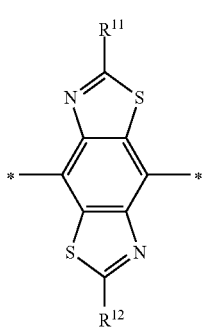
(D120)
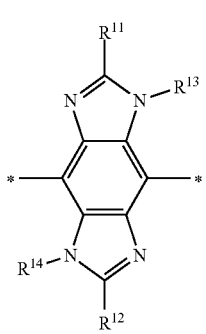
(D121)
-continued
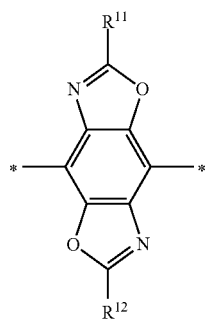
(D122)
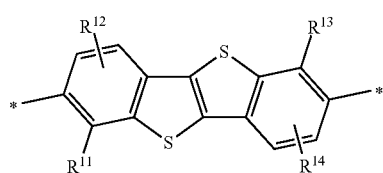
(D123)
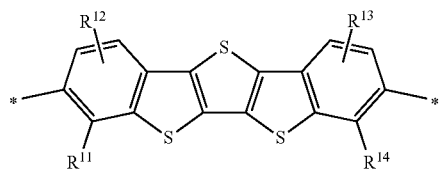
(D124)
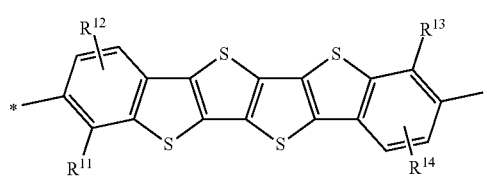
(D125)
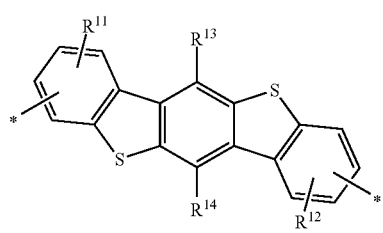
(D126)
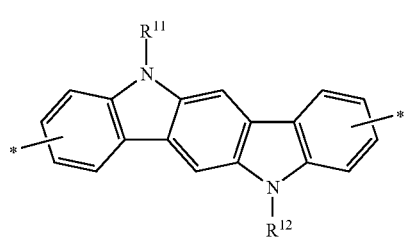
(D127)
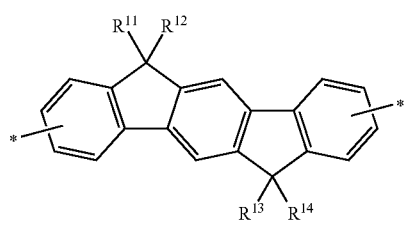
(D128)

-continued
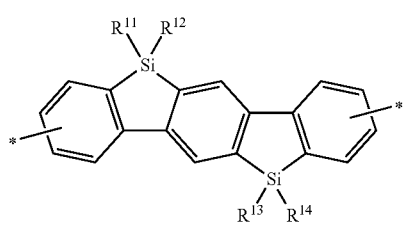
(D129)
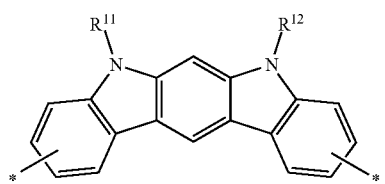
(D130)
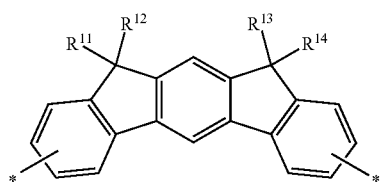
(D131)
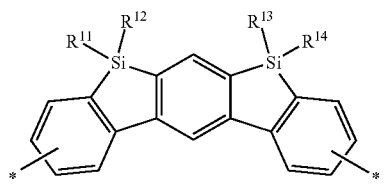
(D132)
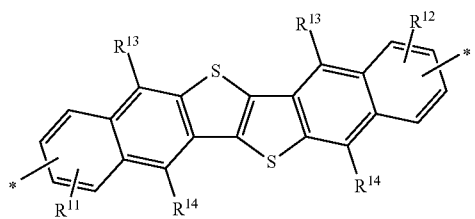
(D133)
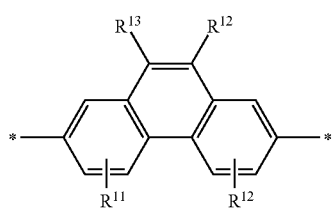
(D134)
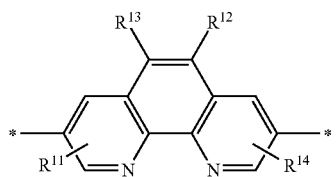
(D135)
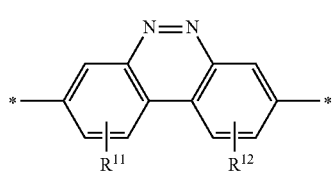
(D136)
-continued
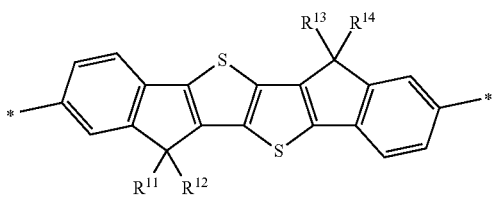
(D137)
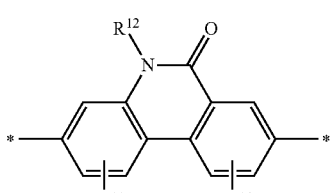
(D138)
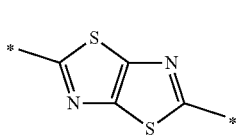
(D139)
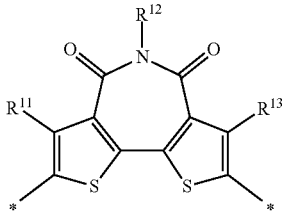
(D140)
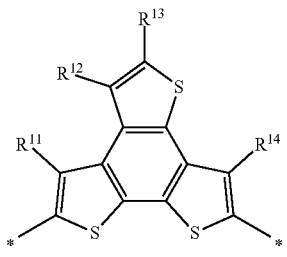
(D141)
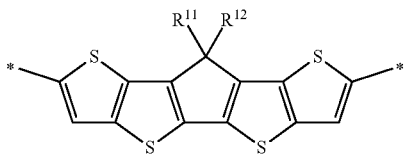
(D142)
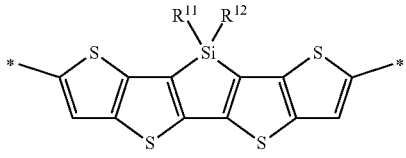
(D143)
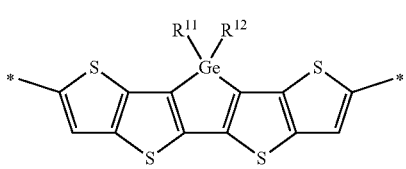
(D144)

(D145) 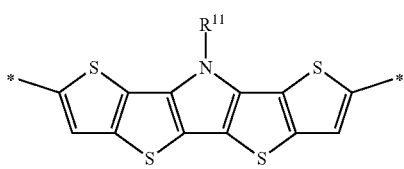

(D146) 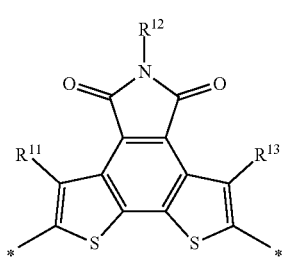

(D147) 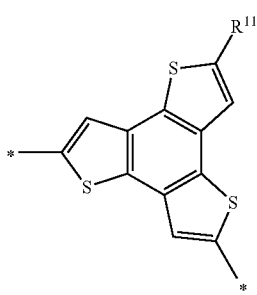

(D148) 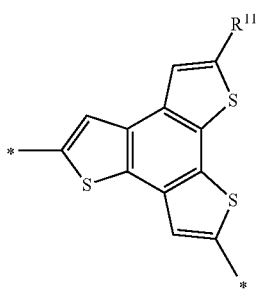

(D149) 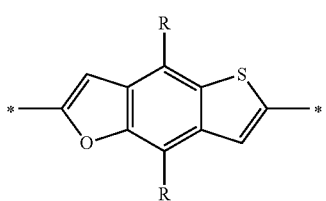

(D150) 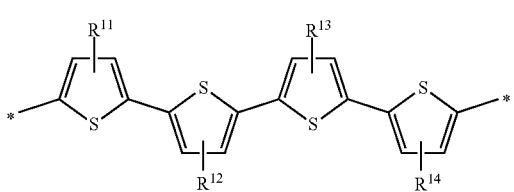

(D151) 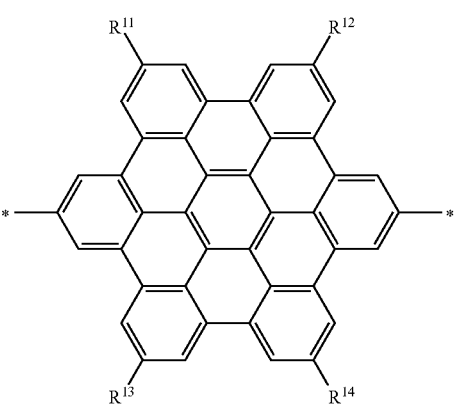

wherein $R^{11}$, $R^{12}$, $R^{13}$, $R^{14}$, $R^{15}$, $R^{16}$, $R^{17}$ and $R^{18}$ independently of each other, and on each occurrence identically or differently, denote H or have one of the meanings of $R^S$ as defined in formula II1 or one of its preferred meanings as given above and below.

Preferred units $Ar^{1-4}$, Ar, D, $D^1$ and $D^2$ are selected from formulae D1, D7, D10, D11, D19, D22, D29, D30, D35, D36, D37, D44, D55, D84, D87, D88, D89, D93, D94, D106, D111, D119, D139, D140, D141, D146, D147 and D150 wherein preferably at least one of $R^{11}$, $R^{12}$, $R^{13}$ and $R^{14}$ is different from H.

Especially preferred are repeating units of formulae II1-II3 and polymers of formulae P1-P24 wherein one or more groups $Ar^{1-4}$ or Ar are selected from the group consisting formulae D1-D151, preferably of formulae D1, D7, D10, D11, D19, D22, D29, D30, D35, D36, D37, D44, D55, D84, D87, D88, D89, D93, D94, D106, D111, D119, D139, D140, D141, D146, D147 and D150 wherein preferably at least one of $R^{11}$, $R^{12}$, $R^{13}$ and $R^{14}$ is different from H.

Further preferred are repeating units and polymers of formulae II1-II3, U1-U7, Pi-Pviii and P1-P24 wherein $Ar^{1-4}$, Ar, A, $A^1$ and $A^2$ are selected from the group consisting of the following formulae (A1) 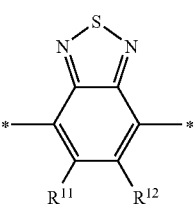

(A2) 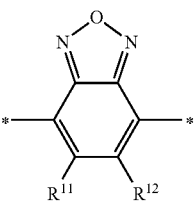

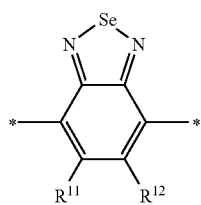 (A3)
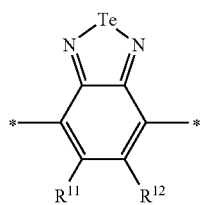 (A4)
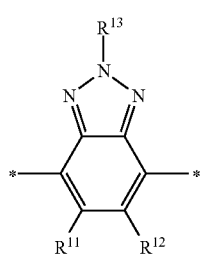 (A5)
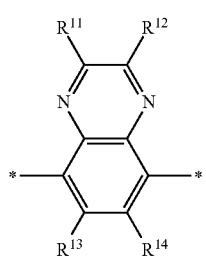 (A6)
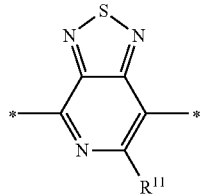 (A7)
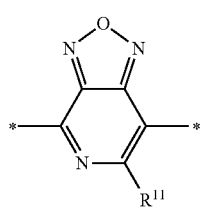 (A8)
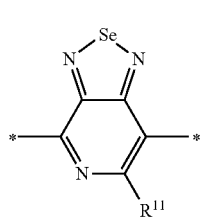 (A9)
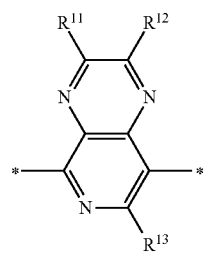 (A10)
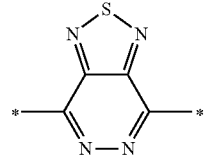 (A11)
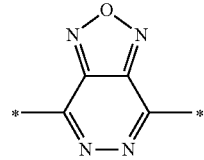 (A12)
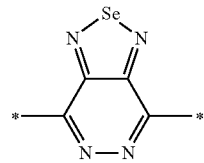 (A13)
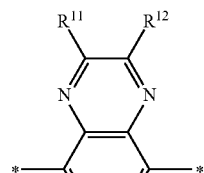 (A14)
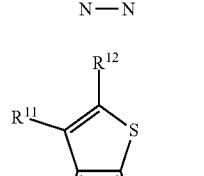 (A15)
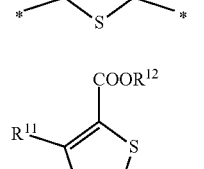 (A16)
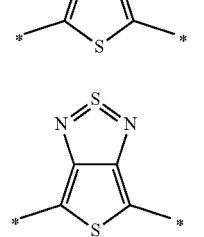 (A17)

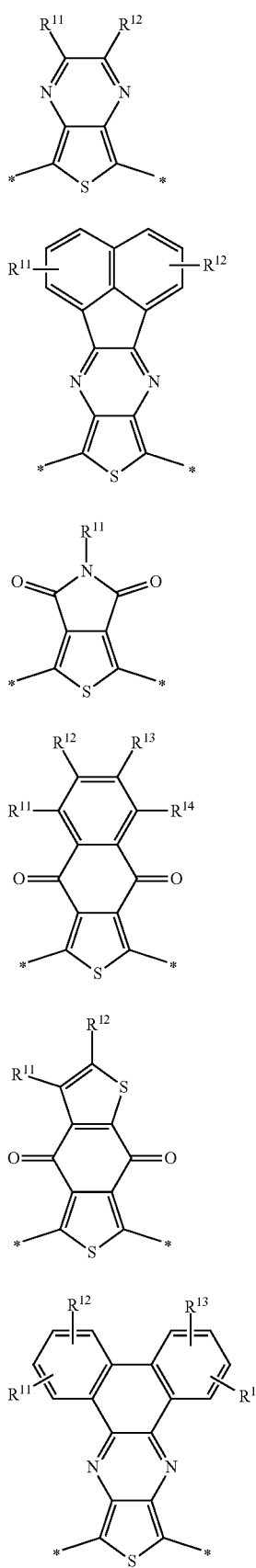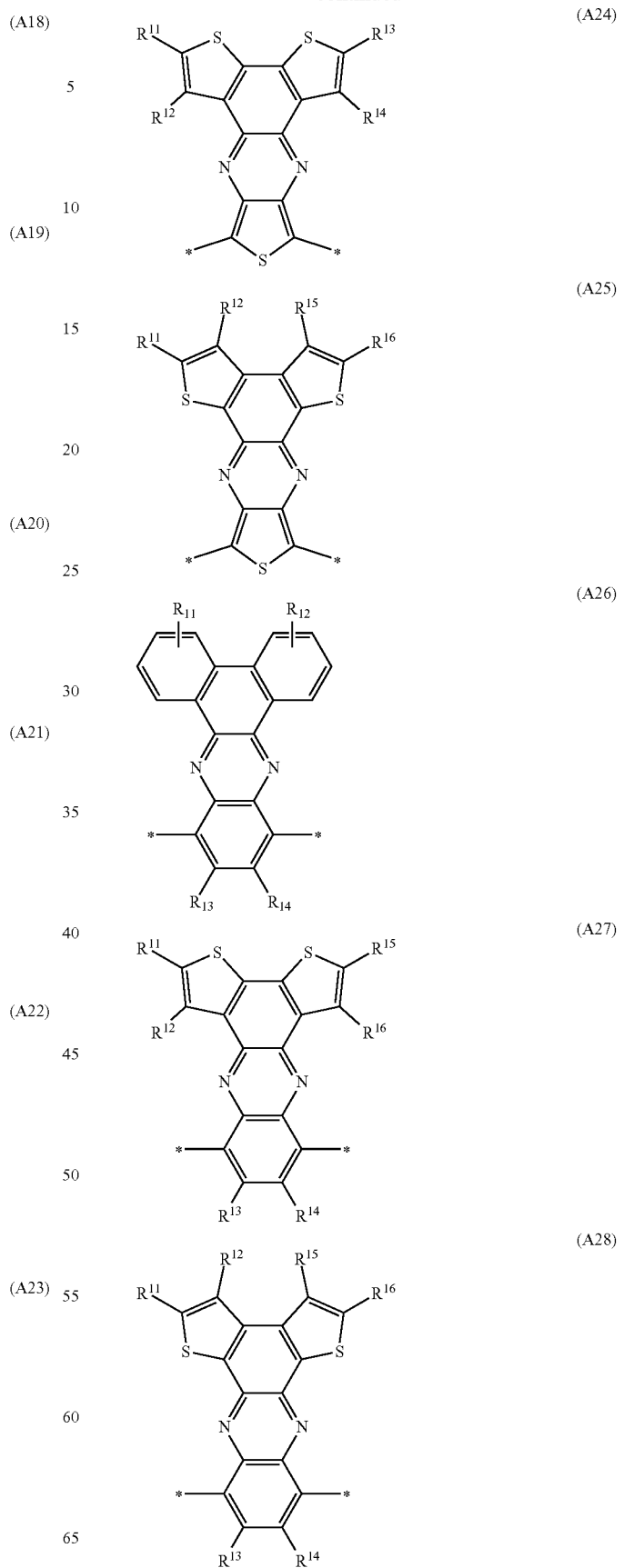

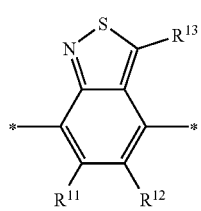 (A29)
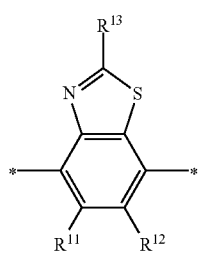 (A30)
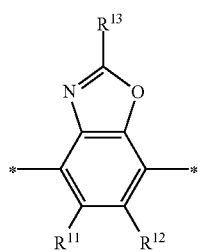 (A31)
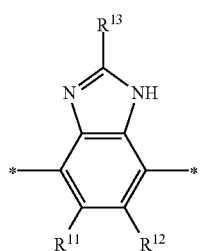 (A32)
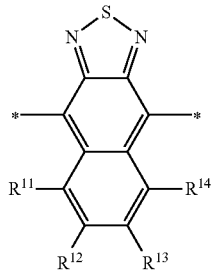 (A33)
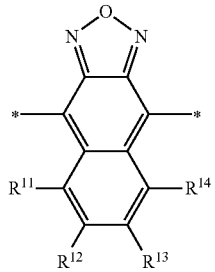 (A34)
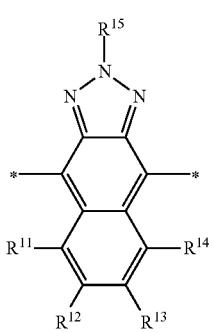 (A35)
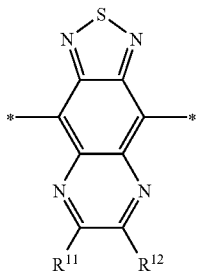 (A36)
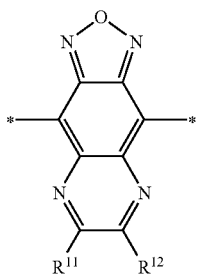 (A37)
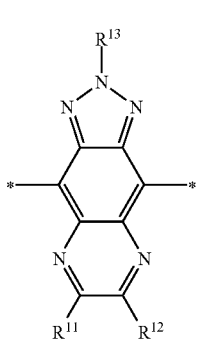 (A38)
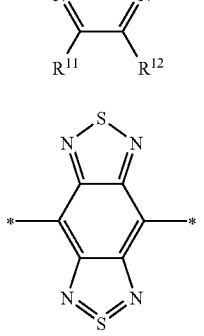 (A39)

-continued
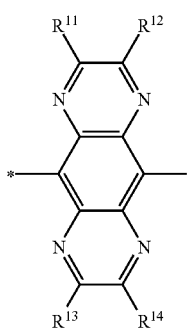 (A40)
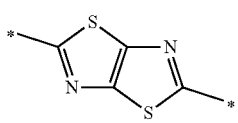 (A41)
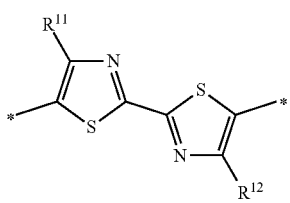 (A42)
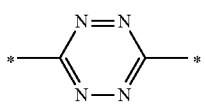 (A43)
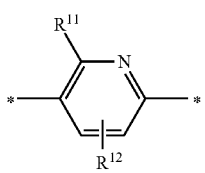 (A44)
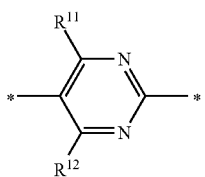 (A45)
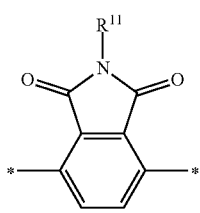 (A46)
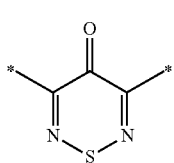 (A47)
-continued
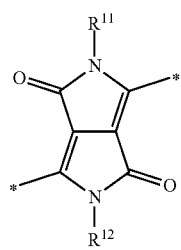 (A48)
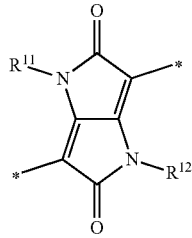 (A49)
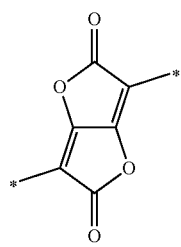 (A50)
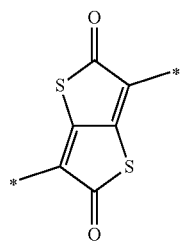 (A51)
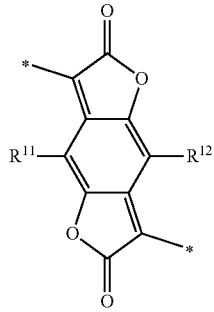 (A52)
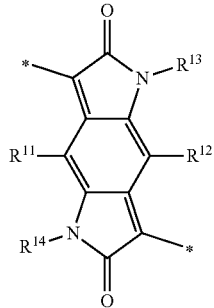 (A53)

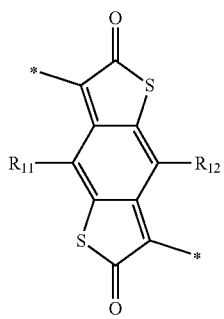
(A54)
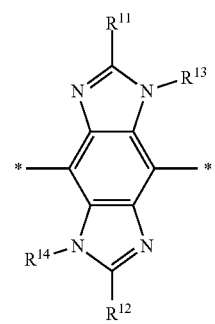
(A59)
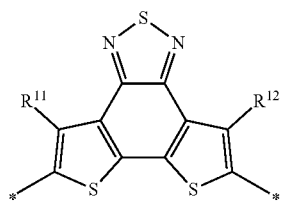
(A55)
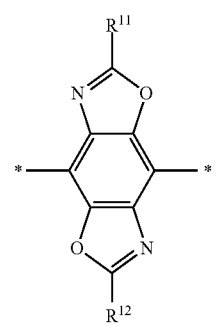
(A60)
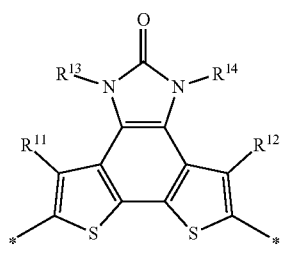
(A56)
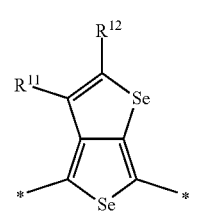
(A61)
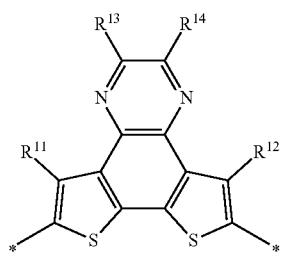
(A57)
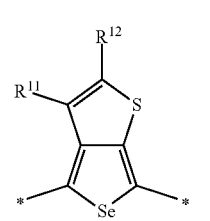
(A62)
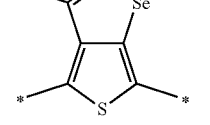
(A63)
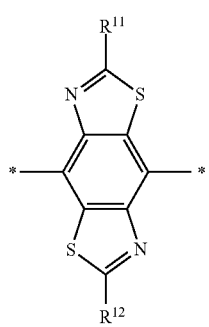
(A58)
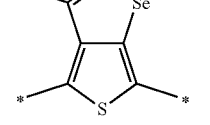
(A64)

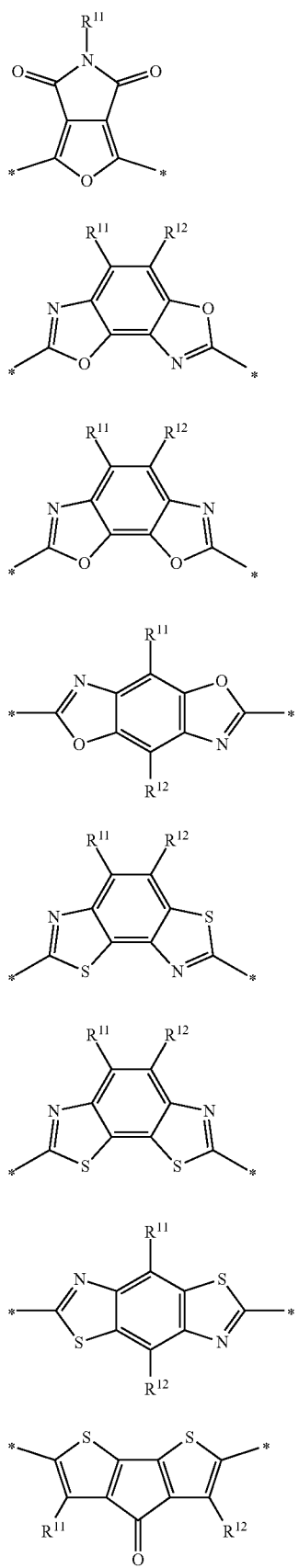
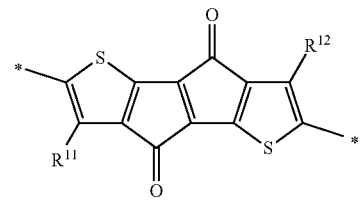
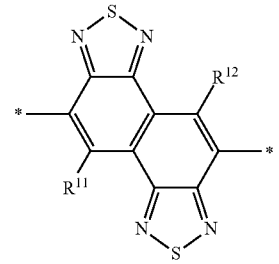
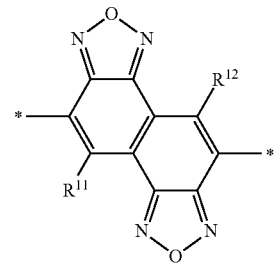
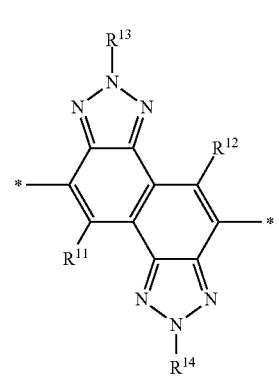
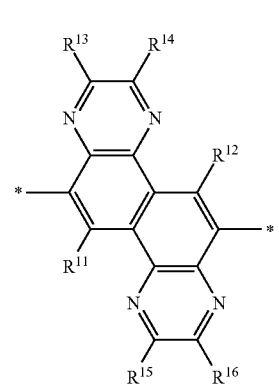

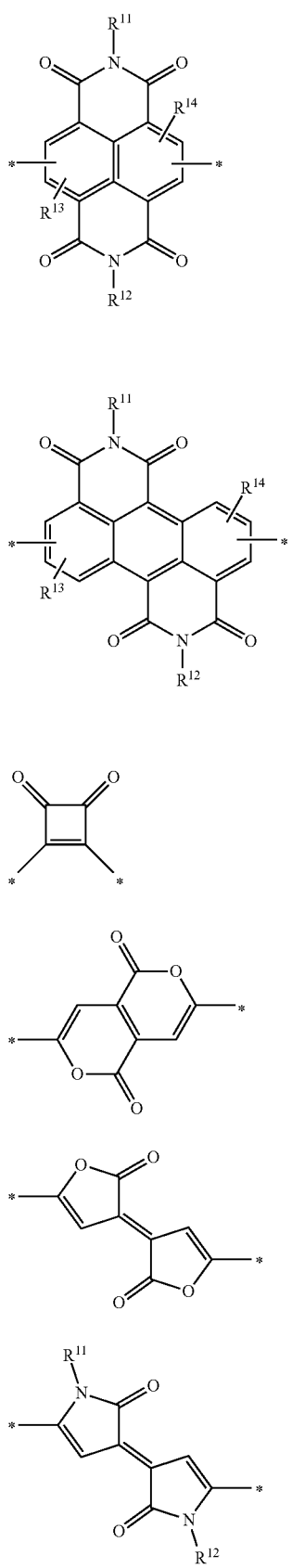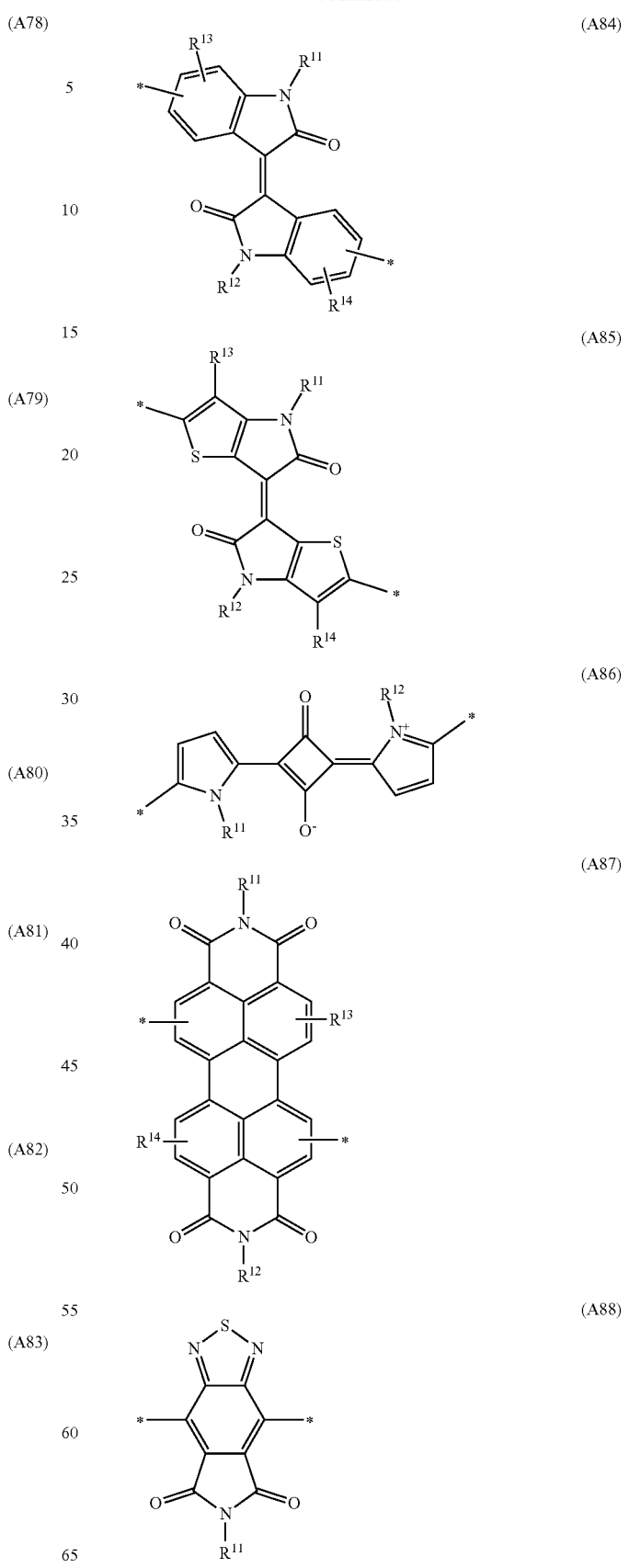

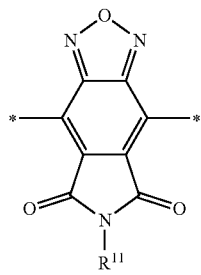
(A89)
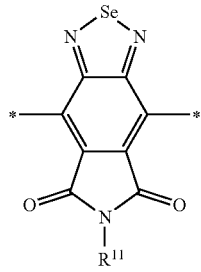
(A90)
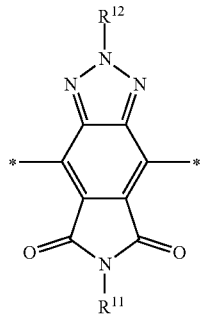
(A91)
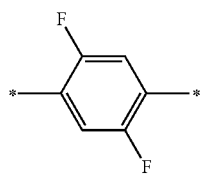
(A92)
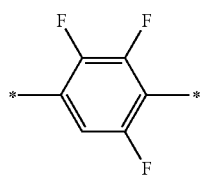
(A93)
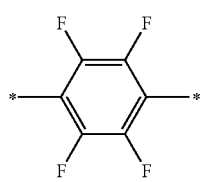
(A94)
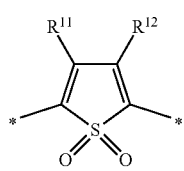
(A95)
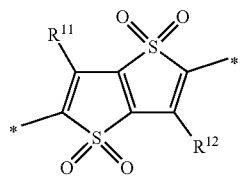
(A96)
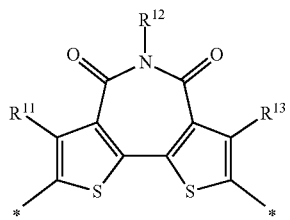
(A97)
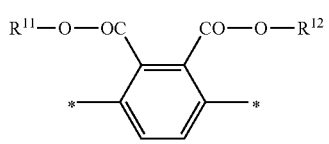
(A98)
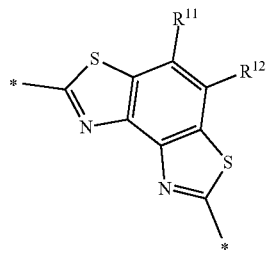
(A99)
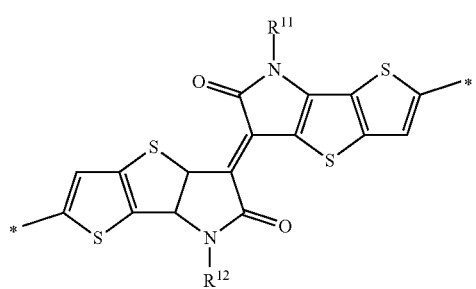
(A100)
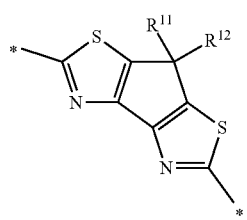
(A101)

(A102)

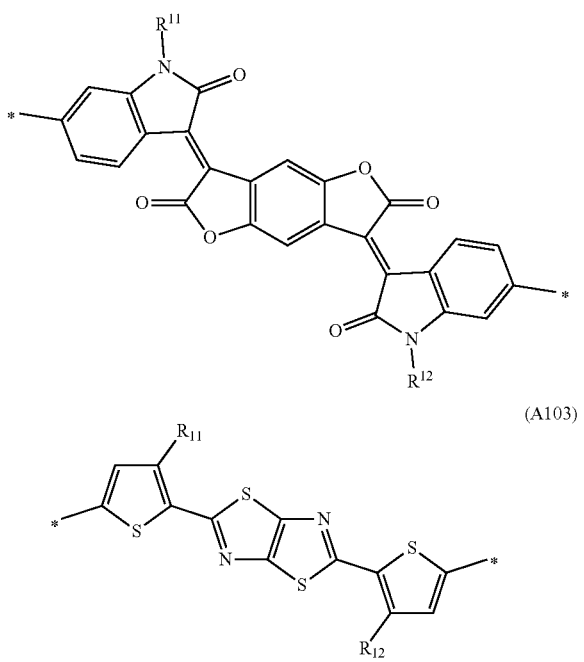

(A103)

wherein $R^{11}$, $R^{12}$, $R^{13}$, $R^{14}$, $R^{15}$ and $R^{16}$ independently of each other, and on each occurrence identically or differently, denote H or have one of the meanings of $R^S$ as defined in formula II1 or one of its preferred meanings as given above and below, and in unit A1 $R^{11}$ and $R^{12}$ have meanings that are different from $X^1$ and $X^2$ in as defined in formula I.

Preferred units $Ar^{1-4}$, Ar and A are selected from formulae A1, A5, A6, A7, A15, A16, A20, A74, A88, A92, A94, A98, A99, A100 and A103, wherein preferably at least one of $R^{11}$, $R^{12}$, $R^{13}$ and $R^{14}$ is different from H.

Especially preferred are repeating units of formulae II1-II3 and polymers of formulae P1-P24 wherein one or more groups $Ar^{1-4}$ or Ar are selected from the group consisting formulae A1-A103, preferably of formulae A1, A5, A6, A7, A15, A16, A20, A74, A88, A92, A94, A98, A99, A100 and A103, wherein preferably at least one of $R^{11}$, $R^{12}$, $R^{13}$ and $R^{14}$ is different from H.

Further preferred are repeating units and polymers of formulae II1-II3, U1-U7, Pi-Pviii and P1-P24 wherein, $Ar^{1-4}$, Ar and Sp are selected from the group consisting of the following formulae

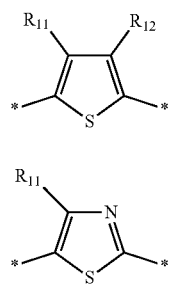 Sp1

Sp2

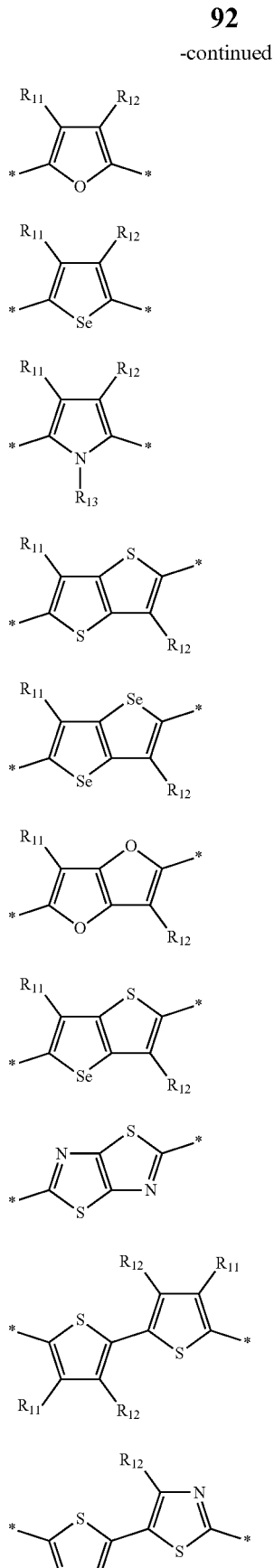

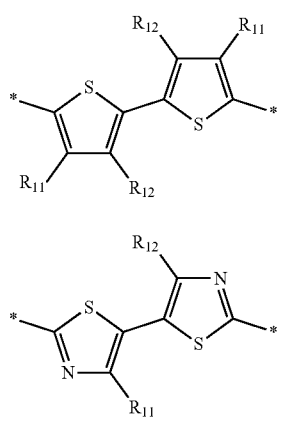

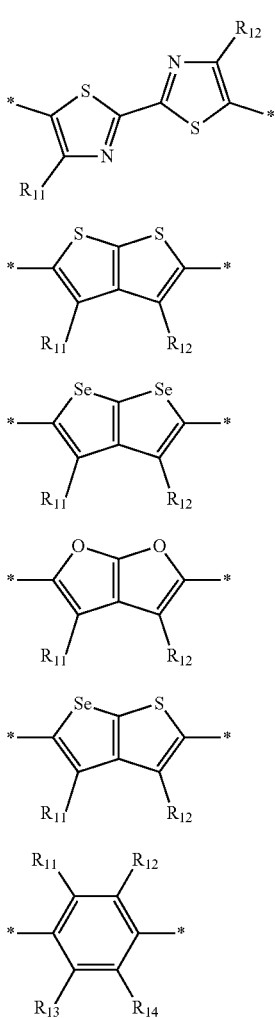

Sp13, Sp14, Sp15, Sp16, Sp17, Sp18 wherein $R^{11}$, $R^{12}$, $R^{13}$, $R^{14}$ independently of each other, and on each occurrence identically or differently, denote H or have one of the meanings of $R^S$ as defined in formula II1.

In the formulae Sp1 to Sp17 preferably $R^{11}$ and $R^{12}$ are H. In formula Sp18 preferably $R^{11-14}$ are H or F.

Very preferred units $Ar^{1-4}$, Ar and Sp are selected from formulae Sp1, Sp2, Sp6, Sp10, Sp11, Sp12, Sp13 and Sp14, most preferably form formulae Sp1, Sp6, Sp10 and Sp14, wherein preferably one of $R^{11}$ and $R^{12}$ is H or both $R^{11}$ and $R^{12}$ are H.

Especially preferred are repeating units of formulae II1-II3 and polymers of formulae P1-P24 wherein one or more groups $Ar^{14}$ or Ar, independently of each other and on each occurrence identically or differently, are selected from the group consisting formulae Sp1-Sp18, preferably of formulae Sp1, Sp2, Sp6, Sp10, Sp11, Sp12, Sp13 and Sp14, most preferably form formulae Sp1, Sp6, Sp10 and Sp14, wherein preferably one of $R^{11}$ and $R^{12}$ is H or both $R^{11}$ and $R^{12}$ are H.

Further preferred are repeating units and polymers of formulae U1-U7 and Pi-Pviii wherein a) one or more, preferably all, groups D are selected from the group consisting of the formulae D1-D151, very preferably of the formulae D1, D7, D10, D11, D19, D22, D29, D30, D35, D36, D37, D44, D55, D84, D87, D88, D89, D93, D94, D106, D111, D119, D139, D140, D141, D146, D147 and D150, and/or b) one or more, preferably all, groups A are selected from the group consisting of the formulae A1-A103, very preferably of the formulae A1, A5, A6, A7, A15, A16, A20, A36, A74, A84, A88, A92, A94, A98, A99, A100 and A103, and c) one or more, preferably all, groups Sp are selected from the group consisting of the formulae Sp1-Sp18, very preferably of the formulae Sp1, Sp2, Sp6, Sp10, Sp11, Sp12, Sp13 and Sp14.

Preferably the conjugated polymer contains, preferably consists of, one or more units of formula I and a) one or more donor units D selected from the group consisting of the formulae D1, D7, D10, D11, D19, D22, D29, D30, D35, D36, D37, D44, D55, D84, D87, D88, D89, D93, D94, D106, D111, D119, D139, D140, D141, D146, D147 and D150 and/or b) one or more acceptor units A selected from the group consisting of the formulae A1, A5, A6, A7, A15, A16, A20, A74, A88, A92, A94, A98, A99, A100 and A103, and c) optionally one or more spacer units Sp selected from the group consisting of the formulae Sp1-Sp18, very preferably of the formulae Sp1, Sp6, Sp10 and Sp14, wherein the spacer units, if present, are preferably located between the donor and acceptor units such that a donor unit and an acceptor unit are not directly connected to each other.

Further preferred are conjugated polymers selected of formula PT $$R^{31}\text{-chain-}R^{32} \qquad \text{PT}$$

wherein "chain" denotes a polymer chain selected of formula Pi-Pviii or P1-P24, and $R^{31}$ and $R^{32}$ have independently of each other one of the meanings of $R^{11}$ as defined above, or denote, independently of each other, H, F, Br, Cl, I, —CH$_2$Cl, —CHO, —CR'=CR"$_2$, —SiR'R"R"', —SiR'X'X", —SiR'R"X', —SnR'R"R"', —BR'R", —B(OR')(OR"), —B(OH)$_2$, —O—SO$_2$—R', —C≡CH, —C≡C—SiR'$_3$, —ZnX' or an endcap group, X' and X" denote halogen, R', R" and R"' have independently of each other one of the meanings of $R^0$ given in formula 1, and preferably denote alkyl with 1 to 24 C atoms, and two of R', R" and R"' may also form a cyclosilyl, cyclostannyl, cycloborane or cycloboronate group with 2 to 20 C atoms together with the respective hetero atom to which they are attached.

Preferred endcap groups $R^{31}$ and $R^{32}$ are H, $C_{1-20}$ alkyl, or optionally substituted $C_{6-12}$ aryl or $C_{2-10}$ heteroaryl, very preferably H, phenyl or thiophene.

Another preferred embodiment of the present invention relates to a monomer comprising one or more units of formula I and at least two reactive groups that can be reacted to form a small molecule, oligomer or conjugated polymer as described above and below, preferably in an aryl-aryl coupling reaction. Preferably the monomer according to this preferred embodiment is a compound of formula M1 or M2

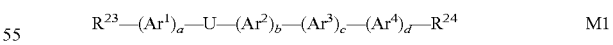

$$R^{23}\text{—}(Ar^1)_a\text{—}U\text{—}(Ar^2)_b\text{—}(Ar^3)_c\text{—}(Ar^4)_d\text{—}R^{24} \qquad \text{M1}$$

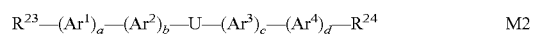

$$R^{23}\text{—}(Ar^1)_a\text{—}(Ar^2)_b\text{—}U\text{—}(Ar^3)_c\text{—}(Ar^4)_d\text{—}R^{24} \qquad \text{M2}$$

wherein U, $Ar^{1-4}$, a, b, c and d have the meanings of formula II1, or one of the preferred meanings as described above and below, and $R^{23}$ and $R^{24}$ are independently of each other selected from the group consisting of an activated C—H bond, Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, $Z^{1-4}$ are selected from the group consisting of alkyl and aryl, preferably $C_{1-10}$ alkyl and $C_{6-12}$ aryl, each being optionally substituted, and two groups $Z^2$ may also form a cycloboronate group having 2 to 20 C atoms together with the B- and O-atoms.

Preferably in the monomers of formula M1 and M2 $Ar^{1-4}$ are selected from the group consisting of formulae D1-D151, A1-A103 and Sp1-Sp18, very preferably from formulae Sp1-Sp18, most preferably from formulae Sp1, Sp6, Sp10 and Sp14.

Very preferred are monomers of formula M1 and M2 and their subformulae selected from the following preferred embodiments or any combination thereof:

U is a polycyclic group as shown in formulae S1-1 to S1-20, wherein the terminal groups $T^1$ and $T^2$ formulae S1-1 to S1-20 are replaced by a linkage to the terminal groups $R^{23}$—$(Ar^1)_a$— and —$(Ar^4)_d$—$R^{24}$ of formula M1 or M2, a+b+c+d≥1, a+b+c+d=0, a is 1 or 2, c is 0, 1 or 2, and b and d are 0, a is 1 or 2 and b, c and d are 0, a is 1 or 2, c is 1 or 2, and b and d are 0, $Ar^{1-4}$, independently of each other and on each occurrence identically or differently, are selected from the following groups a) the group consisting of the formulae D1-D151, very preferably of the formulae D1, D7, D10, D11, D19, D22, D29, D30, D35, D36, D37, D44, D55, D84, D87, D88, D89, D93, D94, D106, D111, D139, D140, D141 and D150, b) the group consisting of the formulae A1-A103, very preferably of the formulae A1, A6, A7, A15, A16, A20, A36, A74, A84, A88, A92, A98 and A103, c) the group consisting of the formulae Sp1-Sp18, very preferably of the formulae Sp1, Sp2, Sp6, Sp10, Sp11, Sp12, Sp13 and Sp14.

Further preferred are monomers selected from the following subformulae

| | |
|---|---|
| $R^{23}$—U—$R^{24}$ | M1a |
| $R^{23}$-Sp-U-Sp-$R^{24}$ | M1b |
| $R^{23}$-Sp-U—$R^{24}$ | M1c |
| $R^{23}$—U-D-$R^{24}$ | M1d | wherein U, $R^{23}$ and $R^{24}$ are as defined in formula M1, and Sp and D are as defined in formula U1-U7 or have one of the preferred meanings given above and below.

Very preferred are monomers of formulae M1a-M1d wherein a) one or more, preferably all, groups D are selected from the group consisting of the formulae D1-D151, very preferably of the formulae D1, D7, D10, D11, D19, D22, D29, D30, D35, D36, D37, D44, D55, D84, D87, D88, D89, D93, D94, D106, D111, D119, D139, D140, D141, D146, D147 and D150, and/or b) one or more, preferably all, groups Sp are selected from the group consisting of the formulae Sp1-Sp18, very preferably of the formulae Sp1, Sp2, Sp6, Sp10, Sp11, Sp12, Sp13 and Sp14.

Further preferred are monomers of formula M1, M2, M1a-M1d and their subformulae wherein $R^{23}$ and $R^{24}$ are selected from Br, Cl, $B(OZ^2)_2$ and $Sn(Z^4)_3$.

The monomers, small molecules, oligomers and polymers according to the present invention can be synthesized according to or in analogy to methods that are known to the skilled person and are described in the literature. Other methods of preparation can be taken from the examples.

The conjugated polymers according to the present invention can be prepared for example by copolymerising one or more monomers of formula M1, M2 or M1a-M1d with each other or with one or monomers of the following formulae in an aryl-aryl coupling reaction

| | |
|---|---|
| $R^{23}$-Sp-$R^{24}$ | MI |
| $R^{23}$-A-$R^{24}$ | MII |
| $R^{23}$-D-$R^{24}$ | MIII |
| $R^{23}$-Sp-A-$R^{24}$ | MIV |
| $R^{23}$-Sp-D-$R^{24}$ | MV |
| $R^{23}$-Sp-A-Sp-$R^{24}$ | MVI |
| $R^{23}$-Sp-D-Sp-$R^{24}$ | MVII | wherein Sp, A and D, independently of each other and on each occurrence identically or differently, have one of the meanings given in formula U1-U7 or one of the preferred meanings given above and below, and $R^{23}$ and $R^{24}$ have the meanings given in formula M1 or one of the preferred meanings given above and below.

For example, the conjugated polymer can be suitably prepared by aryl-aryl coupling reactions, such as Yamamoto coupling, C—H activation coupling, Suzuki coupling, Stille coupling, Sonogashira coupling, Heck coupling or Buchwald coupling. Suzuki coupling, Stille coupling and Yamamoto coupling are especially preferred. The monomers which are polymerised to form the repeat units of the polymers can be prepared according to methods which are known to the person skilled in the art.

Preferably the polymer is prepared from monomers selected from formulae M1, M2, M3, M1a-d and MI-MVII as described above.

Another aspect of the invention is a process for preparing a polymer by coupling one or more identical or different monomers selected from formulae M1, M2, M1a-d with each other and/or with one or more co-monomers, preferably selected from formulae MI-MVII, in a polymerisation reaction, preferably in an aryl-aryl coupling reaction.

The small molecules, monomers, oligomers and polymers of the present invention can generally be prepared by aryl-aryl coupling reactions, such as Yamamoto coupling, Suzuki coupling, Stille coupling, Sonogashira coupling, Heck coupling or Buchwald coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in E. Nigishi et al., *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1. Stille coupling is described for example in Z. Bao et al., *J. Am. Chem. Soc.*, 1995, 117, 12426-12435 and C—H activation is described for example in M. Leclerc et al., *Angew. Chem. Int. Ed.*, 2012, 51, 2068-2071. For example, when using Yamamoto coupling, educts having two reactive halide groups are preferably used. When using Suzuki coupling, educts having two reactive boronic acid or boronic acid ester groups or two reactive halide groups are preferably used. When using Stille coupling, edcuts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as $Pd(PPh_3)_4$. Another preferred phosphine ligand is tris(ortho-tolyl)phosphine, i.e. $Pd(P(o-Tol)_3)_4$. Preferred Pd(II) salts include palladium acetate, i.e. $Pd(OAc)_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl) phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula $-O-SO_2Z^0$ can be used wherein $Z^0$ is an alkyl or aryl group, preferably $C_{1-10}$ alkyl or $C_{6-12}$ aryl. Particular examples of such leaving groups are tosylate, mesylate and triflate.

Especially suitable and preferred synthesis methods of the compounds according to the present invention are illustrated in the synthesis schemes shown hereinafter.

A suitable and preferred synthesis route Route to IDT and IDTT small molecule analogues is exemplarily shown below in Scheme 1, wherein R is a solubilizing group like for example alkyl as defined for $R^1$ above, and X is an EWG as defined above. Other compounds of formula I with a different polycyclic core can be prepared in analogous manner.

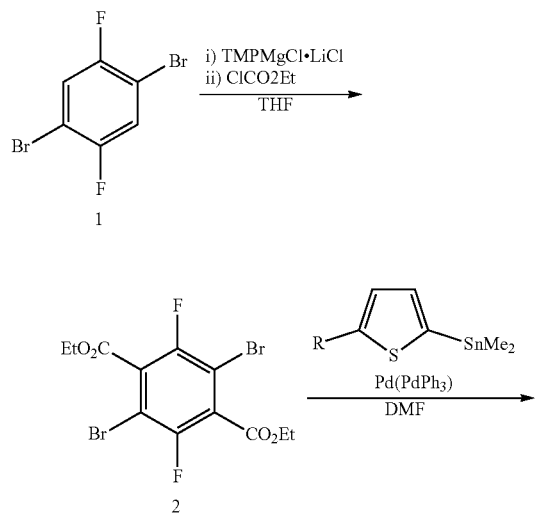

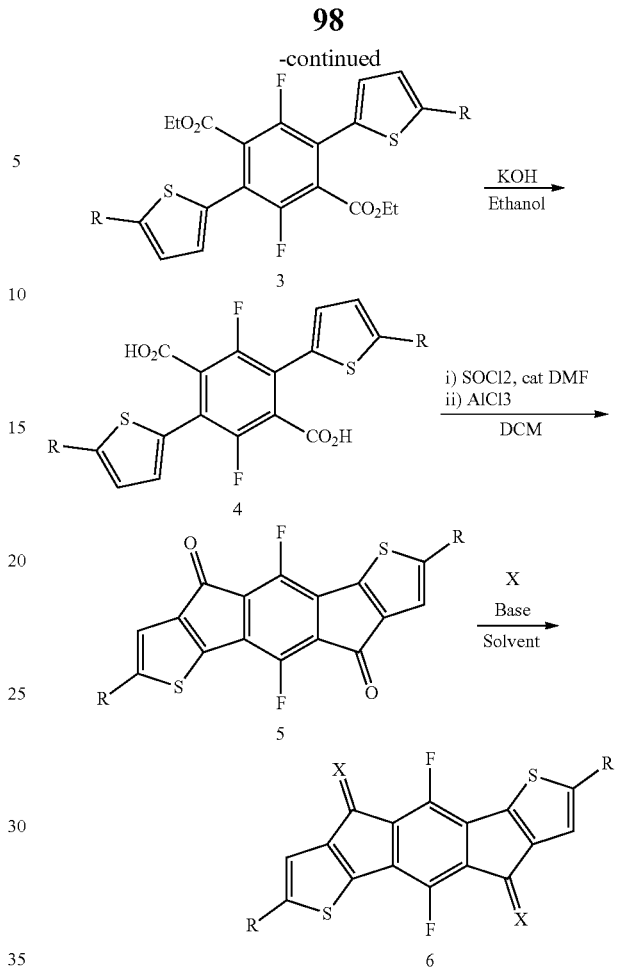

The hexasubstituted diethyl 2,5-dibromo-3,6-difluoro-terephthalate (2) is prepared by metalation of commercially available 1,4-dibromo-2,5-difluorobenzene (1), followed by quenching with ethyl chloroformate as disclosed in WO2015154845A1. Compound (2) is then reacted via a Stille cross-coupling with trimethyl(5-hexylthiophen-2-yl)stannane using tetrakis(triphenylphosphine) palladium(0) to give diethyl 2,5-difluoro-3,6-bis(5-hexylthiophen-2-yl)terephthalate (3). Trimethyl(5-hexylthiophen-2-yl)stannane is prepared by stannylation of commercially available 2-hexylthiophene using n-BuLi at −78° C. to lithiate followed by the addition of $Me_3SnCl$ solution. Formation of the ladder-type 2,7-dihexyl-5,10-difluoro-s- indaceno[1,2-b:5,6-b']dithiophene-4,9-dione (5) is achieved in 2 steps: 1) saponification of (3) using KOH in ethanol, 2) acylation of the resulting dicarboxylic acid followed by an intramolecular Friedl-crafts acylation with the lewis acid $AlCl_3$ and catalytic DMF. Knoevenagel condensation of (5) with malononitrile (recrystallized from ethanol) with pyridine as the base yields the 2,2'-(5,10-difluoro-2,7-dihexyl-s- indaceno[1,2-b:5,6-b']dithiophene-4,9-diylidene)dimalononitrile (6). The formation of compounds (3) to (6) can be achieved in analogy to the methods disclosed in *ACS Appl. Mater. Interfaces* 2017, 9, 8219-8232 and *J. Mater. Chem.*, 2010, 20, 7998-8004 for the non-fluorinated analogue.

A suitable and preferred synthesis route to IDT polymers is exemplarily shown below in Scheme 2, wherein R is a solubilizing group like for example alkyl as defined for $R^1$ above, X is an EWG as defined for $R^{T1}$ above, Y is for example a stannyl or borate group like SnMe₃ or B(OR)₂, and Ar is an aryl or heteroaryl group as defined for Ar⁵ above.

Scheme 2

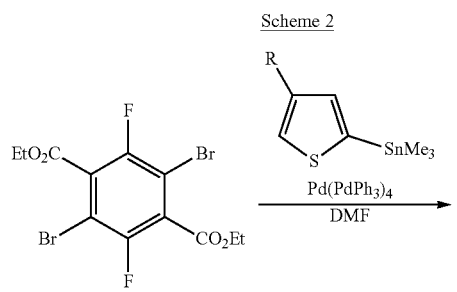

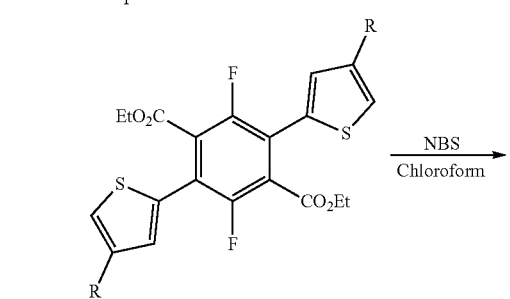

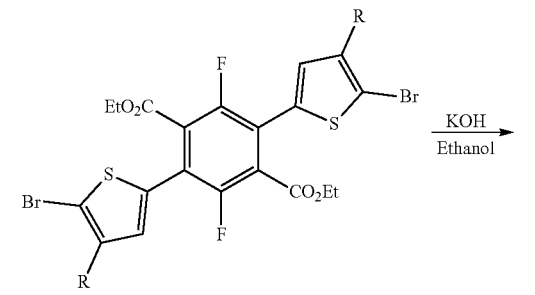

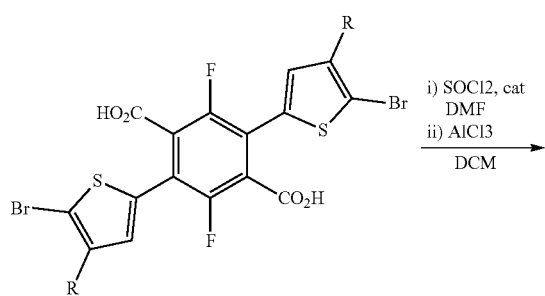

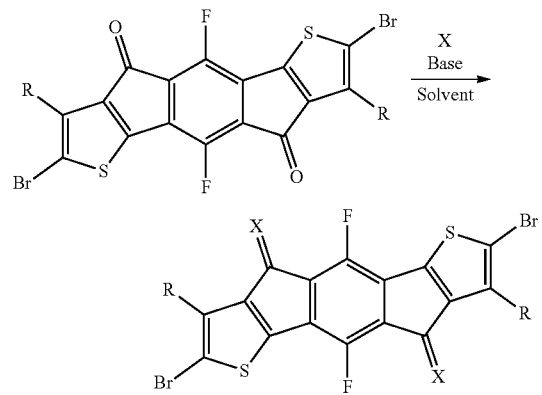

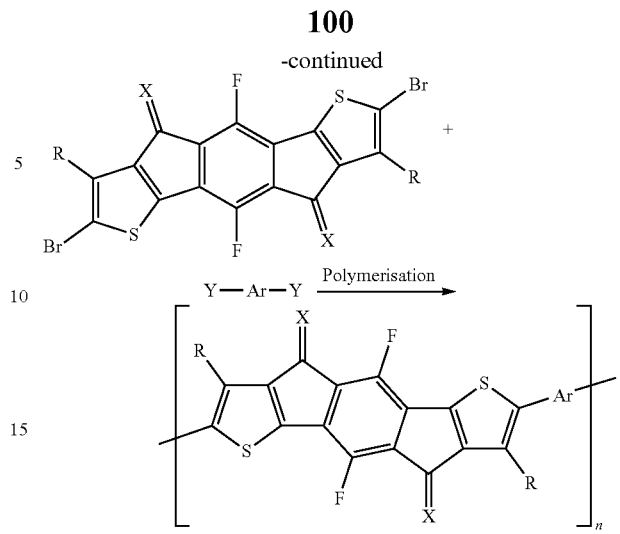

A suitable and preferred synthesis route to IDTT polymers is exemplarily shown below in Scheme 3, wherein R is a solubilizing group like for example alkyl as defined for R¹ above, X is an EWG as defined for $R^{T1}$ above, Y is for example a stannyl or borate group like SnMe₃ or B(OR)₂, and Ar is an aryl or heteroaryl group as defined for Ar⁵ above.

Scheme 3

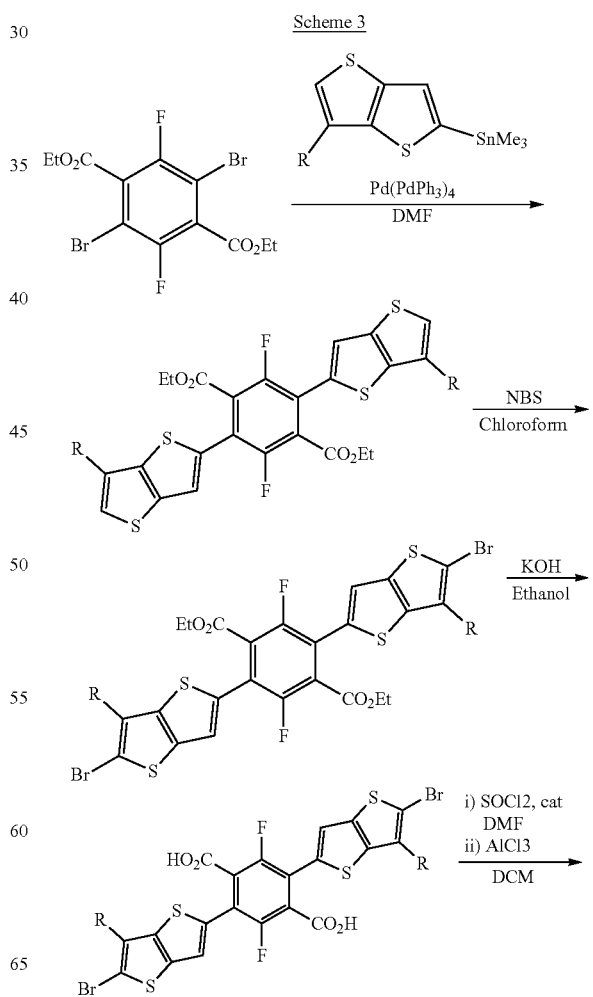

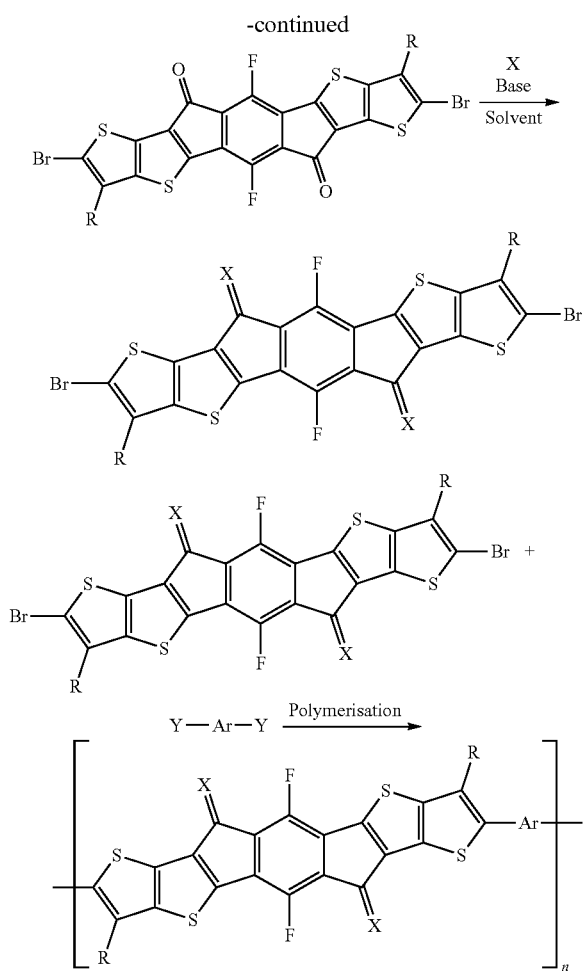

Novel methods of preparing compounds according to the present invention as described above and below are another aspect of the invention.

The compounds according to the present invention can also be used in compositions, for example together with monomeric or polymeric compounds having charge-transport, semiconducting, electrically conducting, photoconducting and/or light emitting semiconducting properties, or for example with compounds having hole blocking or electron blocking properties for use as interlayers or charge blocking layers in PSCs or OLEDs.

Thus, another aspect of the invention relates to a composition comprising one or more compounds according to the present invention and one or more small molecule compounds and/or polymers having one or more of a charge-transport, semiconducting, electrically conducting, photoconducting, hole blocking and electron blocking property.

These compositions blends can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more compounds according to the present invention or compositions as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluoro-toluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a compound according to the present invention can be carried out for example by photolithography, electron beam lithography or laser patterning.

For use as thin layers in electronic or electrooptical devices the compounds, compositions or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds according to the present invention are useful as charge transport, semiconducting, electrically conducting, photoconducting or light emitting materials in optical, electrooptical, electronic, electroluminescent or photoluminescent components or devices. In these devices, the compounds of the present invention are typically applied as thin layers or films.

Thus, the present invention also provides the use of the semiconducting compound or composition or layer in an electronic device. The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the present invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising compound or composition or organic semiconducting layer according to the present invention. Especially preferred devices are OFETs, TFTs, ICs, logic circuits, capacitors, RFID tags, OLEDs, OLETs, OPEDs, OPVs, PSCs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV, PSC and OPD devices, in particular OPD, PSC and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

For use in the photoactive layer of OPV or OPD devices the compounds according to the present invention are preferably used in a composition that comprises or contains, more preferably consists of, one or more p-type (electron donor) semiconductors and one or more n-type (electron acceptor) semiconductors.

The p-type semiconductor is for example constituted by a compound, preferably a conjugated polymer, according to the present invention, or another conjugated polymer.

The n-type semiconductor for example constituted by a compound, preferably a small molecule, according to the present invention, or is for example a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science, 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.*, 2004, 16, 4533).

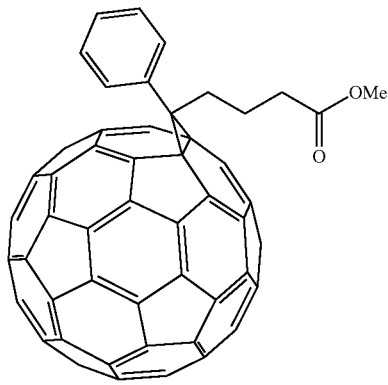

PCBM-$C_{60}$

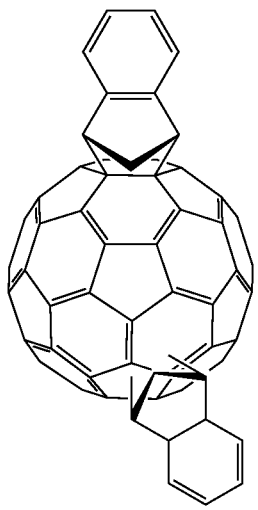

ICBA-$C_{60}$

Preferably the fullerene or substituted fullerene is selected from formula Full-I

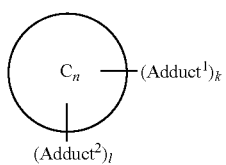

Full-I wherein $C_n$ denotes a fullerene composed of n carbon atoms, optionally with one or more atoms trapped inside, Adduct$^1$ is a primary adduct appended to the fullerene $C_n$ with any connectivity, Adduct$^2$ is a secondary adduct, or a combination of secondary adducts, appended to the fullerene $C_n$ with any connectivity, k is an integer $\geq 1$, and l is 0, an integer $\geq 1$, or a non- integer $> 0$.

In the formula Full-I and its subformulae, k preferably denotes 1, 2, 3 or, 4, very preferably 1 or 2.

The fullerene $C_n$ in formula Full-I and its subformulae may be composed of any number n of carbon atoms Preferably, in the compounds of formula XII and its subformulae the number of carbon atoms n of which the fullerene $C_n$ is composed is 60, 70, 76, 78, 82, 84, 90, 94 or 96, very preferably 60 or 70.

The fullerene $C_n$ in formula Full-I and its subformulae is preferably selected from carbon based fullerenes, endohedral fullerenes, or mixtures thereof, very preferably from carbon based fullerenes.

Suitable and preferred carbon based fullerenes include, without limitation, $(C_{60-Ih})[5,6]$fullerene, $(C_{70-D5h})[5,6]$fullerene, $(C_{76-D2'})[5,6]$fullerene, $(C_{84-D2'})[5,6]$fullerene, $(C_{84-D2d})[5,6]$fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, $Sc_3$N@$C_{80}$, $Y_3$N@$C_{80}$, $Sc_3C_2$@$C_{80}$ or a mixture of two or more of the aforementioned metallofullerenes.

Preferably the fullerene $C_n$ is substituted at a [6,6] and/or [5,6] bond, preferably substituted on at least one [6,6] bond.

Primary and secondary adduct, named "Adduct" in formula Full-I and its subformulae, is preferably selected from the following formulae

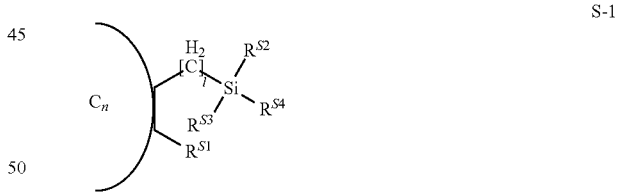

S-1

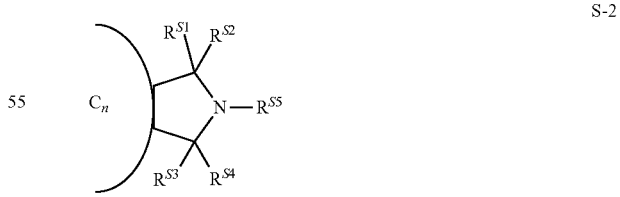

S-2

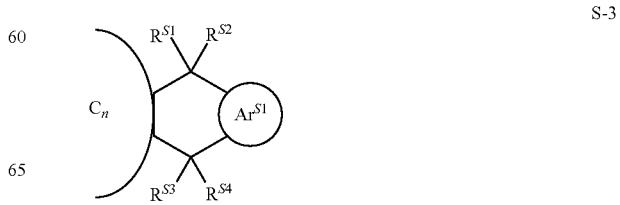

S-3

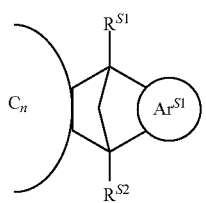

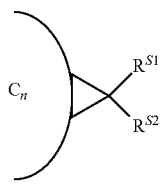

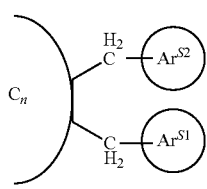

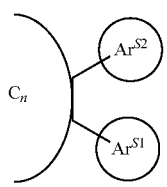

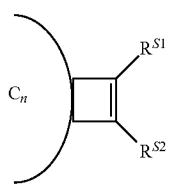

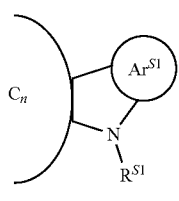

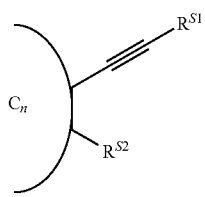

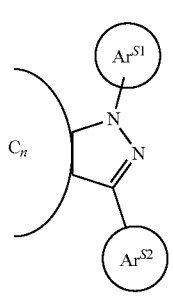

S-4

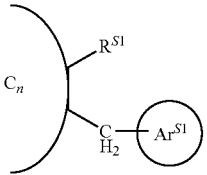

S-11

S-4

S-5

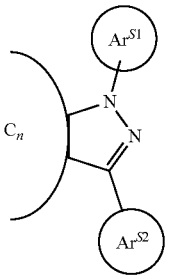

S-12

S-6

S-7

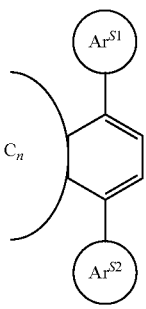

S-13

S-8

S-9

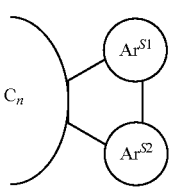

S-14

S-10 wherein $Ar^{S1}$, $Ar^{S2}$ denote, independently of each other, an aryl or heteroaryl group with 5 to 20, preferably 5 to 15, ring atoms, which is mono- or polycyclic, and which is optionally substituted by one or more identical or different substituents having one of the meanings of L as defined above and below, $R^{S1}$, $R^{S2}$, $R^{S3}$, $R^{S4}$ and $R^{S5}$ independently of each other denote H, CN or have one of the meanings of $R^S$ as defined above and below, l is 0 or an integer from 1 to 20, preferably 1 to 12.

Preferred compounds of formula Full-I are selected from the following subformulae:

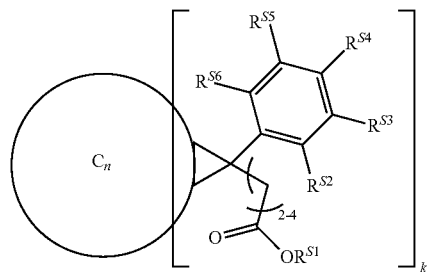
Full-Ia

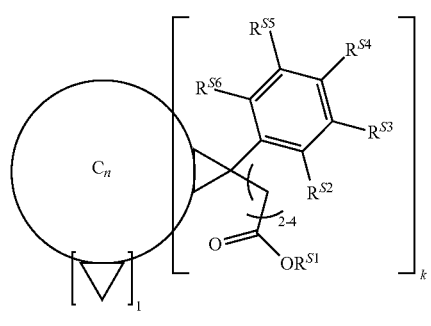
Full-Ib

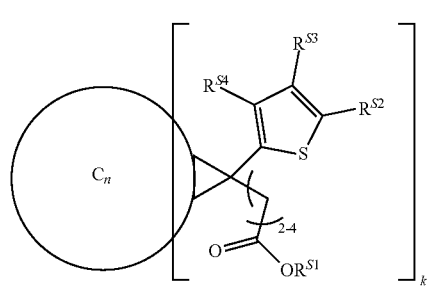
Full-Ic

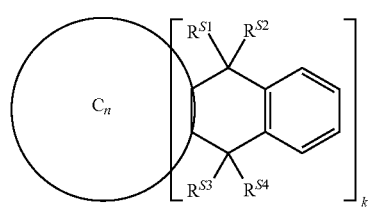
Full-Id

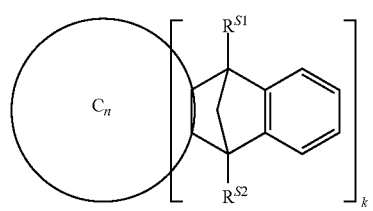
Full-Ie

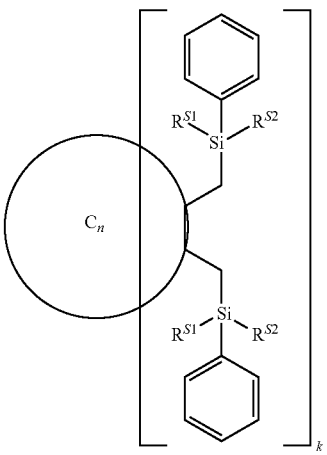
Full-If

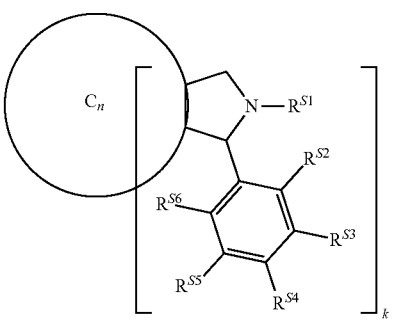
Full-Ig

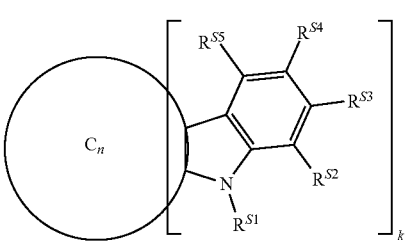
Full-Ih wherein
$R^{S1}$, $R^{S2}$, $R^{S3}$, $R^{S4}$ $R^{S5}$ and $R^{S6}$ independently of each other denote H or have one of the meanings of $R^S$ as defined above and below.

Most preferably the fullerene is PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-lh), or bis-oQDM-C60.

The OPV or OPD device preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an insulating polymer, like for example nafion, polyethyleneimine or polystyrene-sulphonate, an organic compound, like for example N,N'- diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly[(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a composition according to the present invention comprising a p-type OSC which is a conjugated polymer and an n-type OSC compound, the ratio polymer:n-type OSC compound is preferably from 5:1 to 1:5 by weight, more preferably from 3:1 to 1:3 by weight, most preferably 2:1 to 1:2 by weight.

The composition according to the present invention may also comprise a polymeric binder, preferably from 0.001 to 95% by weight. Examples of binder include polystyrene (PS), polydimethylsilane (PDMS), polypropylene (PP) and polymethylmethacrylate (PMMA).

A binder to be used in the formulation as described before, which is preferably a polymer, may comprise either an insulating binder or a semiconducting binder, or mixtures thereof, may be referred to herein as the organic binder, the polymeric binder or simply the binder.

Preferably, the polymeric binder comprises a weight average molecular weight in the range of 1000 to 5,000,000 g/mol, especially 1500 to 1,000,000 g/mol and more preferable 2000 to 500,000 g/mol. Surprising effects can be achieved with polymers having a weight average molecular weight of at least 10000 g/mol, more preferably at least 100000 g/mol.

In particular, the polymer can have a polydispersity index $M_w/M_n$ in the range of 1.0 to 10.0, more preferably in the range of 1.1 to 5.0 and most preferably in the range of 1.2 to 3.

Preferably, the inert binder is a polymer having a glass transition temperature in the range of −70 to 160° C., preferably 0 to 150° C., more preferably 50 to 140° C. and most preferably 70 to 130° C. The glass transition temperature can be determined by measuring the DSC of the polymer (DIN EN ISO 11357, heating rate 10° C. per minute).

The weight ratio of the polymeric binder to the compound according to the present invention is preferably in the range of 30:1 to 1:30, particularly in the range of 5:1 to 1:20 and more preferably in the range of 1:2 to 1:10.

According to a preferred embodiment the binder preferably comprises repeating units derived from styrene monomers and/or olefin monomers. Preferred polymeric binders can comprise at least 80%, preferably 90% and more preferably 99% by weight of repeating units derived from styrene monomers and/or olefins.

Styrene monomers are well known in the art. These monomers include styrene, substituted styrenes with an alkyl substituent in the side chain, such as α-methylstyrene and α-ethylstyrene, substituted styrenes with an alkyl substituent on the ring such as vinyltoluene and p-methylstyrene, halogenated styrenes such as monochlorostyrenes, dichlorostyrenes, tribromostyrenes and tetrabromostyrenes.

Olefin monomers consist of hydrogen and carbon atoms. These monomers include ethylene, propylene, butylenes, isoprene and 1,3-butadiene.

According to a preferred embodiment of the present invention, the polymeric binder is polystyrene having a weight average molecular weight in the range of 50,000 to 2,000,000 g/mol, preferably 100,000 to 750,000 g/mol, more preferably in the range of 150,000 to 600,000 g/mol and most preferably in the range of 200,000 to 500,000 g/mol.

Further examples of suitable binders are disclosed for example in US 2007/0102696 A1. Especially suitable and preferred binders are described in the following.

The binder should preferably be capable of forming a film, more preferably a flexible film.

Suitable polymers as binders include poly(1,3-butadiene), polyphenylene, polystyrene, poly(α-methylstyrene), poly(α-vinylnaphtalene), poly(vinyltoluene), polyethylene, cis-polybutadiene, polypropylene, polyisoprene, poly(4-methyl-1-pentene), poly (4-methylstyrene), poly(chorotrifluoroethylene), poly(2-methyl-1,3-butadiene), poly(p-xylylene), poly(α-α-α'-α' tetrafluoro-p-xylylene), poly[1,1-(2-methyl propane)bis(4-phenyl)carbonate], poly(cyclohexyl methacrylate), poly(chlorostyrene), poly(2,6-dimethyl-1,4-phenylene ether), polyisobutylene, poly(vinyl cyclohexane), poly(vinylcinnamate), poly(4-vinylbiphenyl), 1,4-polyisoprene, polynorbornene, poly(styrene-block-butadiene); 31% wt styrene, poly(styrene-block-butadiene-block-styrene); 30% wt styrene, poly(styrene-co-maleic anhydride) (and ethylene/butylene) 1-1.7% maleic anhydride, poly(styrene-block-ethylene/butylene-block-styrene) triblock polymer 13% styrene, poly(styrene-block-ethylene-propylene-block-styrene) triblock polymer 37% wt styrene, poly(styrene-block-ethylene/butylene-block-styrene) triblock polymer 29% wt styrene, poly(1-vinylnaphthalene), poly(1-vinylpyrrolidone-co-styrene) 64% styrene, poly(1-vinylpyrrolidone-co-vinyl acetate) 1.3:1, poly(2-chlorostyrene), poly(2-vinylnaphthalene), poly(2-vinylpyridine-co-styrene) 1:1, poly(4,5-Difluoro-2,2-bis(CF3)-1,3-dioxole-co-tetrafluoroethylene) Teflon, poly(4-chlorostyrene), poly(4-methyl-1-pentene), poly(4-methylstyrene), poly(4-vinylpyridine-co-styrene) 1:1, poly(alpha-methylstyrene), poly(butadiene-graft-poly(methyl acrylate-co-acrylonitrile)) 1:1:1, poly(butyl methacrylate-co-isobutyl methacrylate) 1:1, poly(butyl methacrylate-co-methyl methacrylate) 1:1, poly(cyclohexylmethacrylate), poly(ethylene-co-1-butene-co-1-hexene) 1:1:1, poly(ethylene-co-ethylacrylate-co-maleic anhydride); 2% anhydride, 32% ethyl acrylate, poly(ethylene-co-glycidyl methacrylate) 8% glycidyl methacrylate, poly(ethylene-co-methyl acrylate-co-glycidyl meth-acrylate) 8% glycidyl metha-crylate 25% methyl acrylate, poly(ethylene-co-octene) 1:1, poly(ethylene-co-propylene-co-5-methylene-2-norbornene) 50% ethylene, poly(ethylene-co-tetrafluoroethylene) 1:1, poly(isobutyl methacrylate), poly(isobutylene), poly(methyl methacrylate)-co-(fluorescein O-methacrylate) 80% methyl methacrylate, poly(methyl methacrylate-co-butyl methacrylate) 85% methyl methacrylate, poly(methyl methacrylate-co-ethyl acrylate) 5% ethyl acrylate, poly(propylene-co-butene) 12% 1-butene, poly(styrene-co-allyl alcohol) 40% allyl alcohol, poly(styrene-co-maleic anhydride) 7% maleic anhydride, poly(styrene-co-maleic anhydride) cumene terminated (1.3:1), poly(styrene-co-methyl methacrylate) 40% styrene, poly(vinyltoluene-co-alpha-methylstyrene) 1:1, poly-2-vinylpyridine, poly-4-vinylpyridine, poly-alpha-pinene, polymethylmethacrylate, polybenzylmethacrylate, polyethylmethacrylate, polyethylene, polyethylene terephthalate, polyethylene-co-ethylacrylate 18% ethyl acrylate, polyethylene-co-vinylacetate 12% vinyl acetate, polyethylene-graft-maleic anhydride 0.5% maleic anhydride, polypropylene, polypropylene-graft-maleic anhydride 8-10% maleic anhydride, polystyrene poly(styrene-block-ethylene/butylene-block-styrene) graft maleic anhydride 2% maleic anhydride 1:1:1 others, poly(styrene-block-butadiene) branched 1:1, poly(styrene-block-butadiene-block-styrene), 30% styrene, poly(styrene-block-isoprene) 10% wt styrene, poly(styrene-block-isoprene-block-styrene) 17% wt styrene, poly(styrene-co-4-chloromethylstyrene-co-4-methoxymethylstyrene 2:1:1, polystyrene-co-acrylonitrile 25% acrylonitrile, polystyrene-co-alpha-methylstyrene 1:1, polystyrene-co-butadiene 4% butadiene, polystyrene-co-butadiene 45% styrene, polystyrene-co-chloromethylstyrene 1:1, polyvinylchloride, polyvinylcinnamate, polyvinylcyclohexane, polyvinylidenefluoride, polyvinylidenefluoride-co-hexafluoropropylene assume 1:1, poly(styrene-block-ethylene/propylene-block-styrene) 30% styrene, poly(styrene-block-ethylene/propylene-block-styrene) 18% styrene, poly(styrene-block-ethylene/propylene-block-styrene) 13% styrene, poly(styrene-block ethylene block-ethylene/propylene-block styrene) 32% styrene, poly(styrene-block ethylene block-ethylene/propylene-block styrene) 30% styrene, poly(styrene-block-ethylene/butylene-block-styrene) 31% styrene, poly(styrene-block-ethylene/butylene-block-styrene) 34% styrene, poly(styrene-block-ethylene/butylene-block-styrene) 30% styrene, poly(styrene-block-ethylene/butylene-block-styrene) 60%, styrene, branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders to be used in the formulations as described before are polystryene, poly(α-methylstyrene), polyvinylcinnamate, poly(4-vinylbiphenyl), poly(4-methylstyrene), and polymethyl methacrylate. Most preferred insulating binders are polystyrene and polymethyl methacrylate.

The binder can also be selected from crosslinkable binders, like e.g. acrylates, epoxies, vinylethers, thiolenes etc. The binder can also be mesogenic or liquid crystalline.

The organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility of at least $10^{-5}$ $cm^2V^{-1}s^{-1}$, more preferably at least $10^{-4}$ $cm^2V^{-1}s^{-1}$.

A preferred semiconducting binder comprises a homopolymer or copolymer (including block-copolymer) containing arylamine (preferably triarylamine).

To produce thin layers in BHJ OPV devices the compounds, compositions and formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the mixture of a p-type OSC compound and an n-type OSC compound must be prepared. In the preparation of formulations, suitable solvent must be selected to ensure full dissolution of both component, p-type and n-type and take into account the boundary conditions (for example rheological properties) introduced by the chosen printing method.

Organic solvents are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the present invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic polymer or polymer blend, for example of PEDOT:PSS (poly(3,4-ethylenedioxythiophene):poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF or PFN,
  a low work function electrode, preferably comprising a metal like for example aluminium, serving as cathode,
  wherein at least one of the electrodes, preferably the anode, is transparent to visible light, and
  wherein the p-type semiconductor and/or the n-type semiconductor is a compound according to the present invention.

A second preferred OPV device according to the present invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising an organic polymer, polymer blend, metal or metal oxide like $TiO_x$, $ZnO_x$, Ca, Mg, poly(ethyleneimine), poly(ethyleneimine) ethoxylated or poly [(9,9-bis(3'-(N,N-dimethylamino)propyl)-2,7-fluorene)-alt-2,7-(9,9-dioctylfluorene)], a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ, an optional conducting polymer layer or hole transport layer, preferably comprising an organic polymer or polymer blend, metal or metal oxide, for example PEDOT:PSS, nafion, a substituted triaryl amine derivative like for example TBD or NBD, or $WO_x$, $MoO_x$, $NiO_x$, Pd or Au, an electrode comprising a high work function metal like for example silver, serving as anode, wherein at least one of the electrodes, preferably the cathode, is transparent to visible light, and wherein the p-type semiconductor and/or the n-type semiconductor is a compound according to the present invention.

In the OPV devices of the present invention the p-type and n-type semiconductor materials are preferably selected from the materials, like the compound/polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-octanedithiol, 1,8-diiodooctane, nitrobenzene, chloronaphthalene, and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

Another preferred embodiment of the present invention relates to the use of a compound or composition according to the present invention as dye, hole transport layer, hole blocking layer, electron transport layer and/or electron blocking layer in a DSSC or a perovskite-based solar cell (PSC), and to a DSSC or PSC comprising a compound or composition according to the present invention.

DSSCs and PSCs can be manufactured as described in the literature, for example in Chem. Rev. 2010, 110, 6595-6663, Angew. Chem. Int. Ed. 2014, 53, 2-15 or in WO2013171520A1

A preferred OE device according to the present invention is a solar cell, preferably a PSC, comprising a light absorber which is at least in part inorganic as described below.

In a solar cell comprising the light absorber according to the present invention there are no restrictions per se with respect to the choice of the light absorber material which is at least in part inorganic.

The term "at least in part inorganic" means that the light absorber material may be selected from metalorganic complexes or materials which are substantially inorganic and possess preferably a crystalline structure where single positions in the crystalline structure may be allocated by organic ions.

Preferably, the light absorber comprised in the solar cell according to the present invention has an optical band-gap ≤2.8 eV and ≥0.8 eV.

Very preferably, the light absorber in the solar cell according to the present invention has an optical band-gap ≤2.2 eV and ≥1.0 eV.

The light absorber used in the solar cell according to the present invention does preferably not contain a fullerene. The chemistry of fullerenes belongs to the field of organic chemistry. Therefore fullerenes do not fulfil the definition of being "at least in part inorganic" according to the present invention.

Preferably, the light absorber which is at least in part inorganic is a material having perovskite structure or a material having 2D crystalline perovskite structure.

The term "perovskite" as used above and below denotes generally a material having a perovskite crystalline structure or a 2D crystalline perovskite structure.

The term perovskite solar cell (PSC) means a solar cell comprising a light absorber which is a material having perovskite structure or a material having 2D crystalline perovskite structure.

The light absorber which is at least in part inorganic is without limitation composed of a material having perovskite crystalline structure, a material having 2D crystalline perovskite structure (e.g. CrystEngComm, 2010, 12, 2646-2662), $Sb_2S_3$ (stibnite), $Sb_2(S_xSe_{(x-1)})_3$, $PbS_xSe_{(x-1)}$, $CdS_xSe_{(x-1)}$, ZnTe, CdTe, $ZnS_xSe_{(x-1)}$, InP, FeS, $FeS_2$, $Fe_2S_3$, $Fe_2SiS_4$, $Fe_2GeS_4$, $Cu_2S$, CuInGa, $CuIn(Se_xS_{(1-x)})_2$, $Cu_3Sb_xBi_{(x-1)}$, $(S_ySe_{(y-1)})_3$, $Cu_2SnS_3$, $SnS_xSe_{(x-1)}$, $Ag_2S$, $AgBiS_2$, BiSI, BiSeI, $Bi_2(S_xSe_{(x-1)})_3$, $BiS_{(1-x)}Se_xI$, $WSe_2$, AlSb, metal halides (e.g. $BiI_3$, $Cs_2SnI_6$), chalcopyrite (e.g. $CuIn_xGa_{(1-x)}(S_ySe_{(1-y)})_2$), kesterite (e.g. $Cu_2ZnSnS_4$, $Cu_2ZnSn(Se_xS_{(1-x)})_4$, $Cu_2Zn(Sn_{1-x}Ge_x)S_4$) and metal oxide (e.g. CuO, $Cu_2O$) or a mixture thereof.

Preferably, the light absorber which is at least in part inorganic is a perovskite.

In the above definition for light absorber, x and y are each independently defined as follows: (0≤x≤1) and (0≤y≤1).

Very preferably, the light absorber is a special perovskite namely a metal halide perovskite as described in detail above and below. Most preferably, the light absorber is an organic-inorganic hybrid metal halide perovskite contained in the perovskite solar cell (PSC).

In one particularly preferred embodiment of the invention, the perovskite denotes a metal halide perovskite with the formula $ABX_3$, where A is a monovalent organic cation, a metal cation or a mixture of two or more of these cations B is a divalent cation and X is F, Cl, Br, I, $BF_4$ or a combination thereof.

Preferably, the monovalent organic cation of the perovskite is selected from alkylammonium, wherein the alkyl group is straight chain or branched having 1 to 6 C atoms, formamidinium or guanidinium or wherein the metal cation is selected from $K^+$, $Cs^+$ or $Rb^+$.

Suitable and preferred divalent cations B are $Ge^{2+}$, $Sn^{2+}$ or $Pb^{2+}$.

Suitable and preferred perovskite materials are $CsSnI_3$, $CH_3NH_3Pb(I_{1-x}Cl_x)_3$, $CH_3NH_3PbI_3$, $CH_3NH_3Pb(I_{1-x}Br_x)_3$, $CH_3NH_3Pb(I_{1-x}(BF_4)_x)_3$, $CH_3NH_3Sn(I_{1-x}Cl_x)_3$, $CH_3NH_3SnI_3$ or $CH_3NH_3Sn(I_{1-x}Br_x)_3$ wherein x is each independently defined as follows: (0<x≤1).

Further suitable and preferred perovskites may comprise two halides corresponding to formula $Xa_{(3-x)}Xb_{(x)}$, wherein Xa and Xb are each independently selected from Cl, Br, or I, and x is greater than 0 and less than 3.

Suitable and preferred perovskites are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskites are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The invention further relates to a solar cell comprising the light absorber, preferably a PSC, as described above and below, wherein the compound according to the present invention is employed as a layer between one electrode and the light absorber layer.

The invention further relates to a solar cell comprising the light absorber, preferably a PSC, as described above and below, wherein the compound according to the present invention is an n-type semiconductor and is comprised in an electron-selective layer.

The electron-selective layer is defined as a layer providing a high electron conductivity and a low hole conductivity favoring electron-charge transport.

The invention further relates to a solar cell comprising the light absorber, preferably a PSC, as described above and below, wherein the compound according to the present invention is a p-type semiconductor and is comprised in a hole-selective layer.

The hole-selective layer is defined as a layer providing a high hole conductivity and a low electron conductivity favoring hole-charge transport.

The invention further relates to a solar cell comprising the light absorber, preferably a PSC, as described above and below, wherein the compound according to the present invention is an n-type semiconductor and is employed as electron transport material (ETM) or as hole blocking material as part of the electron selective layer.

The invention further relates to a solar cell comprising the light absorber, preferably a PSC, as described above and below, wherein the compound according to the present invention is a p-type semiconductor and is employed as hole transport material (HTM) or as electron blocking material as part of the hole selective layer.

The device architecture of a PSC device according to the present invention can be of any type known from the literature.

A first preferred device architecture of a PSC device according to the present invention comprises the following layers (in the sequence from bottom to top):
  optionally a substrate which, in any combination, can be flexible or rigid and transparent, semi-transparent or non-transparent and electrically conductive or non-conductive;
  a high work function electrode, preferably comprising a doped metal oxide, for example fluorine-doped tin oxide (FTO), tin-doped indium oxide (ITO), or aluminium-doped zinc oxide;
  optionally an electron-selective layer which comprises one or more electron-transporting materials, which, in some cases, can also be a dense layer and/or be composed of nanoparticles, and which preferably comprises a metal oxide such as $TiO_2$, $ZnO_2$, $SnO_2$, $Y_2O_5$, $Ga_2O_3$, $SrTiO_3$, $BaTiO_3$ or combinations thereof;
  optionally a porous scaffold which can be conducting, semi-conducting or insulating, and which preferably comprises a metal oxide such as $TiO_2$, $ZnO_2$, $SnO_2$, $Y_2O_5$, $Ga_2O_3$, $SrTiO_3$, $BaTiO_3$, $Al_2O_3$, $ZrO_2$, $SiO_2$ or combinations thereof, and which is preferably composed of nanoparticles, nanorods, nanoflakes, nanotubes or nanocolumns;
  a layer comprising a light absorber which is at least in part inorganic, particularly preferably a metal halide perovskite as described above which, in some cases, can also be a dense or porous layer and which optionally partly or fully infiltrates into the underlying layer;
  optionally a hole selective layer which comprises one or more hole-transporting materials which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;
  and a back electrode which can be metallic, for example made of Au, Ag, Al, Cu, Ca, Ni or combinations thereof, or non-metallic and transparent, semi-transparent or non-transparent.
wherein the PSC device comprises at least one of
the electron-selective layer as described above which comprises a compound according to the present invention which is an n-type semiconductor,
the hole-selective layer as described above which comprises a compound according to the present invention which is a p-type semiconductor.

A second preferred device architecture of a PSC device according to the present invention comprises the following layers (in the sequence from bottom to top):
  optionally a substrate which, in any combination, can be flexible or rigid and transparent, semi-transparent or non-transparent and electrically conductive or non-conductive;
  a high work function electrode, preferably comprising a doped metal oxide, for example fluorine-doped tin oxide (FTO), tin-doped indium oxide (ITO), or aluminium-doped zinc oxide;
  optionally a hole injection layer which, for example, changes the work function of the underlying electrode, and/or modifies the surface of the underlying layer and/or helps to planarize the rough surface of the underlying layer and which, in some cases, can also be a monolayer;
  a hole selective layer, which comprises one or more hole-transporting materials, and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;
  a layer comprising a light absorber which is at least in part inorganic, particularly preferably a metal halide perovskite as described or preferably described above;
  optionally an electron-selective layer, which comprises one or more electron-transporting materials, which, in some cases, can also be a dense layer and/or be composed of nanoparticles, and which, for example, can comprise a metal oxide such as $TiO_2$, $ZnO_2$, $SnO_2$, $Y_2O_5$, $Ga_2O_3$, $SrTiO_3$, $BaTiO_3$ or combinations thereof, and/or which can comprise a substituted fullerene, for example [6,6]-phenyl C61-butyric acid methyl ester, and/or which can comprise a molecular, oligomeric or polymeric electron-transport material, for example 2,9-Dimethyl-4,7-diphenyl-1,10-phenanthroline, or a mixture thereof;
and a back electrode which can be metallic, for example made of Au, Ag, Al, Cu, Ca, Ni or combinations thereof, or non-metallic and transparent, semi-transparent or non-transparent,
wherein the PSC device comprises at least one of
the electron-selective layer as described above which comprises a compound according to the present invention which is an n-type semiconductor,
the hole-selective layer as described above which comprises a compound according to the present invention which is a p-type semiconductor.

To produce electron- or hole-selective layers in PSC devices according to the present invention, the compounds according to the present invention, optionally together with other compounds or additives in the form of blends or mixtures, may be deposited by any suitable method. Liquid coating of devices is more desirable than vacuum deposition techniques. Solution deposition methods are especially preferred. Formulations comprising the compounds according to the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot die coating or pad printing. For the fabrication of PSC devices and modules, deposition techniques for large area coating are preferred, for example slot die coating or spray coating.

Formulations that can be used to produce electron- or hole-selective layers in optoelectronic devices according to the present invention, preferably in PSC devices comprise one or more compounds according to the present invention or preferred embodiments as described above in the form of blends or mixtures optionally together with one or more further electron transport materials and/or hole blocking materials and/or binders and/or other additives as described above and below, and one or more solvents.

The formulation may include or comprise, essentially consist of or consist of the said necessary or optional constituents as described above or below. All compounds or components which can be used in the formulations are either known or commercially available, or can be synthesised by known processes.

The formulation as described before may be prepared by a process which comprises:
(i) first mixing a compound according to the present invention, optionally a binder or a precursor of a binder as described before, optionally a further electron transport material, optionally one or more further additives as described above and below and a solvent or solvent mixture as described above and below and
(ii) applying such mixture to a substrate; and optionally evaporating the solvent(s) to form an electron selective layer according to the present invention.

In step (i) the solvent may be a single solvent for the compound according to the present invention and the organic binder and/or further electron transport material may each be dissolved in a separate solvent followed by mixing the resultant solutions to mix the compounds.

Alternatively, the binder may be formed in situ by mixing or dissolving a compound according to the present invention in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound according to the present invention in a suitable solvent as described before, and the solution deposited for example by dipping, spraying, painting or printing it on a substrate to form a liquid layer and then removing the solvent to leave a solid layer. It will be appreciated that solvents are chosen which are able to dissolve all ingredients of the formulation, and which upon evaporation from the solution blend give a coherent defect free layer.

Besides the said components, the formulation as described before may comprise further additives and processing assistants. These include, inter alia, surface-active substances (surfactants), lubricants and greases, additives which modify the viscosity, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

Additives can be used to enhance the properties of the electron selective layer and/or the properties of any of the neighbouring layers and/or the performance of the optoelectronic device according to the present invention. Additives can also be used to facilitate the deposition, the processing or the formation of the electron selective layer and/or the deposition, the processing or the formation of any of the neighbouring layers. Preferably, one or more additives are used which enhance the electrical conductivity of the electron selective layer and/or passivate the surface of any of the neighbouring layers.

Suitable methods to incorporate one or more additives include, for example exposure to a vapor of the additive at atmospheric pressure or at reduced pressure, mixing a solution or solid containing one or more additives and a material or a formulation as described or preferably described before, bringing one or more additives into contact with a material or a formulation as described before, by thermal diffusion of one or more additives into a material or a formulation as described before, or by ion-implantantion of one or more additives into a material or a formulation as described before.

Additives used for this purpose can be organic, inorganic, metallic or hybrid materials. Additives can be molecular compounds, for example organic molecules, salts, ionic liquids, coordination complexes or organometallic compounds, polymers or mixtures thereof. Additives can also be particles, for example hybrid or inorganic particles, preferably nanoparticles, or carbon based materials such as fullerenes, carbon nanotubes or graphene flakes.

Examples for additives that can enhance the electrical conductivity are for example halogens (e.g. $I_2$, $Cl_2$, $Br_2$, $ICl$, $ICl_3$, $IBr$ and $IF$), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$), cations (e.g. $H^+$, $Li^+$, $Na^+$, $K^+$, $Rb^+$, $Cs^+$, $Co^{3+}$ and $Fe^{3+}$), $O_2$, redox active salts (e.g. $XeOF_4$, $(NO_2^+)(SbF_6^-)$, $(NO_2^+)(SbCl_6^-)$, $(NO_2^+)(BF_4^-)$, $NOBF_4$, $NOPF_6$, $AgClO_4$, $H_2IrCl_6$ and $La(NO_3)_3 \cdot 6H_2O$), strongly electron-accepting organic molecules (e.g. 2,3,5,6-tetrafluoro-7,7,8,8-tetracyanoquinodimethane (F4-TCNQ)), transition metal oxides (e.g. $WO_3$, $Re_2O_7$ and $MoO_3$), metal- organic complexes of cobalt, iron, bismuth and molybdenum, (p-$BrC_6H_4)_3NSbCl_6$, bismuth (III) tris(trifluoroacetate), $FSO_2OOSO_2F$, acetylcholine, $R_4N^+$, (R is an alkyl group), $R_4P^+$(R is a linear or branched alkyl group 1 to 20), $R_6As^+$(R is an alkyl group), $R_3S^+$(R is an alkyl group) and ionic liquids (e.g. 1-Ethyl-3-methylimidazolium bis(trifluoromethylsulfonyl)imide). Suitable cobalt complexes beside of tris(2-(1H-pyrazol-1-yl)-4-tert-butylpyridine)-cobalt(II) tris(bis(trifluoromethylsulfonyl) imide)) are cobalt complex salts as described in WO 2012/114315, WO 2012/114316, WO 2014/082706, WO 2014/082704, EP 2883881 or JP 2013-131477.

Suitable lithium salts are beside of lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluorophosphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl) imide.

Preferably, the formulation comprises from 0.1 mM to 50 mM, preferably from 5 to 20 mM of the lithium salt.

Suitable device structures for PSCs comprising a compound according to the present invention and a mixed halide perovskite are described in WO 2013/171517, claims 52 to 71 and claims 72 to 79, which is entirely incorporated herein by reference.

Suitable device structures for PSCs comprising a compound formula and a dielectric scaffold together with a perovskite are described in WO 2013/171518, claims 1 to 90 or WO 2013/171520, claims 1 to 94 which are entirely incorporated herein by reference.

Suitable device structures for PSCs comprising a compound according to the present invention, a semiconductor and a perovskite are described in WO 2014/020499, claims 1 and 3 to 14, which is entirely incorporated herein by reference The surface- increasing scaffold structure described therein comprises nanoparticles which are applied and/or fixed on a support layer, e.g. porous $TiO_2$.

Suitable device structures for PSCs comprising a compounds of formula and comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

The invention further relates to a method of preparing a PSC as described above or below, the method comprising the steps of:
providing a first and a second electrode;
providing an electron-selective layer and/or hole-selective layer at least one of which comprises a compound according to the present invention.

The invention relates furthermore to a tandem device comprising at least one device according to the present invention as described above and below. Preferably, the tandem device is a tandem solar cell.

The tandem device or tandem solar cell according to the present invention may have two semi-cells wherein one of the semi cells comprises the compounds, oligomers or polymers in the active layer as described or preferably described above. There exists no restriction for the choice of the other type of semi cell which may be any other type of device or solar cell known in the art.

There are two different types of tandem solar cells known in the art. The so called 2-terminal or monolithic tandem solar cells have only two connections. The two subcells (or synonymously semi cells) are connected in series. Therefore, the current generated in both subcells is identical (current matching). The gain in power conversion efficiency is due to an increase in voltage as the voltages of the two subcells add up. The other type of tandem solar cells is the so called 4-terminal or stacked tandem solar cell. In this case, both subcells are operated independently. Therefore, both subcells can be operated at different voltages and can also generate different currents. The power conversion efficiency of the tandem solar cell is the sum of the power conversion efficiencies of the two subcells.

The invention furthermore relates to a module comprising a device according to the present invention as described before or preferably described before.

The compounds and compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound and compositions according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the present invention and thus the processability of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
wherein the semiconducting layer comprises a compound according to the present invention.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, Synth. Metals, 2000, 111-112, 31-34, Alcala et al., J. Appl. Phys., 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., Science, 1998, 279, 835-837.

A further aspect of the invention relates to both the oxidised and reduced form of the materials according to the present invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R^4N^+$, (R is an alkyl group), $R^4P^+$(R is an alkyl group), $R_6As^+$(R is an alkyl group), and $R_3S^+$(R is an alkyl group).

The conducting form of the materials according to the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., Nat. Photonics, 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows.

The materials according to the present invention may also be combined with photoisomerisable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

Example 1

Diethyl 2,5-dibromo-3,6-difluoroterephthalate (2)

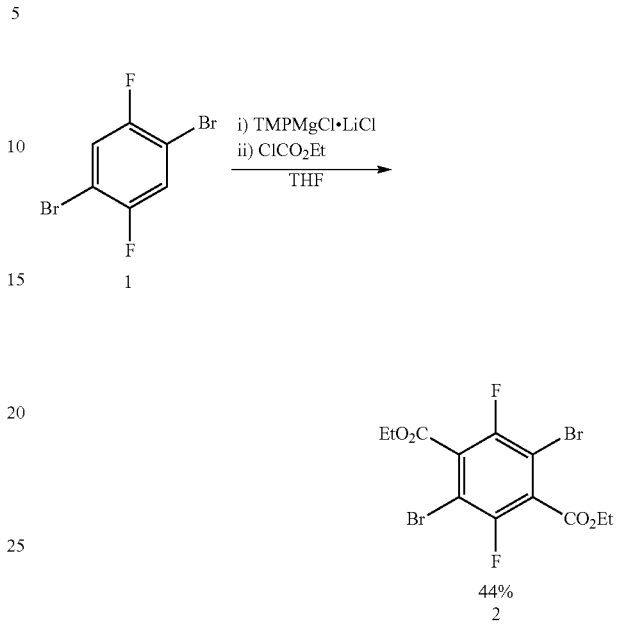

To a 1.0 M solution (THF 1:1 toluene) of 2,2,6,6-tetramethylpiperidinylmagnesium chloride lithium chloride complex (100 cm$^3$, 100 mmol) at −40° C. under inert atmosphere was added a solution of 1,4-dibromo-2,5-difluoro-benzene (11.82 g, 43.48 mmol) in anhydrous THF (150 cm$^3$) over 30 minutes via syringe pump. The reaction mixture was stirred at −40° C. for 5 hours before ethyl chloroformate (9.98 cm$^3$, 104 mmol) was added in one portion. The mixture was allowed to warm to 23° C. overnight. Aqueous hydrochloric acid (1.0 M, 200 cm$^3$) was added and the mixture stirred at 23° C. for 30 minutes. The product was extracted with diethyl ether (3×50 cm$^3$). The combined organics were dried over anhydrous magnesium sulphate, filtered and the solvent removed in vacuo. The crude product was triturated with n-pentane to form a suspension. The solid was filtered and washed with cold n-pentane, collected and dried under vacuum to give 2,5-dibromo-3,6-difluoro-terephthalic acid diethyl ester (8.03 g, 44%) as a cream solid. $^1$H NMR (300 MHz, CDCl$_3$) 1.41 (6H, t, $^3$J=7 Hz, CH$_3$), 4.47 (4H, q, $^3$J=7 Hz, CH$_2$) $^{19}$F NMR 108.70 (2F, s, CF)

Diethyl 2,5-difluoro-3,6-bis(5-hexylthiophen-2-yl)terephthalate (3)

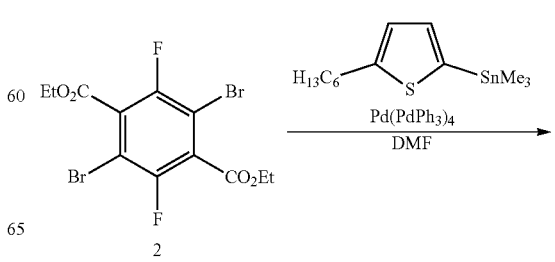

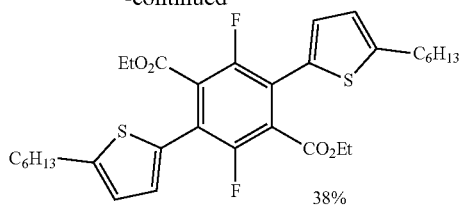

3 38%

A mixture of 2,5-dibromo-3,6-difluoroterephthalic acid diethyl ester (2.9 g, 6.9 mmol) and trimethylthiophen-2-yl-stannane (6.0 g, 16 mmol) in anhydrous DMF (50 cm³) was degassed for 45 mins. Tetrakis(triphenylphosphine)palladium(0) (0.4 g) was added and the mixture degassed for a further 15 mins. The mixture was stirred at 100° C. for 17 hours. After cooling to RT, the reaction was diluted with DCM (100 cm³) and the crude reaction mixture passed through a plug of 15% KF in silica, eluting with DCM. The solvent was concentrated in vacuo. DCM (100 cm³) was added and the organic phase washed with water (4×50 cm³) and brine (50 cm³). The combined organics were dried over anhydrous magnesium sulfate, filtered and the solvent removed in vacuo. The crude was purified by silica gel chromatography (petroleum ether 2:1 DCM) to give diethyl 2,5-difluoro-3,6-bis(5-hexylthiophen-2-yl)terephthalate (1.57 g, 38%) as a pale orange solid. ¹H NMR (300 MHz, CDCl₃) 0.89 (6H, t, ³J=7.2 Hz alkyl CH₃), 1.18 (6H, t, ³J=7 Hz, ester CH₃), 1.29 (12H, m, alkyl CH₂), 1.66 (4H, m, alkyl CH₂), 2.83 (4H, t, ³J=7.5 Hz alkyl CH₂), 4.26 (4H, q, ³J=7 Hz, ester CH₂), 6.76 (2H, d, ³J=7 Hz, Ar H), 7.00 (2H, d, ³J=7 Hz, Ar H) ¹⁹F NMR 119.94 (2F, s, CF).

2,5-bis(5-hexylthiophen-2-yl)-3,6-difluorotereph-thalic acid (4)

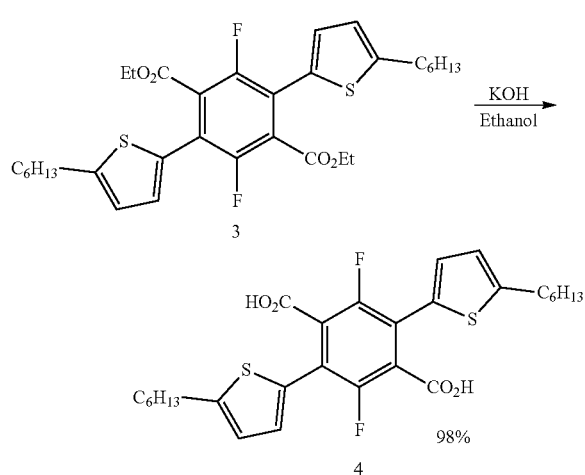

Diethyl 2,5-difluoro-3,6-bis(5-hexylthiophen-2-yl)terephthalate (1.5 g, 2.37 mmol) was suspended in ethanol (30 cm³) and KOH (1.06 g, 19.00 mmol) was added as a single portion. The suspension was refluxed overnight. Initially forming a suspension before the formation of a solution. The reaction was cooled to RT and aqueous hydrochloric acid (2.0 M, 75 cm³) added with stirring for 5 mins. The resulting precipitate was filtered, washed with plenty of water and dried in an oven at 140° C. to give 1.32 g (98%) of greenish solid. ¹H NMR (300 MHz, DMSO-d⁶) 0.8 (6H, t, ³J=7 Hz CH₃), 1.29 (12H, m, CH₂), 1.62 (4H, m, alkyl CH₂), 2.83 (4H, t, ³J=7.5 Hz CH₂), 6.93 (2H, d, ³J=3.5 Hz, Ar H), 7.13 (2H, d, ³J=3.5 Hz, Ar H) ¹⁹F NMR 116.18 (2F, s, CF).

2,7-dihexyl-5,10-difluoro-s-indaceno[1,2-b:5,6-b'] dithiophene-4,9-dione (5)

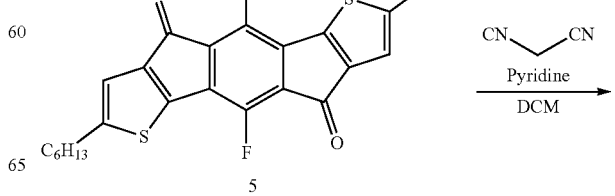

2,5-Difluoro-3,6-di-(5-hexylthiophen-2-yl-terephthalic acid (1.2 g, 2.24 mmol) was suspended in anhydrous DCM (25 cm³) and catalytic amount of anhydrous DMF (0.1 cm³; 1.12 mmol). Thionyl chloride (0.98 cm³, 13.47 mmol) was added dropwise over 15 minutes. The reaction was heated to 50° C. overnight. After cooling to RT the solvent was removed under reduced pressure to give an orange oil which is used in the next step without further purification.

The acyl chloride was redissolved in anhydrous DCM (50 cm³) and then added to a suspension of anhydrous AlCl₃ (1.52 g) in DCM (50 cm³) at 0° C. The resultant mixture was allowed to warm to RT and stirred overnight. The mixture was poured into cold aqueous hydrochloric acid (2.0 M, 100 cm³), causing a deep blue precipitate to form which was collected by filtration. Washing with aqueous hydrochloric acid (2.0 M), water, and acetone followed by drying in vacuo afforded a cyan blue solid (0.89 g, 80%). ¹H NMR (300 MHz, CDCl₃) 0.89 (6H, t, ³J=6.7 Hz, CH₃), 1.33 (12H, m, CH₂), 1.69 (4H, m, CH₂), 2.80 (4H, t, ³J=7.5 Hz, CH₂), 6.83 (2H, s, Ar H) ¹⁹F NMR 129.99 (2F, s, CF), ES-TOF MS (M+, m/z): 498.14 IR (cm⁻¹) 1708 (C=O).

2,2'-(5,10-difluoro-2,7-dihexyl-s-indaceno[1,2-b:5,6-b']dithiophene-4,9-diylidene)dimalononitrile (6)

-continued

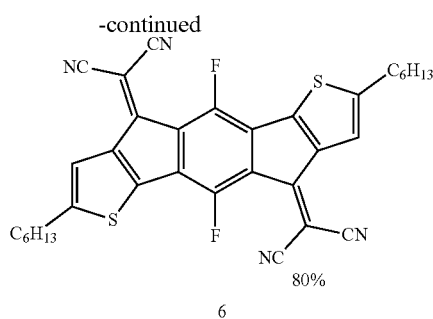

6

80%

2,7-dihexyl-5,10-difluoro-s-indaceno[1,2-b:5,6-b']dithiophene-4,9-dione (250 mg, 0.50 mmol) and malononitrile (100 mg, 1.5 mmol) were dissolved in anhydrous DCM (40 cm$^3$). Pyridine (0.1 cm$^3$) was added and the mixture stirred overnight at RT. Aqueous hydrochloric acid (2.0 M, 40 cm$^3$) was added and the resulting precipitate filtered. Washing with aqueous hydrochloric acid (2.0 M), water, and acetone followed by drying in vacuo afforded a deep green fibrous solid (239 mg, 80%). $^1$H NMR (300 MHz, CDCl$_3$) 0.90 (6H, t, $^3$J=6.9 Hz, CH$_3$), 1.33 (12H, m, CH$_2$), 1.70 (4H, m, CH$_2$), 2.84 (4H, t, $^3$J=7.5 Hz, CH$_2$), 7.34 (2H, s, Ar H) $^{13}$C NMR (101 MHz, CDCl$_3$) 155.27, 152.64, 149.39, 146.76, 144.68, 139.64, 120.46, 113.53, 112.34, 82.07, 77.16, 31.59, 31.41, 31.09, 28.78, 22.65, 14.11, 1.17. $^{19}$F NMR 108.18 (2F, s, CF), ES-TOF MS (M+, m/z): 594.17 IR (cm$^{-1}$) 2226 (C=O).

Field-Effect Transistor Fabrication and Measurements

Organic thin film transistors (OTFTs) were fabricated in bottom-contact top-gate (BC-TG) configuration. Gold source-drain electrodes of 40 nm were deposited via thermal evaporation in high vacuum (10$^{-6}$ mbar) through shadow masks resulting channel lengths in the range of 30-100 nm and width 1 mm. The organic semiconductor small molecule was deposited from 5 mg/ml solution in anhydrous chlorobenzene. Prior to the semiconductor deposition both source-drain substrate and solution were heated at 100° C. Small molecule was spin coated with spin speed of 2000 rpm for 30 sec and then annealed at various temperatures for 15 minutes. 900 nm of CYTOP were used as the dielectric layer followed by 40 nm of thermal evaporated aluminum which formed the gate electrode. Device fabrication and electrical measurements were performed in a nitrogen glovebox. Transistor characterization was carried out using an Agilent B2902 semiconductor parameter analyzer.

Field-effect mobility was calculated in the saturation regime from the slope of the square root of the drain current ($V_d$>($V_g$-$V_0$)) using equation (1).

$$\mu_s = \frac{2L}{wC_i}\left(\frac{\partial\sqrt{I_{D,S}}}{\partial V_G}\right)^2 \quad (1)$$

where W is the channel width, L the channel length, $C_i$ the capacitance of insulating layer, $V_g$ the gate voltage, and $\mu_{sat}$ is the charge carrier mobility in the saturation regime.

Linear field effect mobility was calculated from equation (2)

$$\mu_l = \frac{L}{wC_iV_D}\left(\frac{\partial I_{D,l}}{\partial V_G}\right) \quad (2)$$

Table 1 shows the transistor parameters such as the threshold voltage ($V_T$), charge carrier mobility μ in the linear and saturation regime, and on-off ratio $I_{on/off}$, for OTFT devices using compound (6) of Example 1 as organic semiconductor. The values are extracted from 7 devices with channel lengths 30-50 μm and width 1000 μm, and wherein the OSC film was annealed at 100, 150 and 200° C. respectively.

TABLE 1

| Annealing Temp. | $V_T$ (V) | $\mu_{lin}$ (cm$^2$/Vs) | $\mu_{sat}$ (cm$^2$/Vs) | $I_{ON/OFF}$ |
|---|---|---|---|---|
| 100° C. | 8.16 ± 2.13 | 0.116 ± 0.010 | 0.33 ± 0.02 | 10$^2$ |
| 150° C. | 5.66 ± 1.86 | 0.106 ± 0.008 | 0.31 ± 0.021 | 10$^2$-10$^3$ |
| 200° C. | 3.78 ± 1.06 | 0.055 ± 0.008 | 0.13 ± 0.02 | 10$^2$-10$^3$ |

It can be seen that compound of Example 6 shows good transistor performance. By annealing the OSC film it is possible to reduce the threshold voltage while keeping a high on/off current ratio.

The invention claimed is:

1. A compound comprising a unit of formula I

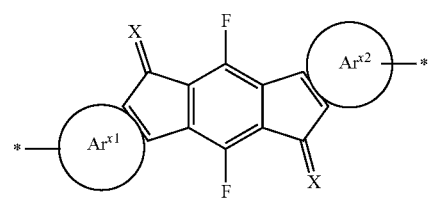

wherein X, Ar$^{x1}$ and Ar$^{x2}$, independently of each other and on each occurrence identically or differently, have the following meanings X is selected from the group consisting of the following formulae, wherein Q denotes an sp$^2$ C atom that is attached to the indacene core in formula I via the C=C double bond

Xa

Xb

Xc

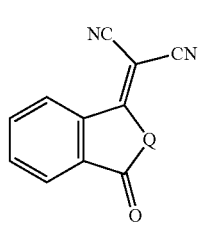
Xd

-continued
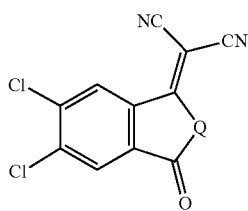
Xe
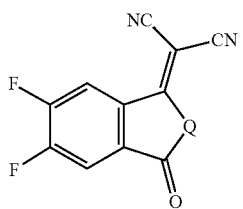
Xf
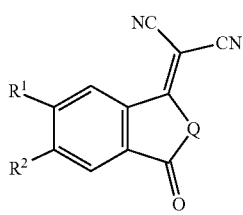
Xg
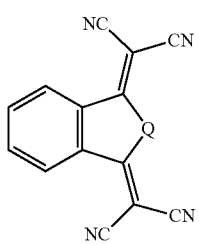
Xh
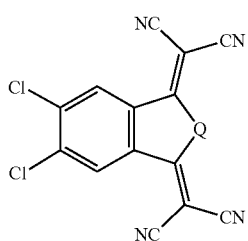
Xi
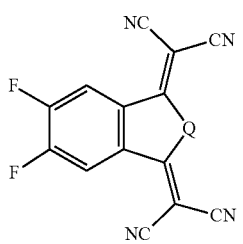
Xk
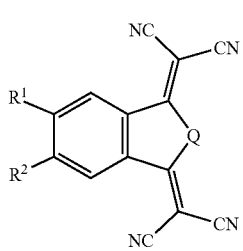
Xl
-continued
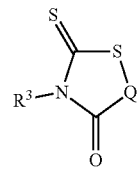
Xm
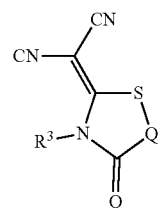
Xn
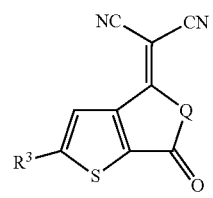
Xo
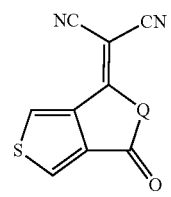
Xp
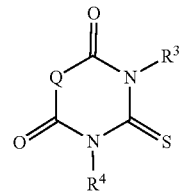
Xq
Ar$^{x1}$ is selected from the group consisting of the following formulae
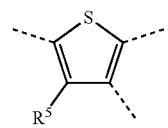
A1a1
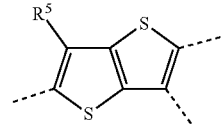
A1b1
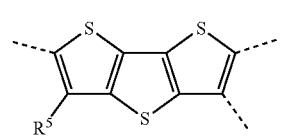
A1c1

-continued

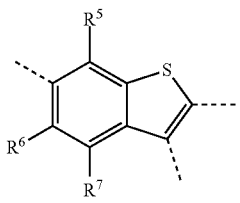
A1d1

Ar$^{x2}$ is selected from the group consisting of the following formulae

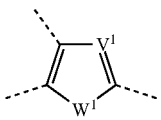
A2a

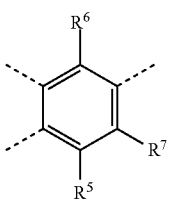
A2b

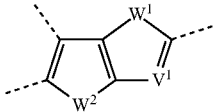
A3c

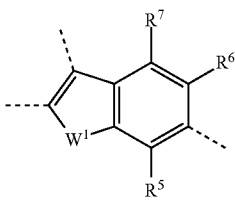
A2d

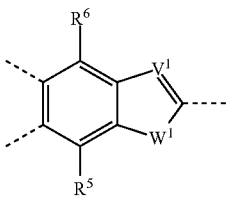
A2e

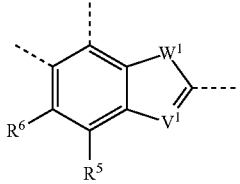
A2f

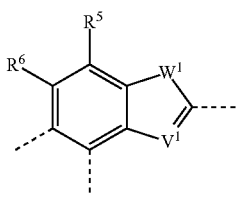
A2g

-continued

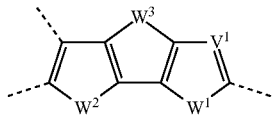
A2h

V$^1$ CR$^5$ or N,

W$^1$, W$^2$ S, O, Se or C=O,

W$^3$ S, O or NR$^0$,

R$^{1-7}$ H, F, Cl, CN, or straight-chain, branched or cyclic alkyl with 1 to 30 C atoms, in which one or more CH$_2$ groups are optionally replaced by -O-, -S-, —C(=O)—, -C(=S)-, -C(=O)—O—, -O—C(=O)—, -NR$^0$ —, -SiR$^0$R$^{00}$-, -CF$_2$-, -CR$^0$=CR$^{00}$-, -CY$^1$-CY$^2$- or -C≡C- in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, Y$^1$, Y$^2$ H, F, Cl or CN, L F, Cl, -NO$_2$, -CN, -NC, -NCO, -NCS, -OCN, -SCN, R$^0$, OR$^0$, SR$^0$, -C(=O)X$^0$, -C(=O) R$^0$ , -C(=O)—OR$^0$, -O—C(=O)—R$^0$ , -NH$_2$, -NHR$^0$, -NR$^0$ R$^{00}$, -C(=O)NHR$^0$, -C(=O)NR$^0$ R$^{00}$, -SO$_3$R0 , -SO$_2$R$^0$ , -OH, -NO$_2$, -CF$_3$, -SF$_5$, or optionally substituted silyl, or carbyl or hydrocarbyl with 1 to 30 C atoms that is optionally substituted and optionally comprises one or more hetero atoms, preferably F, -CN, R$^0$ , -OR$^0$, -SR$^0$, -C(=O)—R$^0$ , -C(=O)—OR$^0$, -O-C(=O)—R$^0$ , -O—C(=O)—OR$^0$, -C(=O)—NHR$^0$, or -C(=O)—NR$^0$ R$^{00}$, R$^0$, R$^{00}$ H or straight-chain or branched alkyl with 1 to 20 C atoms that is optionally fluorinated, X$^0$ halogen, preferably F or Cl.

2. The compound according to claim 1, characterized in that in the units of formula I Ar$^{x2}$ is selected from the following formulae and their mirror images

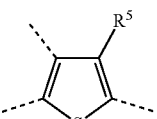
A2a1

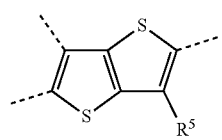
A2b1

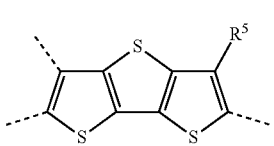
A2c1

-continued

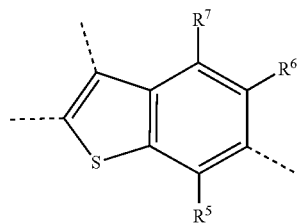

A2d1 wherein $R^{5-7}$ have the meanings given in claim 1.

3. The compound according to claim 1, characterized in that it is selected from formula S1

$$T^1\text{-}(Ar^{13})_{c1}\text{-}[(Ar^{11})_{a1}\text{-}U\text{-}(Ar^{12})_{b1}\text{-}]_{e1}(Ar^{14})_{d1}\text{-}T^2 \quad \text{S1}$$

wherein the individual radicals, independently of each other and on each occurrence identically or differently, have the following meanings U a unit of formula I as defined in claim 1, $Ar^{11-14}$ arylene or heteroarylene that has 5 to 20 ring atoms, is mono- or polycyclic, does optionally contain fused rings, is unsubstituted or substituted by one or more identical or different groups RS, and is different from formula I, or $CY^1=CY^2$- or -C≡C-, $T^1$, $T^2$ one of the meanings given for $R^1$ in claim 1, $R^S$ F, Cl, CN, or linear, branched or cyclic alkyl with 1 to 30 C atoms, in which one or more $CH_2$ groups are optionally replaced by -O-, -S-, -C(=O)—, -C(=S)-, -C(=O)—O—, -O—C(=O)—, -NR$^0$—, -SiR$^0$R$^{00}$-, -CF$_2$-, -CR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or $R^S$ is aryl, heteroaryl, arylalkyl, heteroarylalkyl, aryloxy or heteroaryloxy, wherein each of the aforementioned cyclic groups has 5 to 20 ring atoms, is mon o-or polycyclic, does optionally contain fused rings, and is unsubstituted or substituted by one or more identical or different groups L as defined above, $X^0$ halogen, $Y^1$, $Y^2$ H, F, Cl or CN, $R^0$, $R^{00}$ H or linear or branched alkyl with 1 to 20 C atoms that is optionally fluorinated, a1-d1 0, 1, 2 or 3, preferably with at least one of a1-d1 being ≥1, e1 1, 2 or 3.

4. The compound according to claim 1, characterized in that it is selected from the group consisting of the following formulae

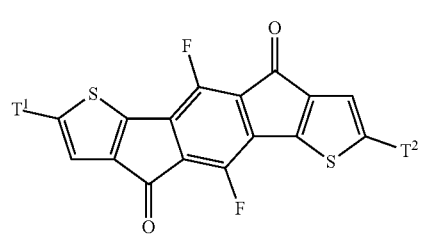

S1-1

-continued

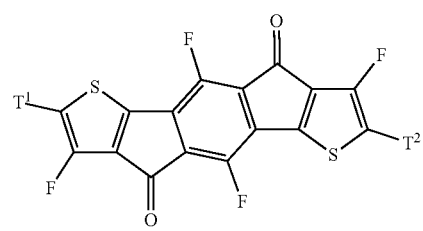

S1-2

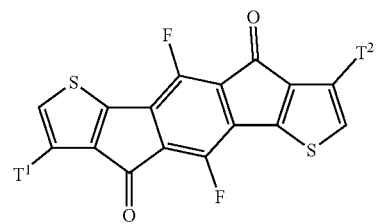

S1-3

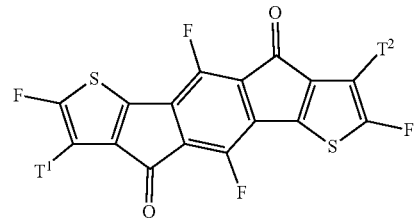

S1-4

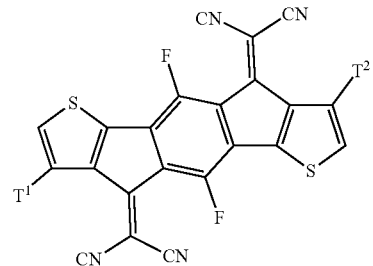

S1-5

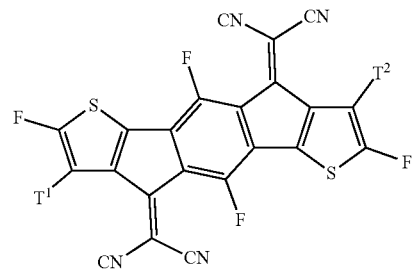

S1-6

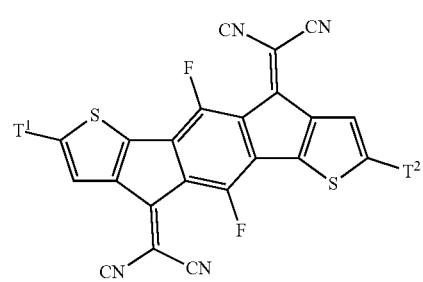

S1-7

-continued
S1-8
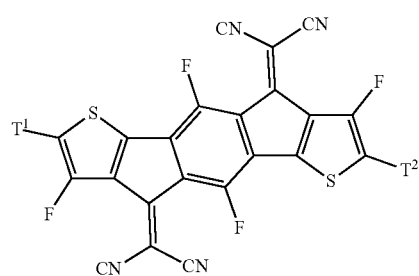
S1-9
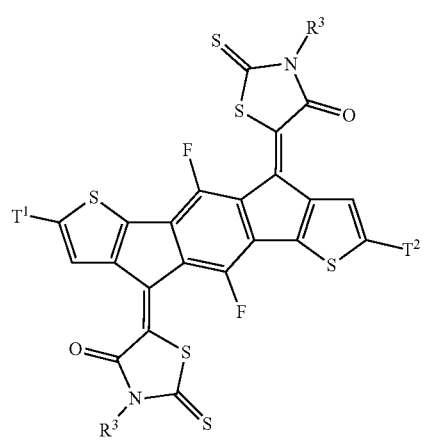
S1-10
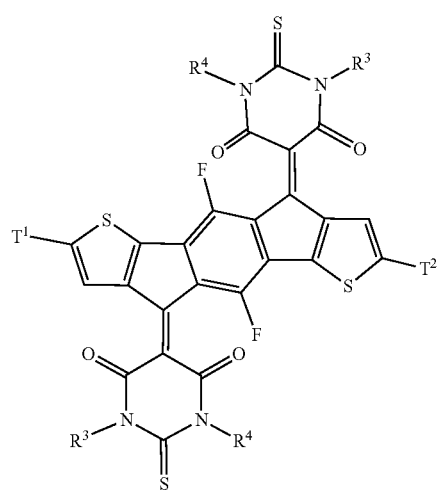
-continued
S1-11
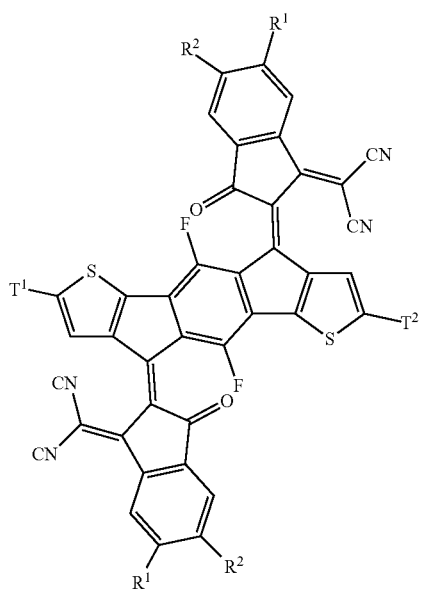
S1-12
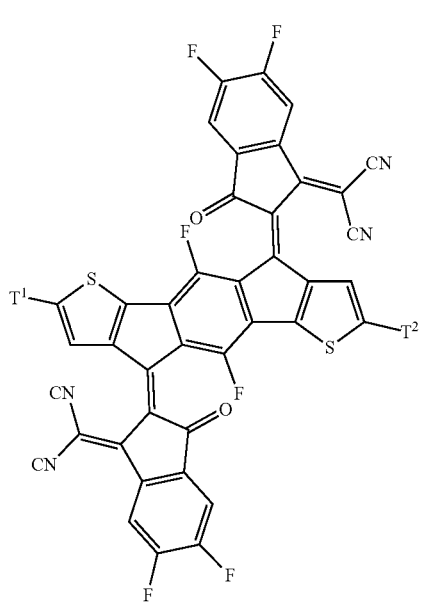
S1-13
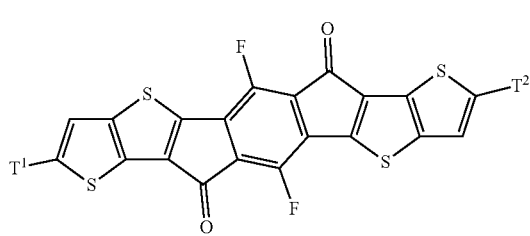

-continued
S1-14
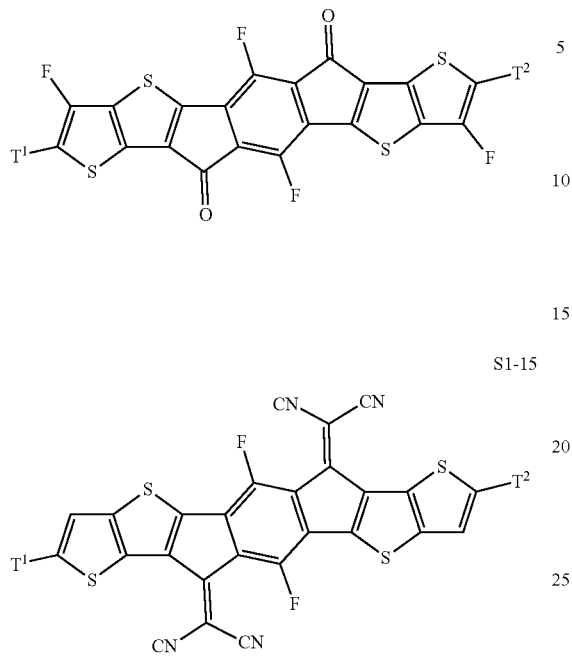
S1-15
S1-16
S1-17
S1-18
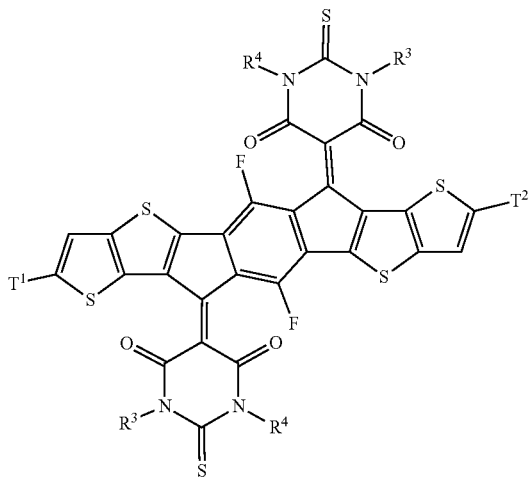
S1-19
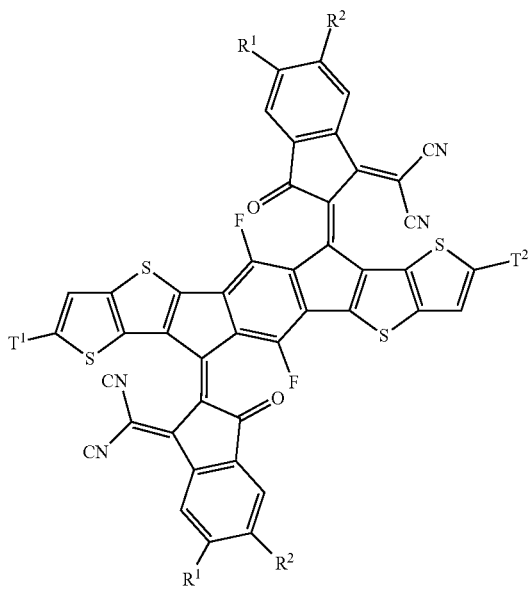

-continued
S1-20
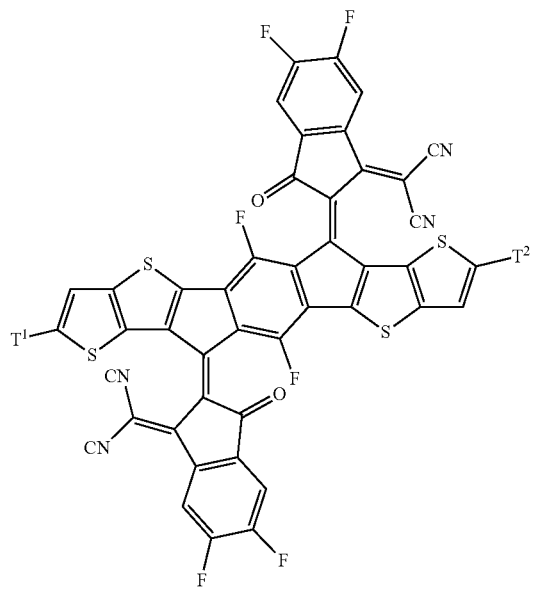
S1-21
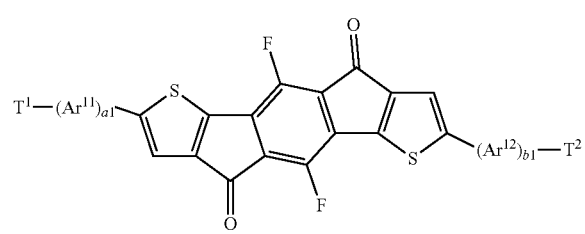
S1-22
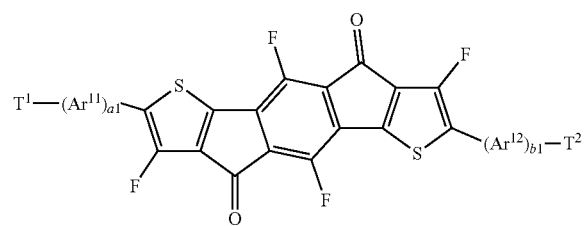
S1-23
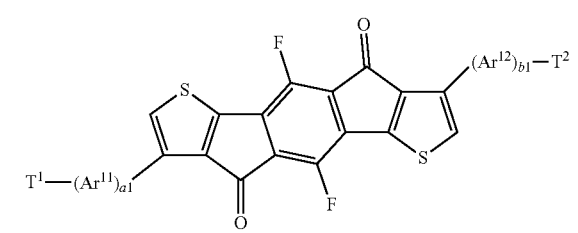
S1-24
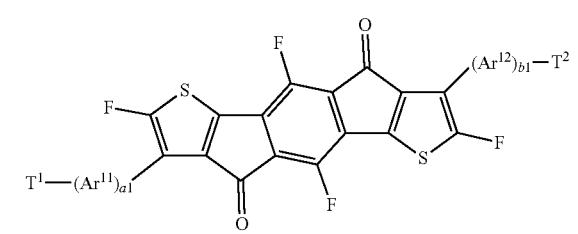
-continued
S1-25
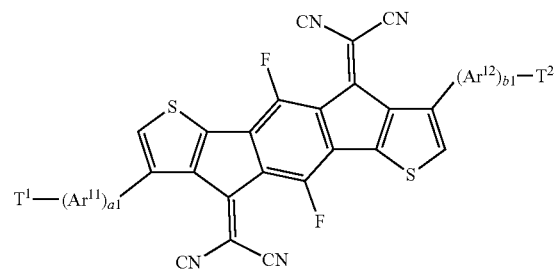
S1-26
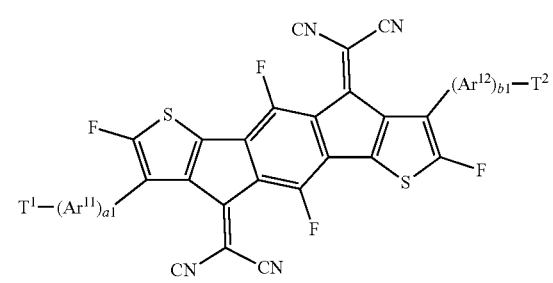
S1-27
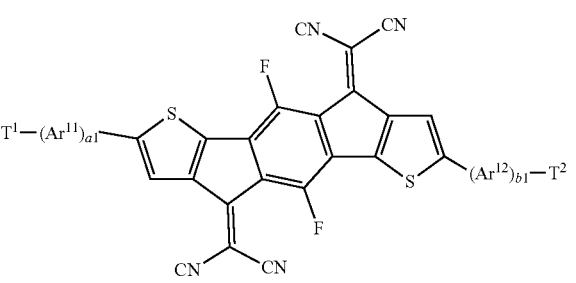
S1-28
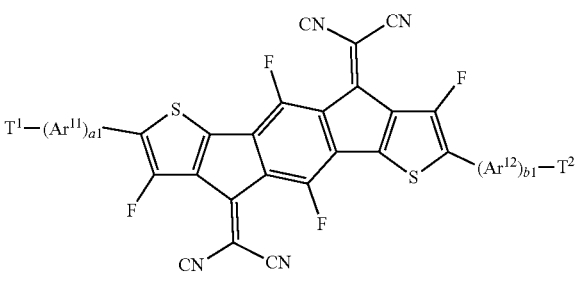
S1-29
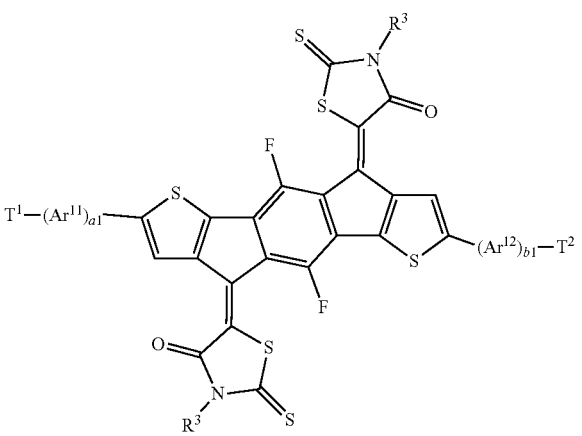

S1-30
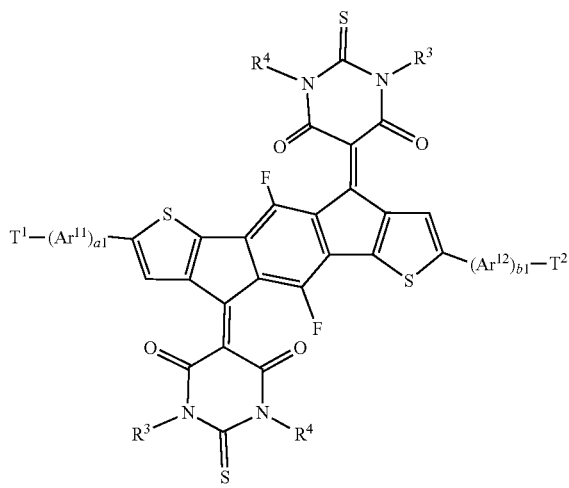
S1-31
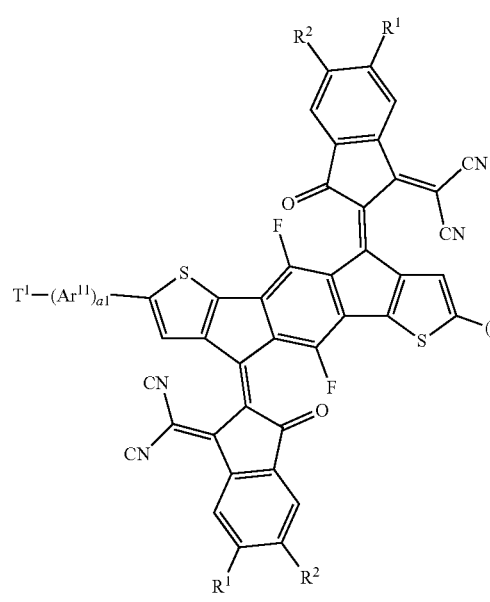
S1-32
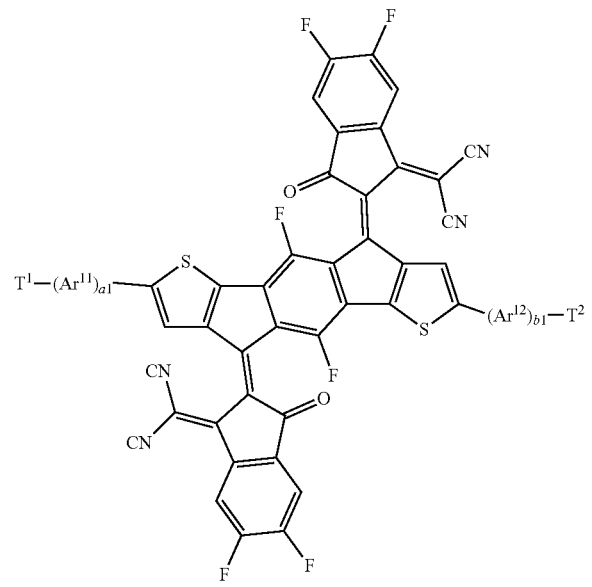
S1-33
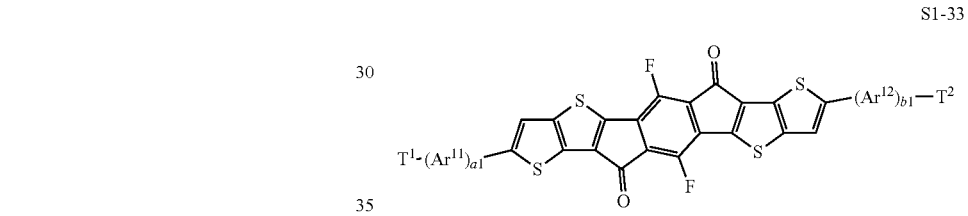
S1-34
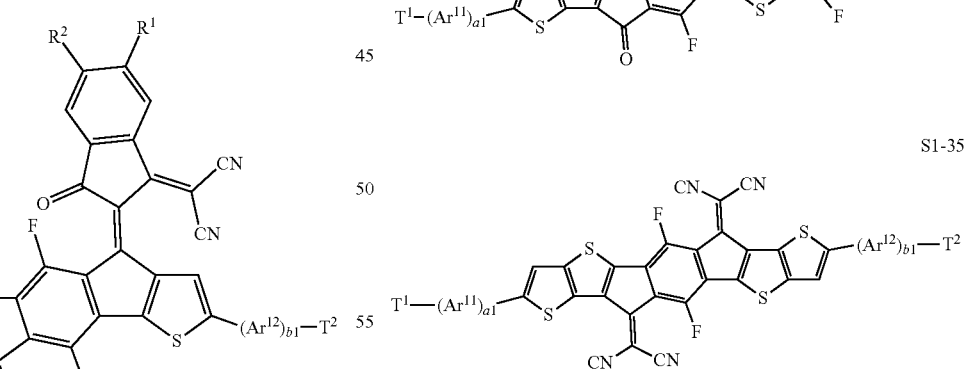
S1-35
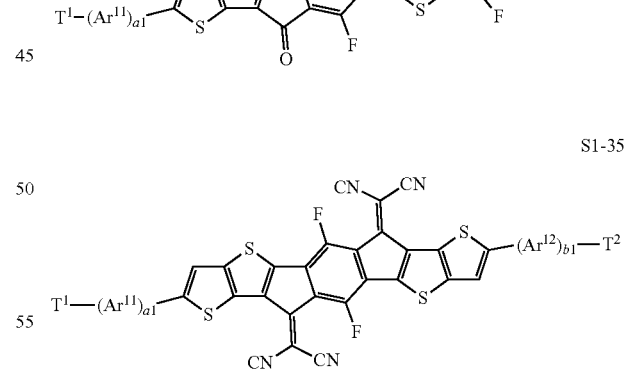
S1-36
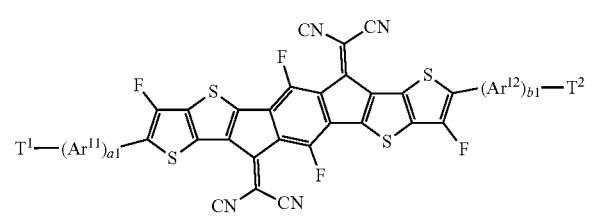

S1-37

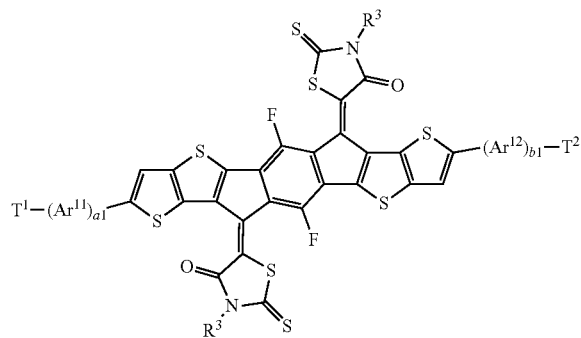

S1-38

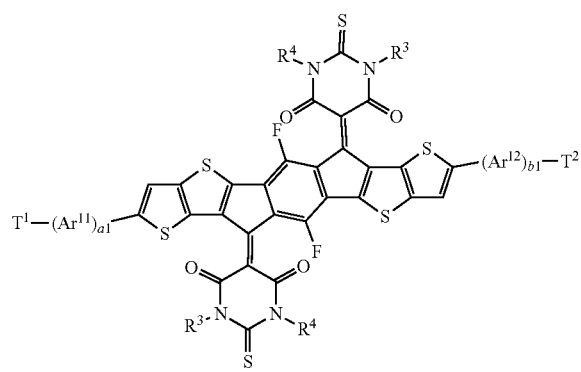

S1-39

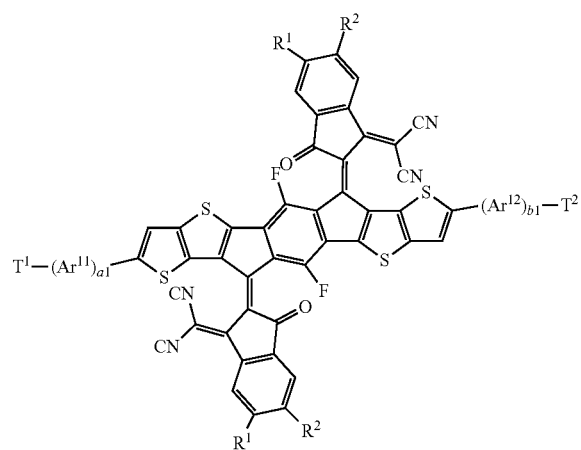

S1-40

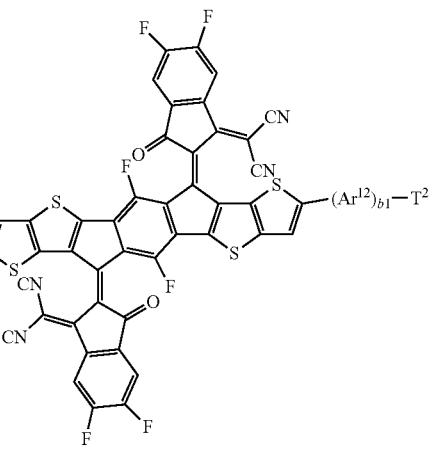

wherein $Ar^{11}$, $Ar^{12}$, $R^1$, $R^2$, $R^3$, $R^4$, $T^1$ and $T^2$ have independently of each other one of the meanings given in claim 1, a1 is 1 or 2 and b1 is 0, 1 or 2.

5. The compound according to claim 1, characterized in that it is a conjugated polymer comprising one or more repeating units of formula I of claim 1 and one or more arylene or heteroarylene units that have from 5 to 20 ring atoms, are mono- or polycyclic, optionally contains fused rings, and are unsubstituted or substituted by one or more identical or different groups L as defined in claim 1.

6. The compound according to claim 5, characterized in that it comprises one or more repeating units of formula II1 or II2, and optionally one or more repeating units of formula II3:

$$-(Ar^1)_a-U-(Ar^2)_b-(Ar^3)_c-(Ar^4)_d- \quad \text{II1}$$

$$-(Ar^1)_a-(Ar^2)_b-U-(Ar^3)_c-(Ar^4)_d- \quad \text{II2}$$

$$-(Ar^1)_a-(Ar^2)_b-(Ar^3)_c-(Ar^4)_d- \quad \text{II3}$$

wherein the individual radicals, independently of each other and on each occurrence identically or differently, have the following meanings U a unit of formula I as defined in claim 5, $Ar^{1-4}$ arylene or heteroarylene that has 5 to 20 ring atoms, is mono- or polycyclic, does optionally contain fused rings, is unsubstituted or substituted by one or more identical or different groups $R^S$, and is different from formula I, or $CY^1=CY^2$- or -C≡C-, $R^S$ F, Cl, CN, or linear, branched or cyclic alkyl with 1 to 30 C atoms, in which one or more $CH_2$ groups are optionally replaced by -O-, -S-, -C(=O)—, -C(=S)-, -C(=O)—O—, -O—C(=O)—, -$NR^0$—, -$SiR^0R^{00}$-, -$CF_2$-, -$CR^0=CR^{00}$-, -$CY^1=CY^2$- or -C≡C- in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or $R^S$ is aryl, heteroaryl, arylalkyl, heteroarylalkyl, aryloxy or heteroaryloxy, wherein each of the aforementioned cyclic groups has 5 to 20 ring atoms, is mon o-or polycyclic, does optionally contain fused rings, and is unsubstituted or substituted by one or more identical or different groups L, L F, Cl, $-NO_2$, -CN, -NC, -NCO, -NCS, -OCN, -SCN, $R^0$, $OR^0$, $SR^0$, $-C(=O)X^0$, $-C(=O) R^0$, $-C(=O)-OR^0$, $-O-C(=O)-R^0$, $-NH_2$, $-NHR^0$, $-NR^0 R^{00}$, $-C(=O)NHR^0$, $-C(=O)NR^0 R^{00}$, $-SO_3R^0$, $-SO_2R^0$, -OH, $-NO_2$, $-CF_3$, $-SF_5$, or optionally substituted silyl, or carbyl or hydrocarbyl with 1 to 30 C atoms that is optionally substituted and optionally comprises one or more hetero atoms, preferably F, -CN, $R^0$, $-OR^0$, $-SR^0$, $-C(=O)-R^0$, $-C(=O)-OR^0$, $-O-C(=O)-R^0$, $-O-C(=O)-OR^0$, $-C(=O)-NHR^0$, or $-C(=O)-NR^0 R^{00}$, $Y^1$, $Y^2$, are, independently, H, F, Cl or CN, $R^0$ and $R^{00}$ are, independently, H or straight-chain or branched alkyl with 1 to 20 C atoms that is optionally fluorinated, a, b, c, d 0 or 1, wherein in formula II3 $a+b+c+d \geq 1$.

7. The compound according to claim 5, characterized in that comprises one or more repeating units selected from formula U1-U4 and one or more repeating units selected from formulae U5-U7

| -(A)- | U1 |
| -(A-Sp)- | U2 |
| -(A-D)- | U3 |
| -(Sp-A-Sp)- | U4 |
| -(D)- | U5 |
| -(D-Sp)- | U6 |
| -(Sp-D-Sp)- | U7 | wherein D denotes a donor unit, A denotes an acceptor unit and Sp denotes a spacer unit, all of which are, independently of each other and on each occurrence identically or differently, selected from arylene or heteroarylene that has from 5 to 20 ring atoms, is mono- or polycyclic, optionally contains fused rings, is unsubstituted or substituted by one or more identical or different groups L, and the polymer contains at least one repeating unit of formulae U1-U4 wherein A is a unit of formula I.

8. The compound according to claim 7, characterized in that it is a conjugated polymer selected from the following formulae

| $-[(D-Sp)_x-(A-Sp)_y]_n-$ | Pi |
| $-[(A-D)_x-(A-Sp)_y]_n-$ | Pii |
| $-[(D)_x-(Sp-A-Sp)_y]_n-$ | Piii |
| $-[D-Sp-A-Sp]_n-$ | Piv |
| $-[D-A]_n-$ | Pv |
| $-[D-Sp-A-Sp]_n$ | Pvi |
| $-[D^1-A-D^2-A]_n$ | Pvii |
| $-[D-A^1-D-A^2]_n$ | Pviii | wherein A, D and Sp are as defined in claim 7, A and D can each, in case of multiple occurrence, also have different meanings, $D^1$ and $D^2$ have one of the meanings given for D and are different from each other, $A^1$ and $A^2$ have one of the meanings given for A and are different from each other, x and y are each, independently of one another, a non- integer >0 and <1, with x+y=1, and n is an integer >1.

9. The compound according to claim 5, characterized in that it is a conjugated polymer selected from the following formulae

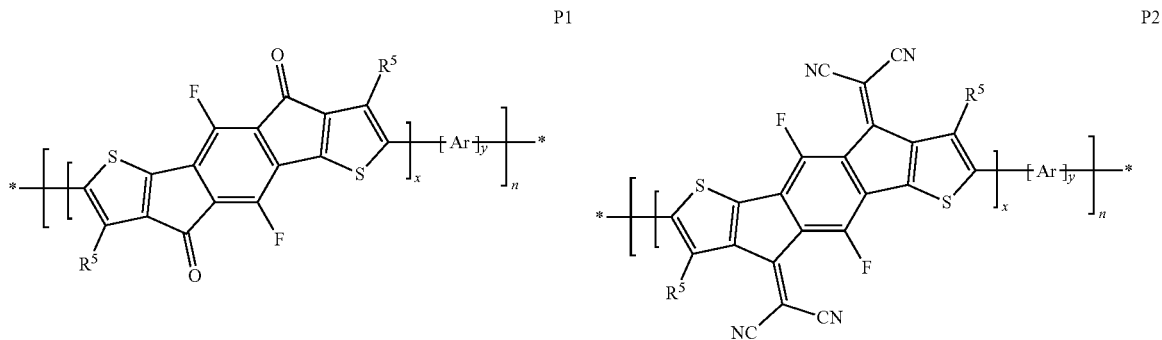

P1  P2

-continued
P3
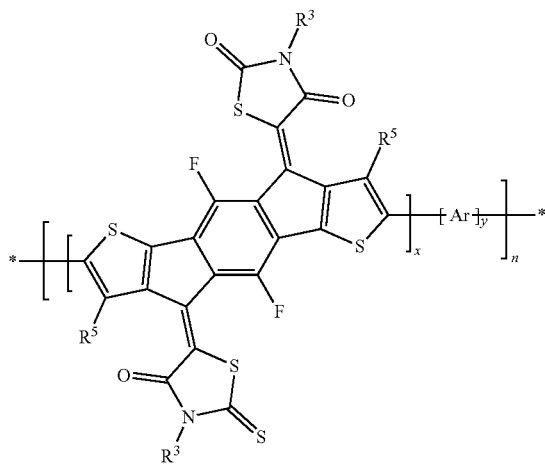
P4
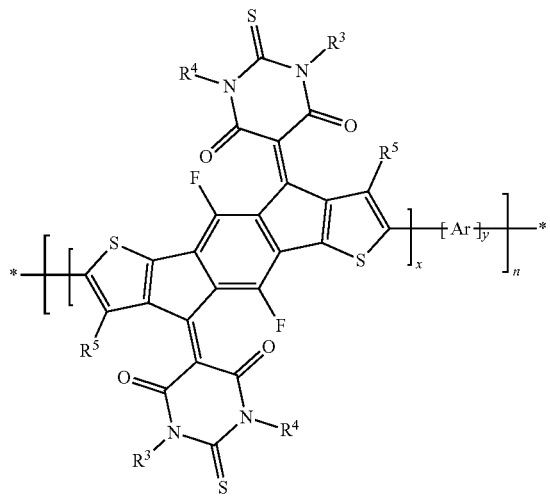
P5
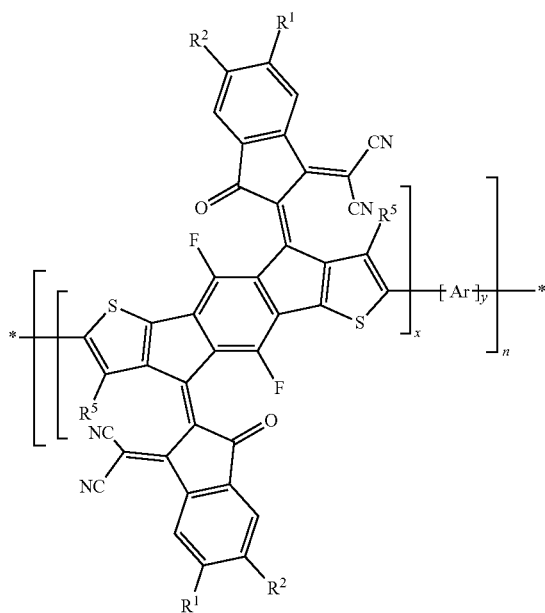
P6
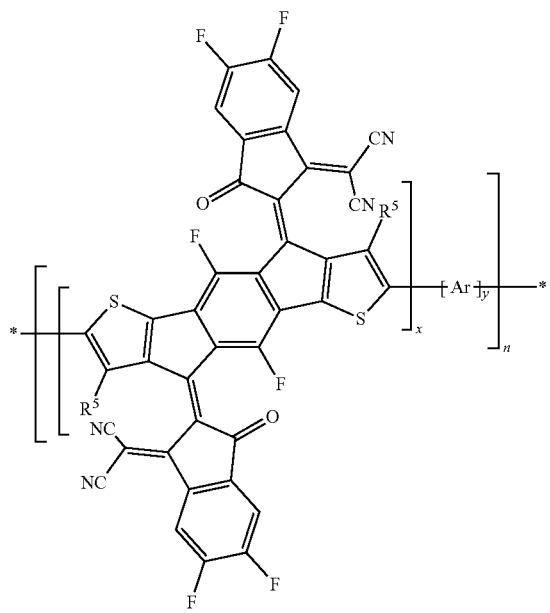
P7
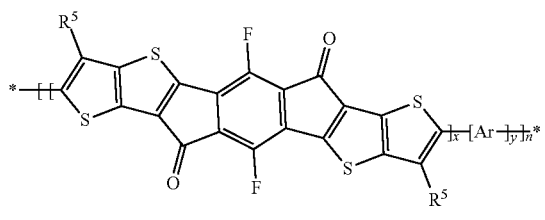
P8
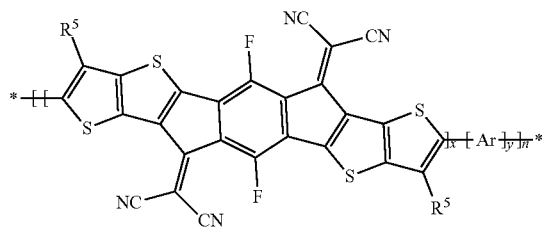

-continued
P9
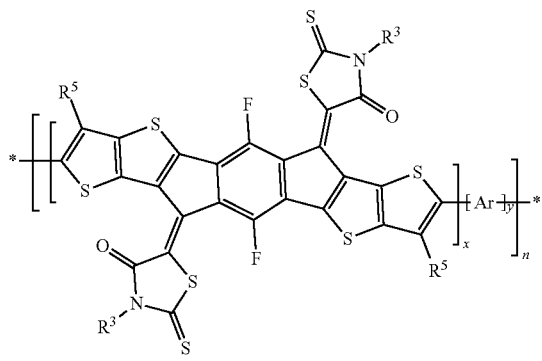
P10
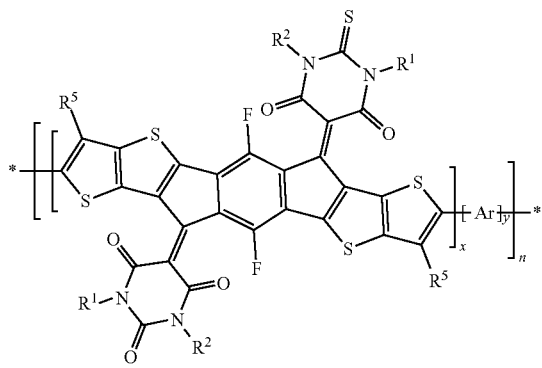
P11
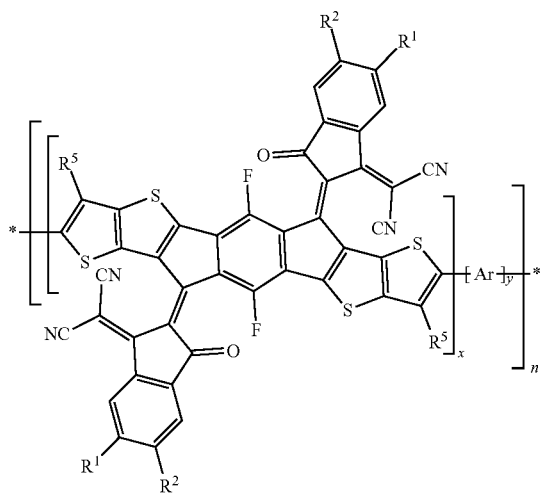
P12
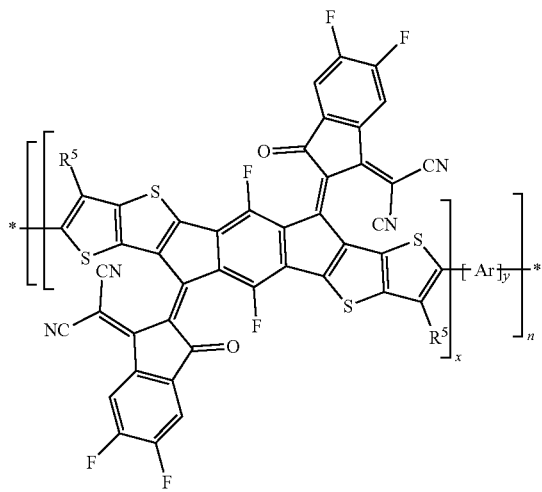
P13
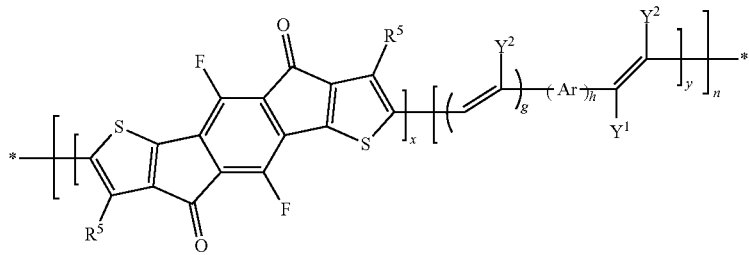
P14
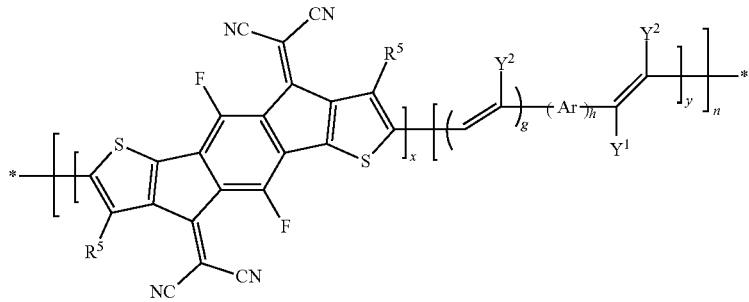

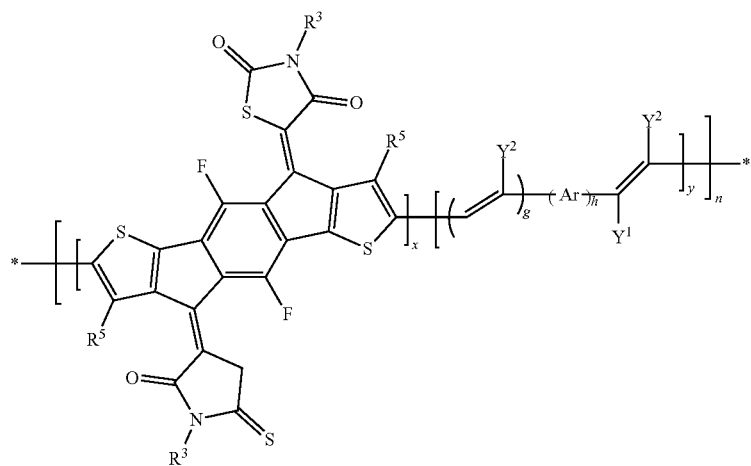
P15
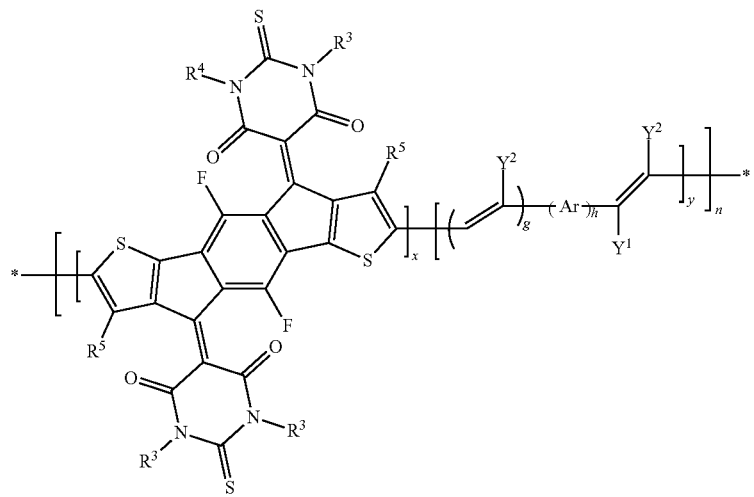
P16
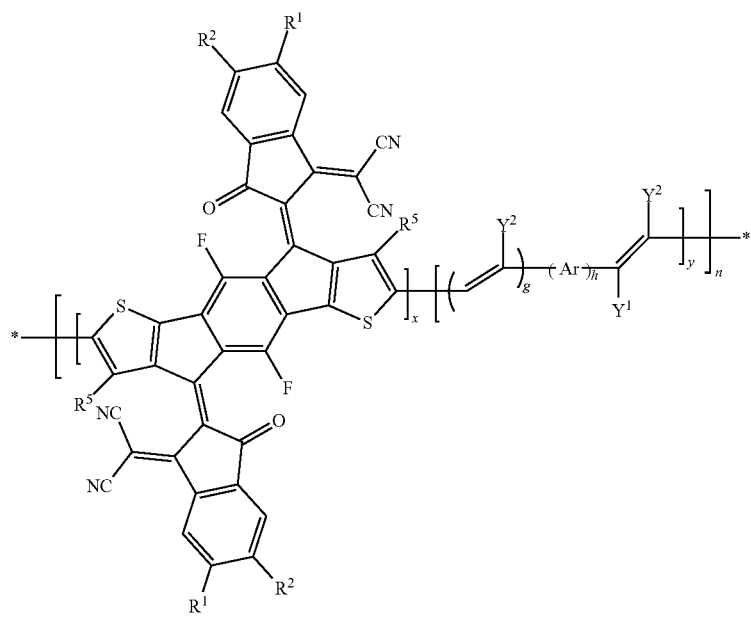
P17

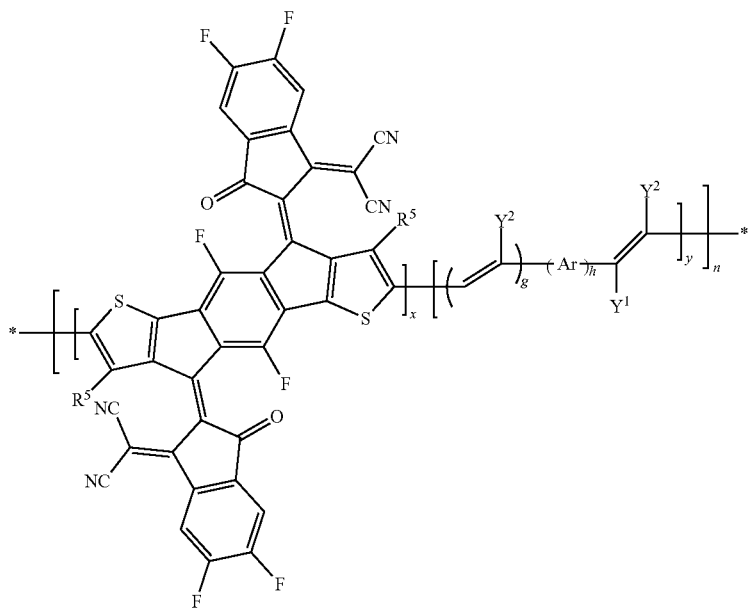
P18
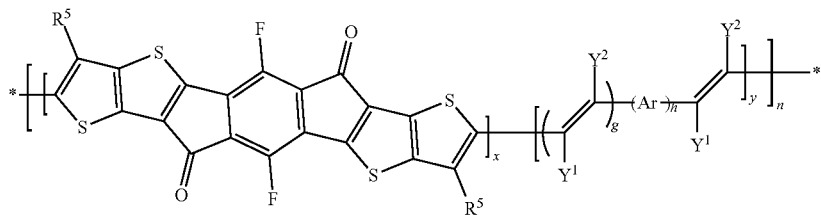
P19
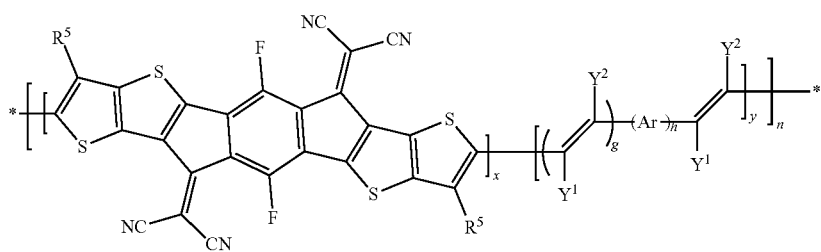
P20
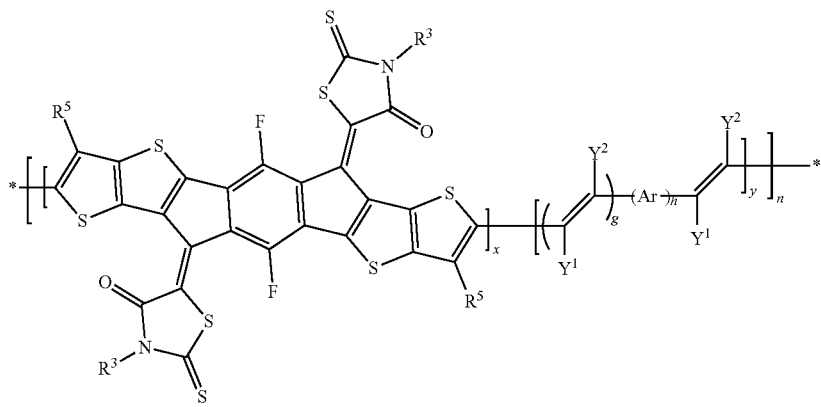
P21

-continued
P22
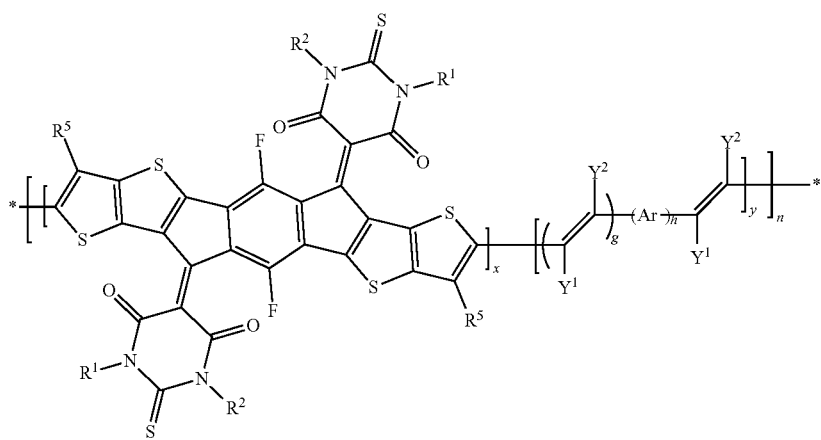
P23
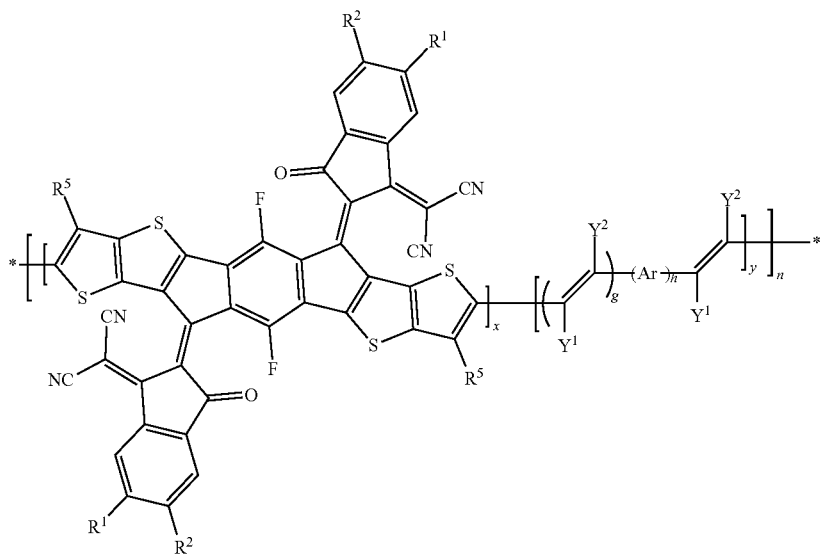
P24
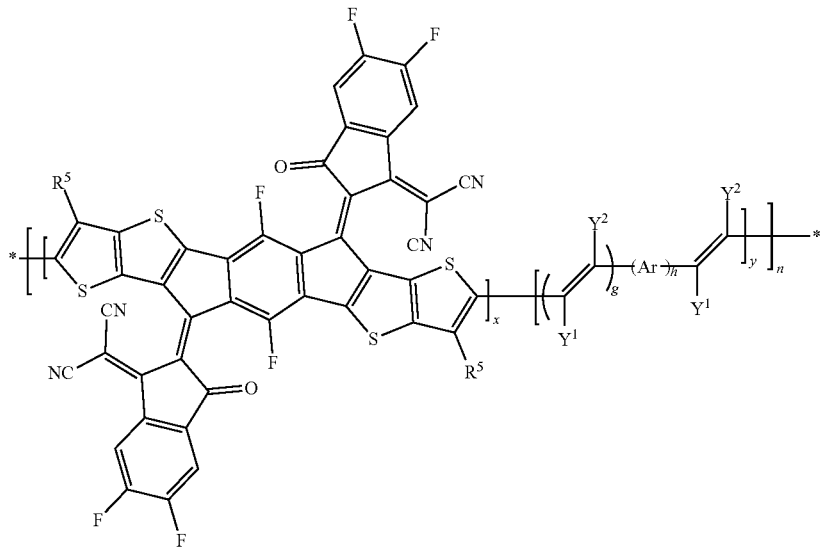

wherein R$^1$, R$^2$, R$^3$, R$^4$ and R$^5$ have independently of each other one of the meanings: H, F, Cl, CN, or straight-chain, branched or cyclic alkyl with 1 to 30 C atoms, in which one or more CH$_2$ groups are optionally replaced by -O-, -S-, -C(=O)—, —C(=S)—, -C(=O)—O—, -O—C(=O)—, -NR$^0$—, -SiR$^0$R$^{00}$-, -CF$_2$-, -CR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, and in which one or more CH$_2$ or CHs groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, L F, Cl, -NO$_2$, -CN, -NC, -NCO, -NCS, -OCN, -SCN, R$^0$ , OR$^0$, SR$^0$, -C(=O)X$^0$, -C(=O) R$^0$ , -C(=O)—OR$^0$, -O—C(=O)—R$^0$ , -NH$_2$, -NHR$^0$, -NR$^0$ R$^{00}$, -C(=O)NHR$^0$, -C(=O)NR$^0$ R$^{00}$, -SO$_3$R$^0$ , -SO$_2$R$^0$ , -OH, -NO$_2$, -CF$_3$, -SF$_5$, or optionally substituted silyl, or carbyl or hydrocarbyl with 1 to 30 C atoms that is optionally substituted and optionally comprises one or more hetero atoms, preferably F, -CN, R$^0$ , -OR$^0$, -SR$^0$, -C(=O)—R$^0$ , -C(=O)—OR$^0$, -O-C(=O)—R$^0$ , -O—C(=O)—OR$^0$, -C(=O)—NHR$^0$, or -C(=O)—NR$^0$ R$^{00}$ Ar arylene or heteroarylene that has 5 to 20 ring atoms, is mono- or polycyclic, does optionally contain fused rings, is unsubstituted or substituted by one or more identical or different groups R$^S$, and is different from formula I, or CY$^1$=CY$^2$- or -C≡C-, R$^S$ F, Cl, CN, or linear, branched or cyclic alkyl with 1 to 30 C atoms, in which one or more CH$_2$ groups are optionally replaced by -O-, -S-, -C(=O)—, -C(=S)-, -C(=O)—O—, -O—C(=O)—, -NR$^0$—, -SiR$^0$R$^{00}$-, -CF$_2$-, -CR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or R$^S$ is aryl, heteroaryl, arylalkyl, heteroarylalkyl, aryloxy or heteroaryloxy, wherein each of the aforementioned cyclic groups has 5 to 20 ring atoms, is mon o-or polycyclic, does optionally contain fused rings, and is unsubstituted or substituted by one or more identical or different groups L Y$^1$, Y$^2$, are, independently, H, F, Cl or CN, R$^0$ and R$^{00}$ are, independently, H or straight-chain or branched alkyl with 1 to 20 C atoms that is optionally fluorinated, x and y are each, independently of one another, a non-integer >0 and <1, with x+y=1, and n is an integer >1.

10. A process of preparing a conjugated polymer according to claim 6, by copolymerising one or more monomers of formula M1 or M2 below

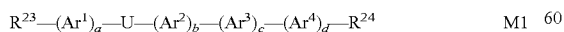
M1

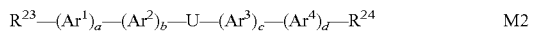
M2

U a unit of formula I as defined in claim 1,

Ar$^{1-4}$ arylene or heteroarylene that has 5 to 20 ring atoms, is mono- or polycyclic, does optionally contain fused rings, is unsubstituted or substituted by one or more identical or different groups RS, and is different from formula I, or CY$^1$=CY$^2$- or -C≡C-, R$^S$ F, Cl, CN, or linear, branched or cyclic alkyl with 1 to 30 C atoms, in which one or more CH$_2$ groups are optionally replaced by -O-, -S-, -C(=O)—, -C(=S)-, -C(=O)—O—, -O—C(=O)—, -NR$^0$—, -SiR$^0$R$^{00}$-, -CF$_2$-, -CR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or R$^S$ is aryl, heteroaryl, arylalkyl, heteroarylalkyl, aryloxy or heteroaryloxy, wherein each of the aforementioned cyclic groups has 5 to 20 ring atoms, is mon o-or polycyclic, does optionally contain fused rings, and is unsubstituted or substituted by one or more identical or different groups L, L F, Cl, -NO$_2$, -CN, -NC, -NCO, -NCS, -OCN, -SCN, R$^0$ , OR$^0$, SR$^0$, -C(=O)X$^0$, -C(=O) R$^0$ , -C(=O)—OR$^0$, -O—C(=O)—R$^0$ , -NH$_2$, -NHR$^0$, -NR$^0$ R$^{00}$, -C(=O)NHR$^0$, -C(=O)NR$^0$ R$^{00}$, -SO$_3$R$^0$ , -SO$_2$R$^0$ , -OH, -NO$_2$, -CF$_3$, -SF$_5$, or optionally substituted silyl, or carbyl or hydrocarbyl with 1 to 30 C atoms that is optionally substituted and optionally comprises one or more hetero atoms, preferably F, -CN, R$^0$ , -OR$^0$, -SR$^0$, -C(=O)—R$^0$ , -C(=O)—OR$^0$, -O-C(=O)—R$^0$, -O—C(=O)—OR$^0$, -C(=O)—NHR$^0$, or -C(=O)—NR$^0$ R$^{00}$, Y$^1$, Y$^2$ are, independently, H, F, Cl or CN, R$^0$, R$^{00}$ are, independently, H or straight-chain or branched alkyl with 1 to 20 C atoms that is optionally fluorinated, a,b,c,d are, independently, 0 or 1, and R$^{23}$ and R$^{24}$ are independently of each other selected from the group consisting of an activated C-H bond, Cl, Br, I, O-tosylate, O-triflate, O-mesylate, O-nonaflate, —SiMe$_2$F, -SiMeF$_2$, -O-SO$_2$Z$^1$, -B(OZ$^2$)$_2$, -CZ$^3$=C (Z$^3$)$_2$, -C≡CH, -C≡CSi(Z$^1$)$_3$, —ZnX$^0$ and -Sn(Z$^4$)$_3$, wherein X$^0$ is halogen, Z$^{1-4}$ are selected from the group consisting of alkyl and aryl, each being optionally substituted, and two groups Z$^2$ may also form a cyclo-boronate group having 2 to 20 C atoms together with the B-and O-atoms with each other, or with one or monomers of the following formulae, in an aryl-aryl coupling reaction

|  | MI |
|---|---|
|  | MII |
|  | MIII |
|  | MIV |
|  | MV |
|  | MVI |
|  | MVII | wherein D denotes a donor unit, A denotes an acceptor unit and Sp denotes a spacer unit, all of which are, independently of each other and on each occurrence identically or differently, selected from arylene or heteroarylene that has from 5 to 20 ring atoms, is mono- or polycyclic, optionally contains fused rings, are is unsubstituted or substituted by one or more identical or different groups L.

11. The compound according to claim 1, which is a monomer of formula M1 or M2

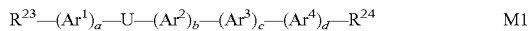   M1

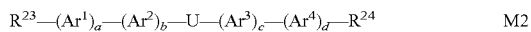   M2 wherein

U a unit of formula I as defined in claim 1,

Ar$^{1-4}$ arylene or heteroarylene that has 5 to 20 ring atoms, is mono- or polycyclic, does optionally contain fused rings, is unsubstituted or substituted by one or more identical or different groups R$^S$, and is different from formula I, or CY$^1$=CY$^2$- or -C≡C-, R$^S$ F, Cl, CN, or linear, branched or cyclic alkyl with 1 to 30 C atoms, in which one or more CH$_2$ groups are optionally replaced by -O-, -S-, -C(=O)—, -C(=S)-, -C(=O)—O—, -O—C(=O)—, -NR$^0$—, -SiR$^0$R$^{00}$-, -CF$_2$-, -CR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or R$^S$ is aryl, heteroaryl, arylalkyl, heteroarylalkyl, aryloxy or heteroaryloxy, wherein each of the aforementioned cyclic groups has 5 to 20 ring atoms, is mono-or polycyclic, does optionally contain fused rings, and is unsubstituted or substituted by one or more identical or different groups L as defined in claim 1, Y$^1$, Y$^2$, R$^0$ and R$^{00}$ are as defined in claim 1, a, b, c, d are, independently, 0 or 1, and R$^{23}$ and R$^{24}$ are independently of each other selected from the group consisting of an activated C-H bond, Cl, Br, I, O-tosylate, O-triflate, O-mesylate, O-nonaflate, —SiMe$_2$F, -SiMeF$_2$, -O-SO$_2$Z$^1$, -B(OZ$^2$)$_2$, -CZ$^3$=C(Z$^3$)$_2$, -C≡CH, -C≡CSi(Z$^1$)$_3$, —ZnX$^0$ and -Sn(Z$^4$)$_3$, wherein X$^0$ is halogen, Z$^{1-4}$ are selected from the group consisting of alkyl and aryl, each being optionally substituted, and two groups Z$^2$ may also form a cycloboronate group having 2 to 20 C atoms together with the B-and O-atoms.

12. The compound according to claim 11, which is selected from the following formulae

   M1a

   M1b

   M1c

   M1d wherein U, R$^{23}$ and R$^{24}$ are as defined in claim 11, and D denotes a donor unit and Sp denotes a spacer unit, all of which are, independently of each other and on each occurrence identically or differently, selected from arylene or heteroarylene that has from 5 to 20 ring atoms, is mono- or polycyclic, optionally contains fused rings, are is unsubstituted or substituted by one or more identical or different groups L L F, Cl, -NO$_2$, -CN, -NC, -NCO, -NCS, -OCN, -SCN, R$^0$, OR$^0$, SR$^0$, -C(=O)X$^0$, -C(=O) R$^0$, -C(=O)—OR$^0$, -O—C(=O)—R$^0$, -NH$_2$, -NHR$^0$, -NR$^0$ R$^{00}$, -C(=O)NHR$^0$, -C(=O)NR$^0$ R$^{00}$, -SO$_3$R$^0$, -SO$_2$R$^0$, -OH, -NO$_2$, -CF$_3$, -SF$_5$, or optionally substituted silyl, or carbyl or hydrocarbyl with 1 to 30 C atoms that is optionally substituted and optionally comprises one or more hetero atoms, preferably F, -CN, R$^0$, -OR$^0$, -SR$^0$, -C(=O)—R$^0$, -C(=O)—OR$^0$, -O-C(=O)—R$^0$, -O—C(=O)—OR$^0$, -C(=O)—NHR$^0$, or -C(=O)—NR$^0$ R$^{00}$ R$^0$ and R$^{00}$ are, independently, H or straight-chain or branched alkyl with 1 to 20 C atoms that is optionally fluorinated.

13. The compound according to claim 11, which is selected from the following formulae

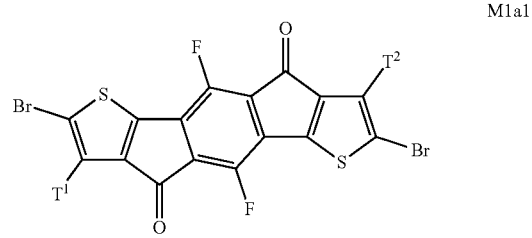   M1a1

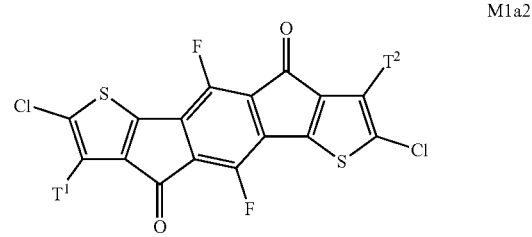   M1a2

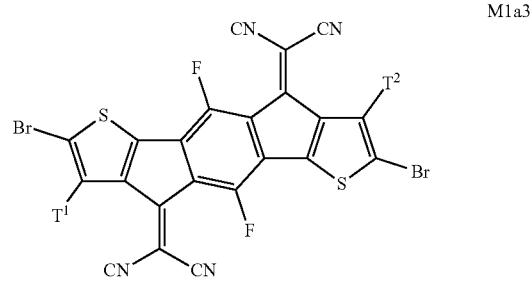   M1a3

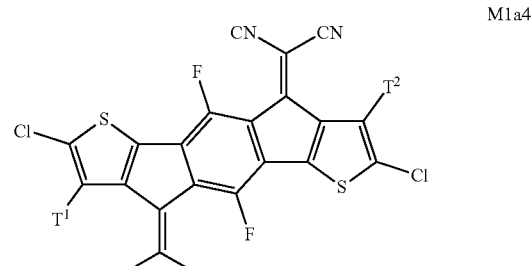   M1a4 when T$^1$ and T$^2$ are independently H, F, Cl, CN, or straight-chain, branched or cyclic alkyl with 1 to 30 C atoms, in which one or more CH$_2$ groups are optionally replaced by -O-, -S-, -C(=O)—, -C(=S)-, -C(=O)—O—, -O—C(=O)—, -NR$^0$—, -SiR$^0$R$^{00}$-, -CF$_2$-, -CR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or aryl, heteroaryl, arylalkyl, hetroarylalkyl, aryloxy, or heteroaryloxy, wherein each of the aforementioned cyclic groups has 5 to 20 ring atoms, is mono- or polycyclic, does optionally contain fused rings, and is unsubstituted or substituted by one or more identical or different groups L, L F, Cl, -NO$_2$, -CN, -NC, -NCO, -NCS, -OCN, -SCN, R$^0$, OR$^0$, SR$^0$, -C(=O)X$^0$, -C(=O) R$^0$, -C(=O)—OR$^0$, -O—C(=O)—R$^0$, -NH$_2$, -NHR$^0$, -NR$^0$ R$^{00}$, -C(=O)NHR$^0$, -C(=O)NR$^0$ R$^{00}$, -SO$_3$R$^0$, -SO$_2$R$^0$, -OH, -NO$_2$, -CF$_3$, -SF$_5$, or optionally substituted silyl, or carbyl or hydrocarbyl with 1 to 30 C atoms that is optionally substituted and optionally comprises one or more hetero atoms, preferably F, -CN, R$^0$, -OR$^0$, -SR$^0$, -C(=O)—R$^0$, -C(=O)-OR$^0$, -O-C(=O)—R$^0$, -O—C(=O)—OR$^0$, -C(=O)—NHR$^0$, or -C(=O)—NR$^0$ R00

R$^0$ and R$^{00}$ are, independently, H or straight-chain or branched alkyl with 1 to 20 C atoms that is optionally fluorinated, X$^0$ is halogen, preferably F or Cl.

14. A composition comprising one or more compounds according to claim 1, and further comprising one or more compounds having one or more of a semiconducting, hole or electron transport, hole or electron blocking, insulating, binding, electrically conducting, photoconducting, photoactive or light emitting property.

15. A composition comprising a compound according to claim 1, which is an electron acceptor or n-type semiconductor, and further comprising one or more electron donors or p-type semiconductors selected from conjugated polymers.

16. A composition comprising a compound according to claim 1 which is an electron donor or p-type semiconductor, and further comprising one or more electron acceptors or n-type semiconductors, selected from fullerenes or substituted fullerenes, or from non-fullerene acceptors.

17. A semiconducting, charge transporting, electrically conducting, photoconducting, photoactive or light emitting material, comprising a compound according to claim 1.

18. A formulation comprising one or more compounds according to claim 1, and further comprising one or more solvents selected from organic solvents.

19. An electronic or optoelectronic device, or a component thereof, or an assembly comprising it, which comprises a compound according to claim 1.

20. The electronic or optoelectronic device of claim 19, which is selected from organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells (PSC), laser diodes, Schottky diodes, photoconductors, photodetectors and thermoelectric devices.

21. The component of claim 19, which is selected from charge injection layers, charge transport layers, interlayers, planarising layers, antistatic films, polymer electrolyte membranes (PEM), conducting substrates and conducting patterns.

22. The assembly of claim 19, which is selected from integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

23. A bulk heterojunction (BHJ) formed from a composition comprising a compound according to claim 1, and one or more additional components selected from:
one or more electron donors or p-type semiconductors selected from conjugated polymers,
one or more electron acceptors or n-type semiconductors, selected from fullerenes or substituted fullerenes, or from non-fullerene acceptors and one or more solvents selected from organic solvents.

* * * * *